(12) United States Patent
Kim

(10) Patent No.: US 11,464,669 B2
(45) Date of Patent: Oct. 11, 2022

(54) DEVICE AND METHOD FOR COOLING LIVING TISSUE

(71) Applicant: RecensMedical.Inc, Ulsan (KR)

(72) Inventor: Gun-Ho Kim, Ulsan (KR)

(73) Assignee: RecensMedical, Inc., Ulsan (KR)

( * ) Notice: Subject to any disclaimer, the term of this patent is extended or adjusted under 35 U.S.C. 154(b) by 923 days.

(21) Appl. No.: 16/212,716

(22) Filed: Dec. 7, 2018

(65) Prior Publication Data

US 2019/0175396 A1    Jun. 13, 2019

Related U.S. Application Data

(63) Continuation of application No. PCT/KR2018/006169, filed on May 30, 2018.
(Continued)

(30) Foreign Application Priority Data

Dec. 29, 2017    (KR) .......................... 10-2017-0184439
Dec. 29, 2017    (KR) .......................... 10-2017-0184440
(Continued)

(51) Int. Cl.
*A61F 7/12*      (2006.01)
*A61B 18/02*     (2006.01)
(Continued)

(52) U.S. Cl.
CPC ................ *A61F 7/12* (2013.01); *A61B 18/02* (2013.01); *A61M 5/422* (2013.01); *A61B 18/20* (2013.01);
(Continued)

(58) Field of Classification Search
CPC .................... A61B 18/02; A61B 18/20; A61B 2018/00011; A61B 2018/00452;
(Continued)

(56) References Cited

U.S. PATENT DOCUMENTS 2,044,823 A    6/1936  Whiteside
4,646,735 A    3/1987  Seney
(Continued)

FOREIGN PATENT DOCUMENTS

CN        2660834 Y     12/2004
CN       104159534 A    11/2014
(Continued)

OTHER PUBLICATIONS

Office Action in U.S. Appl. No. 16/212,713 dated Feb. 16, 2022 in 33 pages.
(Continued)

*Primary Examiner* — Tigist S Demie
(74) *Attorney, Agent, or Firm* — Knobbe Martens Olson & Bear LLP

(57) ABSTRACT

The present disclosure provides a device and a method for cooling living tissues for a medical purpose and other purposes. The cooling device includes a cooling medium contacting the living tissues to be cooled. The cooling medium comprises: a first fluid medicine reservoir configured to be installed outside a main body that couples with a medical cooling device and to move into the main body, wherein the first fluid medicine reservoir stores a first fluid medicine to be injected through a hole at a tip of the main body.

14 Claims, 50 Drawing Sheets

Related U.S. Application Data

(60) Provisional application No. 62/565,095, filed on Sep. 28, 2017, provisional application No. 62/534,206, filed on Jul. 19, 2017, provisional application No. 62/512,189, filed on May 30, 2017.

(30) Foreign Application Priority Data

| Dec. 29, 2017 | (KR) | 10-2017-0184441 |
|---|---|---|
| Dec. 29, 2017 | (KR) | 10-2017-0184442 |
| Dec. 29, 2017 | (KR) | 10-2017-0184443 |
| Dec. 29, 2017 | (KR) | 10-2017-0184444 |
| Dec. 29, 2017 | (KR) | 10-2017-0184445 |
| Dec. 29, 2017 | (KR) | 10-2017-0184446 |
| Dec. 29, 2017 | (KR) | 10-2017-0184447 |

(51) Int. Cl.
*A61M 5/42* (2006.01)
*A61B 18/20* (2006.01)
*A61B 18/00* (2006.01)
*A61F 7/00* (2006.01)
*A61F 7/02* (2006.01)

(52) U.S. Cl.
CPC ........... *A61B 2018/00011* (2013.01); *A61B 2018/00452* (2013.01); *A61F 2007/0052* (2013.01); *A61F 2007/0056* (2013.01); *A61F 2007/0075* (2013.01); *A61F 2007/0087* (2013.01); *A61F 2007/0261* (2013.01); *A61F 2007/126* (2013.01)

(58) Field of Classification Search
CPC ...... A61F 2007/0052; A61F 2007/0056; A61F 2007/0075; A61F 2007/0087; A61F 2007/0261; A61F 2007/126; A61F 7/12; A61M 5/422
See application file for complete search history.

(56) References Cited

U.S. PATENT DOCUMENTS

| 6,099,521 | A | 8/2000 | Shadduck |
|---|---|---|---|
| 6,141,985 | A | 11/2000 | Cluzeau et al. |
| 6,632,219 | B1 | 10/2003 | Baranov et al. |
| 6,669,688 | B2 | 12/2003 | Svaasand et al. |
| 7,037,326 | B2 | 5/2006 | Lee |
| 7,780,656 | B2 | 8/2010 | Tankovich |
| 7,963,959 | B2 | 6/2011 | Silva et al. |
| 8,083,734 | B2 | 12/2011 | Steinfatt et al. |
| D658,775 | S | 5/2012 | Jiangminhui |
| 8,177,827 | B2 | 5/2012 | Shapiro |
| 8,256,233 | B2 | 9/2012 | Boyden et al. |
| 8,409,184 | B2 | 4/2013 | Baust et al. |
| 8,652,131 | B2 | 2/2014 | Muller et al. |
| 8,672,879 | B2 | 3/2014 | Grant et al. |
| 8,747,397 | B2 | 6/2014 | Baust et al. |
| 8,788,060 | B2 | 7/2014 | Nebrigic et al. |
| 8,858,583 | B2 | 10/2014 | Shtram et al. |
| 9,017,318 | B2 | 4/2015 | Fourkas et al. |
| 9,039,688 | B2 | 5/2015 | Palmer, III et al. |
| 9,066,712 | B2 | 6/2015 | Fourkas et al. |
| 9,113,855 | B2 | 8/2015 | Burger et al. |
| 9,155,584 | B2 | 10/2015 | Fourkas et al. |
| 9,398,975 | B2 | 7/2016 | Müller et al. |
| 9,522,031 | B2 | 12/2016 | Anderson et al. |
| 9,549,773 | B2 | 1/2017 | Anderson et al. |
| 9,642,741 | B2 | 5/2017 | Feng et al. |
| 9,801,677 | B2 | 10/2017 | Anderson et al. |
| 9,855,166 | B2 | 1/2018 | Anderson et al. |
| 9,956,355 | B2 | 5/2018 | Besirli et al. |
| 9,974,684 | B2 | 5/2018 | Anderson et al. |
| D822,841 | S | 7/2018 | Cheng |
| 10,085,881 | B2 | 10/2018 | Karnik et al. |
| 10,154,870 | B2 | 12/2018 | Ottanelli |
| 10,188,444 | B2 | 1/2019 | Fourkas et al. |
| 10,213,244 | B2 | 2/2019 | Fourkas et al. |
| 10,322,248 | B2 | 6/2019 | Besirli et al. |
| 10,349,997 | B1 | 7/2019 | O'Reilly |
| 10,363,080 | B2 | 7/2019 | Elkins et al. |
| 10,543,032 | B2 | 1/2020 | Babkin |
| 2004/0102768 | A1 | 5/2004 | Cluzeau et al. |
| 2004/0111087 | A1 | 6/2004 | Stern et al. |
| 2005/0005626 | A1 | 1/2005 | McMahon |
| 2005/0059940 | A1 | 3/2005 | Weber et al. |
| 2005/0261753 | A1 | 11/2005 | Littrup et al. |
| 2006/0200117 | A1 | 9/2006 | Hermans |
| 2006/0213509 | A1 | 9/2006 | Marin et al. |
| 2007/0005048 | A1 | 1/2007 | Niedbala et al. |
| 2008/0164296 | A1 | 7/2008 | Shelton et al. |
| 2008/0221561 | A1 | 9/2008 | Geiger et al. |
| 2009/0005843 | A1 | 1/2009 | Smyth |
| 2009/0036846 | A1 | 2/2009 | Dacquay et al. |
| 2009/0062751 | A1 | 3/2009 | Newman, Jr. |
| 2009/0124972 | A1 | 5/2009 | Fischer et al. |
| 2009/0149930 | A1 | 6/2009 | Schenck |
| 2009/0163902 | A1 | 6/2009 | DeLonzor et al. |
| 2010/0010480 | A1 | 1/2010 | Mehta et al. |
| 2010/0087805 | A1 | 4/2010 | Citterio et al. |
| 2010/0196343 | A1 | 8/2010 | O'Neil et al. |
| 2010/0198207 | A1 | 8/2010 | Elkins et al. |
| 2011/0072834 | A1 | 3/2011 | Ishikura et al. |
| 2011/0098791 | A1 | 4/2011 | Kim |
| 2011/0137268 | A1 | 6/2011 | Thomason et al. |
| 2011/0152850 | A1 | 6/2011 | Niedbala et al. |
| 2011/0177474 | A1 | 7/2011 | Jamnia et al. |
| 2011/0224761 | A1 | 9/2011 | Manstein |
| 2012/0130458 | A1 | 5/2012 | Ryba et al. |
| 2012/0191166 | A1 | 7/2012 | Callister et al. |
| 2012/0232549 | A1 | 9/2012 | Willyard et al. |
| 2012/0265278 | A1 | 10/2012 | Fourkas et al. |
| 2013/0116719 | A1 | 5/2013 | Shtram et al. |
| 2013/0184694 | A1 | 7/2013 | Fourkas et al. |
| 2013/0218148 | A1 | 8/2013 | Burger et al. |
| 2013/0296811 | A1 | 11/2013 | Bangera et al. |
| 2013/0315924 | A1 | 11/2013 | Hsu et al. |
| 2014/0012226 | A1 | 1/2014 | Hochman |
| 2014/0142507 | A1 | 5/2014 | Armes |
| 2014/0200511 | A1 | 7/2014 | Boyden et al. |
| 2014/0277023 | A1 | 9/2014 | Sekino et al. |
| 2014/0303608 | A1 | 10/2014 | Taghizadeh |
| 2014/0303696 | A1 | 10/2014 | Anderson et al. |
| 2015/0051545 | A1 | 2/2015 | Henderson et al. |
| 2016/0058488 | A1 | 3/2016 | Fourkas et al. |
| 2016/0135864 | A1 | 5/2016 | Babkin |
| 2016/0143802 | A1 | 5/2016 | Tranfaglia et al. |
| 2016/0183996 | A1 | 6/2016 | Burger et al. |
| 2016/0242956 | A1 | 8/2016 | Gomez |
| 2016/0262820 | A1 | 9/2016 | Allison et al. |
| 2016/0279350 | A1* | 9/2016 | Besirli ............ A61F 7/00 |
| 2017/0014174 | A1 | 1/2017 | Levine et al. |
| 2017/0062793 | A1 | 3/2017 | Zakharyan et al. |
| 2017/0231816 | A1 | 8/2017 | Ryan |
| 2017/0232243 | A1 | 8/2017 | Herweijer |
| 2017/0304558 | A1 | 10/2017 | Besirli et al. |
| 2017/0354451 | A1 | 12/2017 | Marin et al. |
| 2018/0116705 | A1 | 5/2018 | Lee et al. |
| 2018/0235805 | A1 | 8/2018 | Burger et al. |
| 2018/0310979 | A1 | 11/2018 | Peled et al. |
| 2019/0000524 | A1 | 1/2019 | Rosen et al. |
| 2019/0015146 | A1 | 1/2019 | DuBois et al. |
| 2019/0038459 | A1 | 2/2019 | Karnik et al. |
| 2019/0175394 | A1 | 6/2019 | Kim |
| 2019/0175395 | A1 | 6/2019 | Kim |
| 2019/0175396 | A1 | 6/2019 | Kim |
| 2019/0239938 | A1 | 8/2019 | Kazic et al. |
| 2019/0254866 | A1 | 8/2019 | Whiteley et al. |
| 2019/0290881 | A1 | 9/2019 | Kim |
| 2020/0007882 | A1 | 1/2020 | Abe et al. |
| 2020/0007883 | A1 | 1/2020 | Toresson |

(56) References Cited

U.S. PATENT DOCUMENTS

| | | | |
|---|---|---|---|
| 2020/0054483 A1 | 2/2020 | Kim | |
| 2020/0100934 A1 | 4/2020 | Ariano et al. | |
| 2020/0309436 A1 | 10/2020 | Kim | |

FOREIGN PATENT DOCUMENTS

| | | |
|---|---|---|
| EP | 1 030 611 B1 | 9/2004 |
| EP | 1 401 347 B1 | 8/2011 |
| EP | 2 010 087 B1 | 11/2014 |
| EP | 2 910 276 A1 | 8/2015 |
| EP | 2 759 272 B1 | 11/2018 |
| JP | 04-092663 A | 3/1992 |
| JP | 06-086818 A | 3/1994 |
| JP | 10-230435 A | 9/1998 |
| JP | 2002-505155 A | 2/2002 |
| JP | 4049358 B2 | 2/2002 |
| JP | 2004-515270 A | 5/2004 |
| JP | 2005-080832 A | 3/2005 |
| JP | 2006-130055 A | 5/2006 |
| JP | 2008-212638 A | 9/2008 |
| JP | 2008-545462 A | 12/2008 |
| JP | 2009-034273 A | 2/2009 |
| JP | 2009-056320 A | 3/2009 |
| JP | 2011-077314 A | 4/2011 |
| JP | 2012-143279 A | 8/2012 |
| JP | 2013-142410 A | 7/2013 |
| JP | 2014-198238 A | 10/2014 |
| JP | 2015-510802 A | 4/2015 |
| JP | 2015-532141 A | 11/2015 |
| JP | 2017-113635 A | 6/2017 |
| KR | 20-1998-0005117 U | 3/1998 |
| KR | 2019-980005117 U | 3/1998 |
| KR | 10-0200669 B1 | 3/1999 |
| KR | 10-2003-0068633 A | 8/2003 |
| KR | 20-0346052 Y1 | 3/2004 |
| KR | 10-2004-0093706 A | 11/2004 |
| KR | 10-0786539 B1 | 12/2007 |
| KR | 10-0790758 B1 | 12/2007 |
| KR | 10-2008-0045022 A | 5/2008 |
| KR | 10-0851274 B1 | 8/2008 |
| KR | 10-2008-0104151 A | 12/2008 |
| KR | 10-2010-0041207 A | 4/2010 |
| KR | 10-2010-0060222 A | 6/2010 |
| KR | 10-2010-0135863 A | 12/2010 |
| KR | 10-1053835 B1 | 8/2011 |
| KR | 10-2011-0119640 A | 11/2011 |
| KR | 10-2012-0073070 A | 7/2012 |
| KR | 10-2012-0115703 A | 10/2012 |
| KR | 10-2013-0020852 A | 3/2013 |
| KR | 10-2013-0087770 A | 8/2013 |
| KR | 10-1366126 B1 | 2/2014 |
| KR | 10-1386137 B1 | 4/2014 |
| KR | 10-2014-0052667 A | 5/2014 |
| KR | 10-2014-0069431 A | 6/2014 |
| KR | 10-2015-0030264 A | 3/2015 |
| KR | 10-2015-0062492 A | 6/2015 |
| KR | 10-2016-0048425 A | 5/2016 |
| KR | 10-2016-0146337 A | 12/2016 |
| KR | 10-1707659 B1 | 2/2017 |
| KR | 10-1719459 B1 | 3/2017 |
| KR | 10-2017-0041776 A | 4/2017 |
| KR | 10-2017-0083399 A | 7/2017 |
| KR | 10-2017-0089842 A | 8/2017 |
| KR | 10-1813652 B1 | 8/2017 |
| KR | 10-2017-0130470 A | 11/2017 |
| KR | 10-1819204 B1 | 1/2018 |
| KR | 10-2018-0054247 A | 5/2018 |
| KR | 10-1840346 B1 | 5/2018 |
| KR | 10-1862127 B1 | 5/2018 |
| KR | 10-2018-0109828 A | 10/2018 |
| KR | 10-1936890 B1 | 1/2019 |
| KR | 10-2019-0074150 A | 6/2019 |
| WO | WO 2016/154399 A1 | 9/2016 |
| WO | WO 2018/231868 A1 | 12/2018 |

OTHER PUBLICATIONS

International Search Report dated Mar. 27, 2020, for PCT/KR2019/017328.
Korean Notice of Allowance dated Apr. 2, 2020 for KR 10-2018-0052601 with Eng. Translation.
Korean Office Action dated May 10, 2020 for KR10-2018-0049115, with Eng. Translation.
Office Action dated Oct. 2, 2019 for U.S. Appl. No. 15/828,449.
Office Action dated May 15, 2020 for U.S. Appl. No. 15/828,449.
Office Action dated Jun. 26, 2020 for U.S. Appl. No. 16/412,296.
Chinese First Office Action dated Dec. 22, 2020 for CN 201780083128.0.
European (EUIPO) Examination Report dated Jan. 11, 2021 for 008309504-003.
European (EUIPO) Examination Report dated Feb. 5, 2021 for 008309504-003.
International Search Report dated Mar. 4, 2021, for PCT/KR2020/012886.
International Written Opinion dated Mar. 4, 2021, for PCT/KR2020/012886.
Office Action dated Sep. 13, 2019 for U.S. Appl. No. 16/412,296.
Final Office Action dated Jan. 31, 2020 for U.S. Appl. No. 16/412,296.
Final Office Action dated Oct. 28, 2020 for U.S. Appl. No. 16/412,296.
Office Action dated Dec. 24, 2020 for U.S. Appl. No. 17/036,269.
Office Action dated Dec. 8, 2020 for U.S. Appl. No. 17/036,311.
Notice of Allowance dated Feb. 22, 2021 for U.S. Appl. No. 17/036,311.
Office Action dated Nov. 5, 2020 for U.S. Appl. No. 29/701,630.
Notice of Allowance dated Feb. 3, 2021 for U.S. Appl. No. 29/701,630.
Office Action dated Nov. 5, 2020 for U.S. Appl. No. 29/701,631.
Notice of Allowance dated Feb. 3, 2021 for U.S. Appl. No. 29/701,631.
Korean Office Action dated Nov. 26, 2019 for KR 10-2018-0049108.
Korean Office Action dated Nov. 27, 2019 for KR 10-2018-0049109.
Korean Office Action dated Dec. 6, 2019 for KR 10-2018-0049110.
Korean Office Action dated Dec. 9, 2019 for KR 10-2018-0049115.
Korean Office Action dated Dec. 10, 2019 for KR 10-2018-0049117.
International Search Report dated Jun. 4, 2018 for PCT/KR2017/012935.
International Search Report dated Jul. 6, 2018 for PCT/KR2018/003773.
International Search Report dated Aug. 8, 2018 for PCT/KR2017/013901.
International Search Report dated May 30, 2019 for PCT/KR2018/016491.
Korean Notice of Allowance dated Jun. 30, 2018 for KR 10-2016-0151947.
Korean Office Action dated Oct. 22, 2018 for KR 10-2017-0162715.
Korean Office Action dated Oct. 22, 2018 for KR 10-2017-0162716.
Korean Office Action dated Jul. 29, 2019 for KR 10-2017-0162717.
Korean Notice of Allowance dated Jul. 29, 2019 for KR 10-2017-0162716.
Korean Notice of Allowance dated Aug. 29, 2019 for KR 10-2017-0162715.
Korean Office Action dated Oct. 8, 2019 for KR 10-2018-0052601—no translation avail.
International Search Report and Written Opinion dated Aug. 14, 2019 for PCT/KR2019/005105.
International Search Report and Written Opinion dated Nov. 15, 2019 for PCT/KR2019/009411.
Korean Final Office Action dated Jan. 17, 2020 for KR 10-2017-0162717 with Translation.
Korean Final Office Action dated May 10, 2020, for KR 10-2018-0049109 with Translation.
Korean Notice of Allowance dated Jun. 24, 2020 for KR 10-2018-0049109—w/ Trans.
Korean Final Office Action dated May 10, 2020 for KR 10-2018-0049110—w/ Trans.

(56) References Cited

OTHER PUBLICATIONS

Korean Notice of Allowance dated Jun. 22, 2020 for KR 10-2018-0049110—w/ Trans.
Korean Notice of Allowance dated Jul. 21, 2020 for KR 10-2018-0049115—w/ Trans.
Korean Notice of Allowance dated May 10, 2020 for KR 10-2018-0049117.
Korean Second Office Action, with translation, dated Oct. 28, 2019 for KR 10-2018-0052601.
Korean Office Action dated Oct. 22, 2018, for KR 10-2018-0117138.
Smith et al., "Ice Anesthesia for Injection of Dermal Fillers," The American Society for Dermatologic Surgery Inc., Dermatol. Surg 2010;36:812-814, 2010.
Sarifakioglu, et al., "Evaluating the Effects of Ice Application on the Pain Felt During Botulinum Toxin Type-A Injections," Annals of Plastic Surgery, vol. 53, No. 6, Dec. 2004.
International Search Report and Written Opinion in PCT Application No. PCT/KR2018/006169 dated Nov. 7, 2018 in 17 pages.
Office Action in Chinese Application No. 201880022501.6 dated Jul. 6, 2021 in 12 pages.
Office Action in U.S. Appl. No. 17/335,330 dated Sep. 1, 2021 in 11 pages.
Office Action in U.S. Appl. No. 16/212,712 dated May 24, 2022 in 29 pages.
Written Opinion in PCT Application No. PCT/KR2018/003773 dated Jul. 6, 2018 in 18 pages.
Korean Office Action dated Jul. 15, 2022 for KR 10-2017-0184439 w/Trans.
Korean Office Action dated Jul. 15, 2022 for KR 10-2017-0184441 w/Trans.

* cited by examiner

AIR FLOW

DEVICE AND METHOD FOR COOLING LIVING TISSUE

CROSS-REFERENCE TO RELATED APPLICATIONS

This application claims the benefit under 35 U.S.C. § 120 and § 365(c) to a prior PCT International Application No. PCT/KR2018/006169, filed on May 30, 2018, which claims the benefits of U.S. Provisional Patent Application No. 62/512,189, filed on May 30, 2017, U.S. Provisional Patent Application No. 62/534,206, filed on Jul. 19, 2017, U.S. Provisional Patent Application No. 62/565,095, filed on Sep. 29, 2017, Korean Patent Application No. 10-2017-0184439, filed on Dec. 29, 2017, Korean Patent Application No. 10-2017-0184440, filed on Dec. 29, 2017, Korean Patent Application No. 10-2017-0184441, filed on Dec. 29, 2017, Korean Patent Application No. 10-2017-0184442, filed on Dec. 29, 2017, Korean Patent Application No. 10-2017-0184443, filed on Dec. 29, 2017, Korean Patent Application No. 10-2017-0184444, filed on Dec. 29, 2017, Korean Patent Application No. 10-2017-0184445, filed on Dec. 29, 2017, Korean Patent Application No. 10-2017-0184446, filed on Dec. 29, 2017, and Korean Patent Application No. 10-2017-0184447, filed on Dec. 29, 2017, the entire contents of which are incorporated herein by reference.

BACKGROUND OF THE DISCLOSURE

Field

The present disclosure relates to a device and a method for cooling living tissues for a medical purpose and other purposes.

Background

With the aging population and increasing number of patients with diabetes, vision threatening retinal diseases such as age-related macular degeneration, diabetic retinopathy, and diabetic vein occlusions are increasing rapidly. For the last decade, intravitreal injection therapy (IVT), the periodic injections of medication such as ranibizumab and aflibercept directly into the patient eyes, has been found to be more successful in treating the aforementioned vision threatening retinal diseases than laser therapy and vitreous replacement procedures, and become the standard of care in these patients. As a result, the majority of these patients with age-related macular degeneration, diabetic retinopathy, and retinal vein occlusions are treated with IVTs, and according to the American Society of Retina Specialists, the number of IVTs is estimated to be over 6 million in 2016 in the United States alone and reach at least 10 million by 2020.

IVT is a painful and psychologically stressful procedure, and patients often demand maximal anesthesia before an injection. Retina specialists typically choose one among three anesthesia methods when such maximal anesthesia is required, cotton tipped applicators soaked with lidocaine, viscous anesthetic, or subconjunctival lidocaine injection. These methods require several minutes for the onset of maximal anesthesia, increasing the time required for patient preparation by several fold. While the method of eye drops of topical anesthetics is the most time-efficient method, the level of anesthesia is moderate and patients often complain of injection pain.

Both the aforementioned maximal and moderate anesthesia options rely on pharmacologic anesthesia agents. Compared with anesthesiology in other areas, ophthalmic anesthesia requires several unique carefulness such as systemic diseases of the patient, systemic reaction by treated medicines and interaction between such medicines and anesthetic agent, which has significant effects even on the success of the ophthalmic surgery. In addition to the possible side effects, chemical anesthesia agents often result in adverse effects when applied to the eye surface such as eye dryness and soreness, which further lead to patient discomfort.

The rapidly increasing number of IVTs has resulted in severe strain in ophthalmic clinic work flow and long patient waiting time, forcing retina specialists to sacrifice patient experience for managing their busy clinics. The trade-offs between the quality and time efficiency of current ocular anesthesia methods as well as the several adverse effects and medical complications of ocular anesthetic agents indicate unmet needs for a non-invasive and time-efficient method for maximal anesthesia.

SUMMARY OF THE DISCLOSURE

The present disclosure or teaching is contemplated to solve the problem in the conventional art. Thus, an object of the present disclosure is to provide a device and a method for delivering cryoanesthesia or cryoanalgesia rapidly and safely.

According to one aspect of the subject matter described in this application, a removable cooling medium for a medical cooling device, the cooling medium may comprise: a first fluid medicine reservoir configured to be installed outside a main body that couples with a medical cooling device and to move into the main body, wherein the first fluid medicine reservoir stores a first fluid medicine to be injected through a hole at a tip of the main body.

Implementations according to this aspect may include one or more of the following features. For example, the first fluid medicine reservoir may include an injecting needle for injecting the first fluid medicine, and the injecting needle may not be in contact with the tip while moving along the hole. Further, in some instances, the first fluid medicine reservoir may include an injector disposed on a central axis of the first reservoir, and the injector may be configured to be moved by an actuator that is operably connected to the injector.

In some implementations, the cooling medium may further comprise a second fluid medicine reservoir configured to store a second fluid medicine and arranged in line with the first fluid medicine reservoir along an axial direction of the main body. At least one of the first fluid medicine or the second fluid medicine may be discharged outside the cooling medium through the hole at the tip. Further, in some instances, the first fluid medicine may comprise a therapeutic agent, and the second fluid medicine may comprise a disinfecting agent.

In some implementations, the cooling medium may further comprise a sealing layer provided between the hole and the first fluid medicine reservoir or between the hole and the second fluid medicine reservoir.

In some implementations, the first or second fluid medicine reservoir may be configured to maintain a temperature of the first fluid medicine or a temperature of the second fluid medicine above freezing points thereof.

In some implementations, the first reservoir may be made of material having thermal conductivity lower than that of the main body. For example, a surface of the main body contacting the first reservoir may have the thermal conductivity of 20 W/m-K or less, and may be maintained 20 mm² or less.

According to another aspect of the subject matter described in this application, a method of cooling a target area comprising: providing a removable cooling medium comprising: a first fluid medicine reservoir configured to be installed outside a main body that couples with a medical cooling device and to move into the main body, wherein the first fluid medicine reservoir stores a first fluid medicine to be injected through a hole at a tip of the main body.

Details of examples or implementations will be described in the following with reference to the accompanying drawings. Other features will be apparent from the description and drawings, and from the claims.

BRIEF DESCRIPTION OF THE DRAWINGS

The present disclosure will become more fully understood from the detailed description given herein below and the accompanying drawings, which are given by illustration only, and thus are not intended to limit the scope of the present application, wherein.

DETAILED DESCRIPTION

Figure 1A:
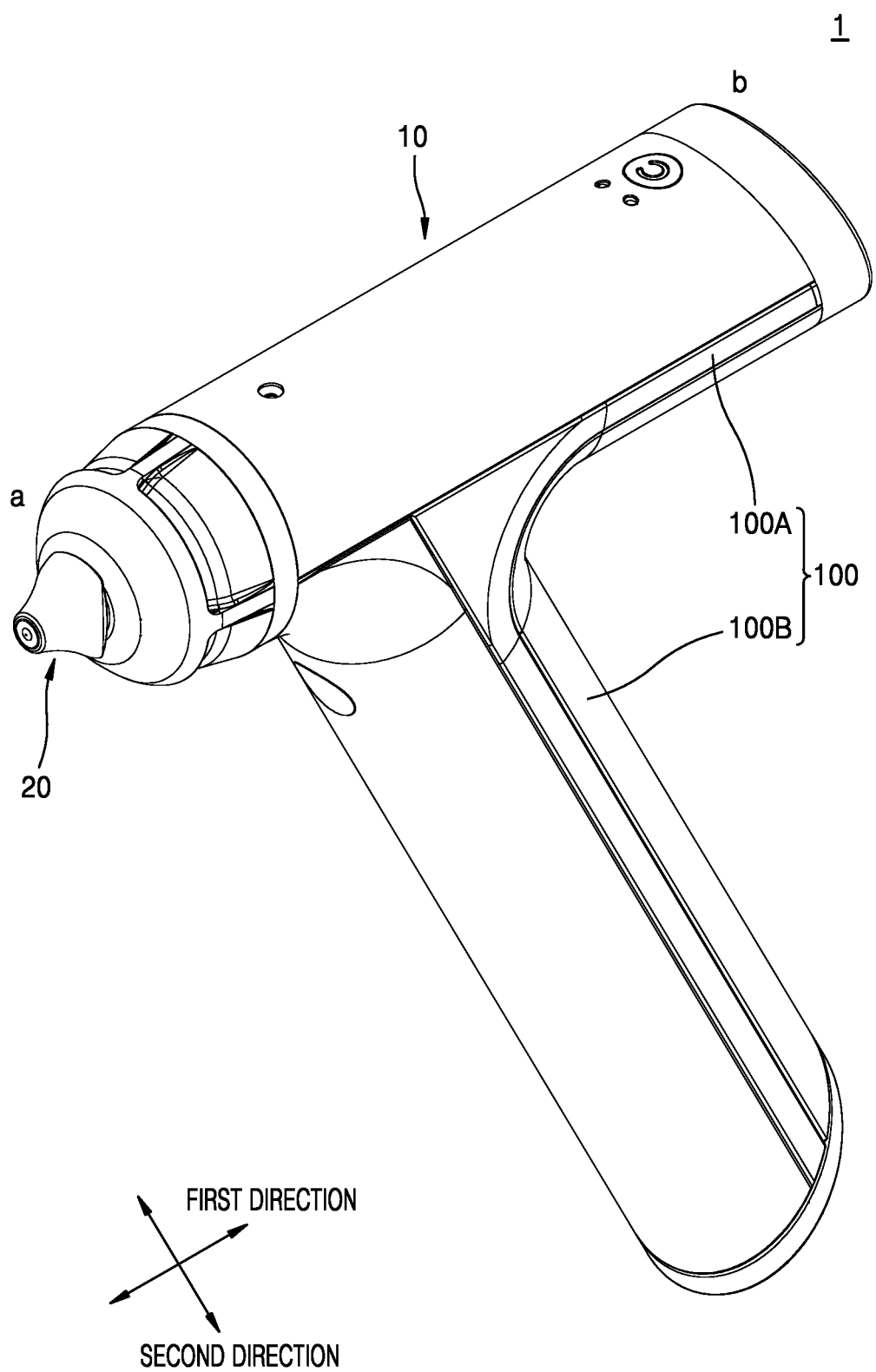
FIGS. 1A to 1H are views illustrating examples of an overall configuration of a medical cooling system or device having a cooling function.

Description will now be given in detail according to examples disclosed herein, with reference to the accompanying drawings. For the sake of brief description with reference to the drawings, the same or equivalent components may be provided with the same reference numbers, and description thereof will not be repeated. In general, a term such as "module" and "unit" may be used to refer to elements or components. Use of such a term herein is merely intended to facilitate description of the specification, and the term itself is not intended to give any special meaning or function. In the present disclosure, that which is well-known to one of ordinary skill in the relevant art has generally been omitted for the sake of brevity. The accompanying drawings are used to help easily understand various technical features and it should be understood that the examples presented herein are not limited by the accompanying drawings. As such, the present disclosure should be construed to extend to any alterations, equivalents and substitutes in addition to those which are particularly set out in the accompanying drawings.

It will be understood that although the terms such as first, second and the like may be used herein to describe various elements, these elements should not be limited by these terms. These terms are generally only used to distinguish one element from another.

It will be understood that when an element is referred to as being "connected with" or "coupled with" another element, the element can be directly connected with the other element or intervening elements may also be present. In contrast, when an element is referred to as being "directly connected with" or "directly coupled with" another element, there are no intervening elements present.

A singular representation may include a plural representation unless it represents a definitely different meaning from the context.

Terms such as "comprise", "include" or "have" are used herein and should be understood that they are intended to indicate an existence of several components, functions or steps, disclosed in the specification, and it is also understood that greater or fewer components, functions, or steps may likewise be utilized. Moreover, due to the same reasons, it is also understood that the present disclosure includes a combination of features, numerals, steps, operations, components, parts and the like partially omitted from the related or involved features, numerals, steps, operations, components and parts described using the aforementioned terms unless deviating from the intentions of the original disclosure.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the disclosure in use or operation in addition to the orientation depicted in the figures. For example, if any element in the figures is turned over, elements described as "below" or "beneath" other elements or features would then be oriented "above" the other elements or features. Thus, the example term "below" can encompass both an orientation of above and below. Such an element may be otherwise oriented (rotated 90 degrees or at other orientations) and the spatially relative descriptors used herein interpreted accordingly.

I. Overall Configuration of Cooling Device

Figure 1B:
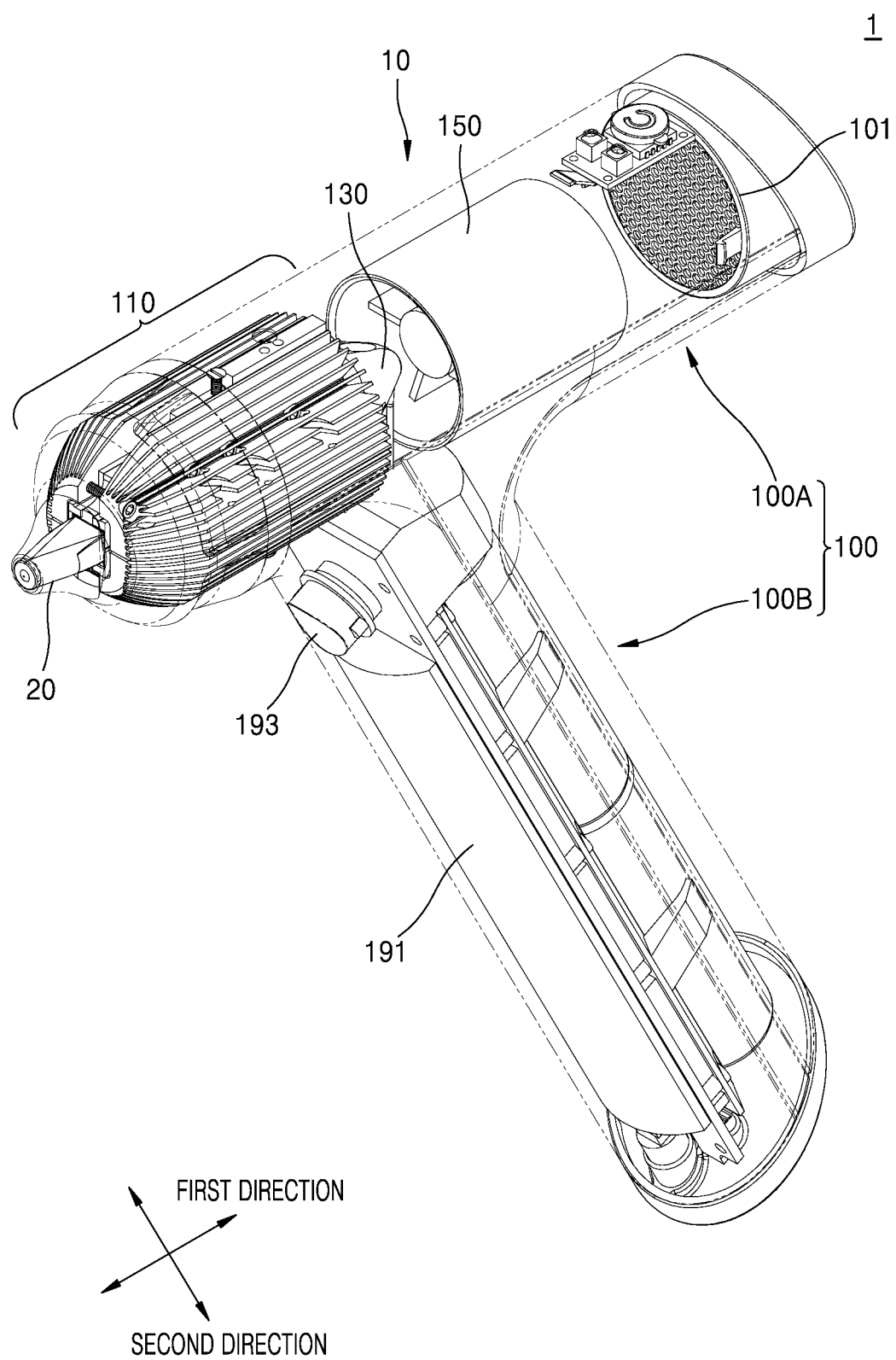
Figure 1C:
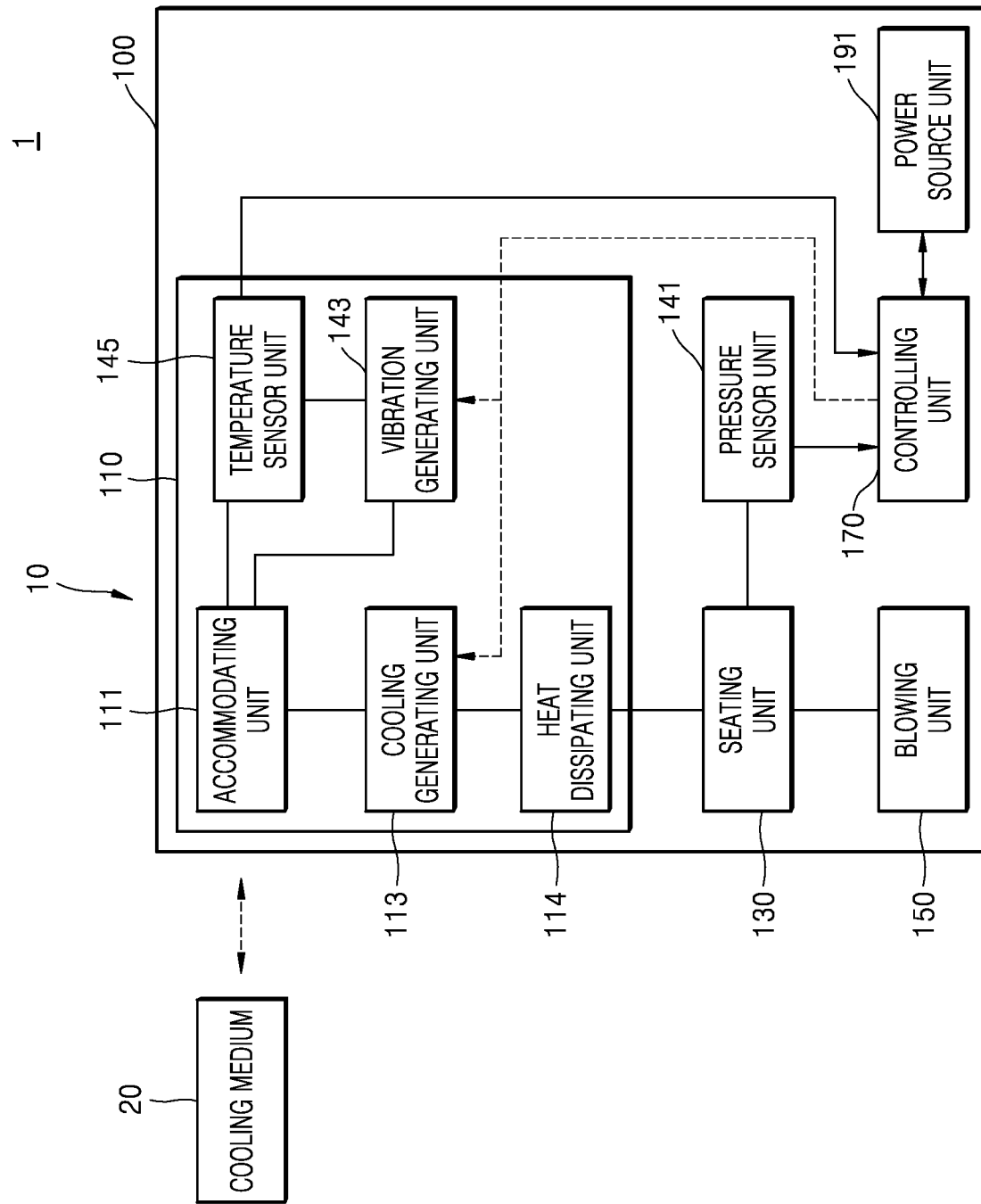

FIGS. 1A to 1C are views showing an example of a medical cooling system having a cooling function. FIG. 1A is a perspective view showing a medical cooling system according to one example of the present disclosure, and FIG. 1B is a perspective view showing an internal configuration of the medical cooling system shown in FIG. 1A. FIG. 1C is a block diagram of the medical cooling system shown in FIG. 1A Hereinafter, a medical cooling system according to examples or implements of the present disclosure will be described with reference to the drawings.

Referring to FIGS. 1A to 1C, a medical cooling system 1 according to an example of the present disclosure may include a medical cooling device 10 and a cooling medium 20 accommodated in the medical cooling device 10. In an alternative aspect of the present disclosure, the medical cooling system 1 may be narrowly defined as a medical cooling device 1. In this case, the medical cooling device 10 may be a body 10 of the medical cooling device 1 as newly defined, which is an assembly of a housing and components disposed in the housing, and the cooling medium 20 may be considered to be one of the components provided to the body 10. That is, according to the alternative definition of the present disclosure, the medical cooling device 1 may comprise the body 10 and the cooling medium 20 provided in the body 10. Although the present disclosure will be mainly described referring to the basic definition of the medical cooling system 1, the medical cooling device 10, and the cooling medium 20, the alternative definition as above is also applicable to the following description for better understanding, if necessary.

The medical cooling system 1 according to the examples of the present disclosure may be configured to cool the cooling medium 20 accommodated in the medical cooling device 10 and then to cool an object thermally coupled to the cooling medium 20, by the operation of the medical cooling device 10. Here, thermal coupling with the object by the cooling medium 20 may include being in indirect contact or non-contact with the object, in additional to being in direct and physical contact with the object. The medical cooling system 1 or device 10 according to the examples of the present disclosure may perform anesthesia by paralyzing nerves of a portion to be treated, i.e., a target portion by cooling such a target portion. In addition, the medical cooling system 1 or device may accommodate a medicine or drug in the cooling medium 20, and at the same time, may adjust a temperature of the medicine or drug independently of a temperature of the cooling medium 20, such that the disinfectant is discharged on or the medicine is injected into the target portion, while the target portion is anesthetized.

In the present disclosure, a portion to be anesthetized using the medical cooling system 1 or device 10 may be any portions of a living body, for example, nerves, skin, eyes, gums, and the like. Hereinafter, the medical cooling system 1 or device 10 will be described with connection with the eye for the convenience of explanation, but the present disclosure is not limited thereto. Further, the portion to be anesthetized may be mainly referred to as a target area, but may also be referred to as a target portion or simply the target for brevity.

In addition, the medical cooling system 1 or device 10 may be applied not only to the anesthesia using cooling, i.e., cryoanesthesia or cryoanalgesia but also to cases where hemostasis is required, antibiosis is required, skin portions such as dots, warts, and corns are removed, and local anesthesia is required for a relatively short time period in a small-scale laser treatment for hair removing, peeling and so forth.

FIGS. 1D to 1H are views for describing features related to a triangular structure body of the medical cooling device.

Figure 1D:
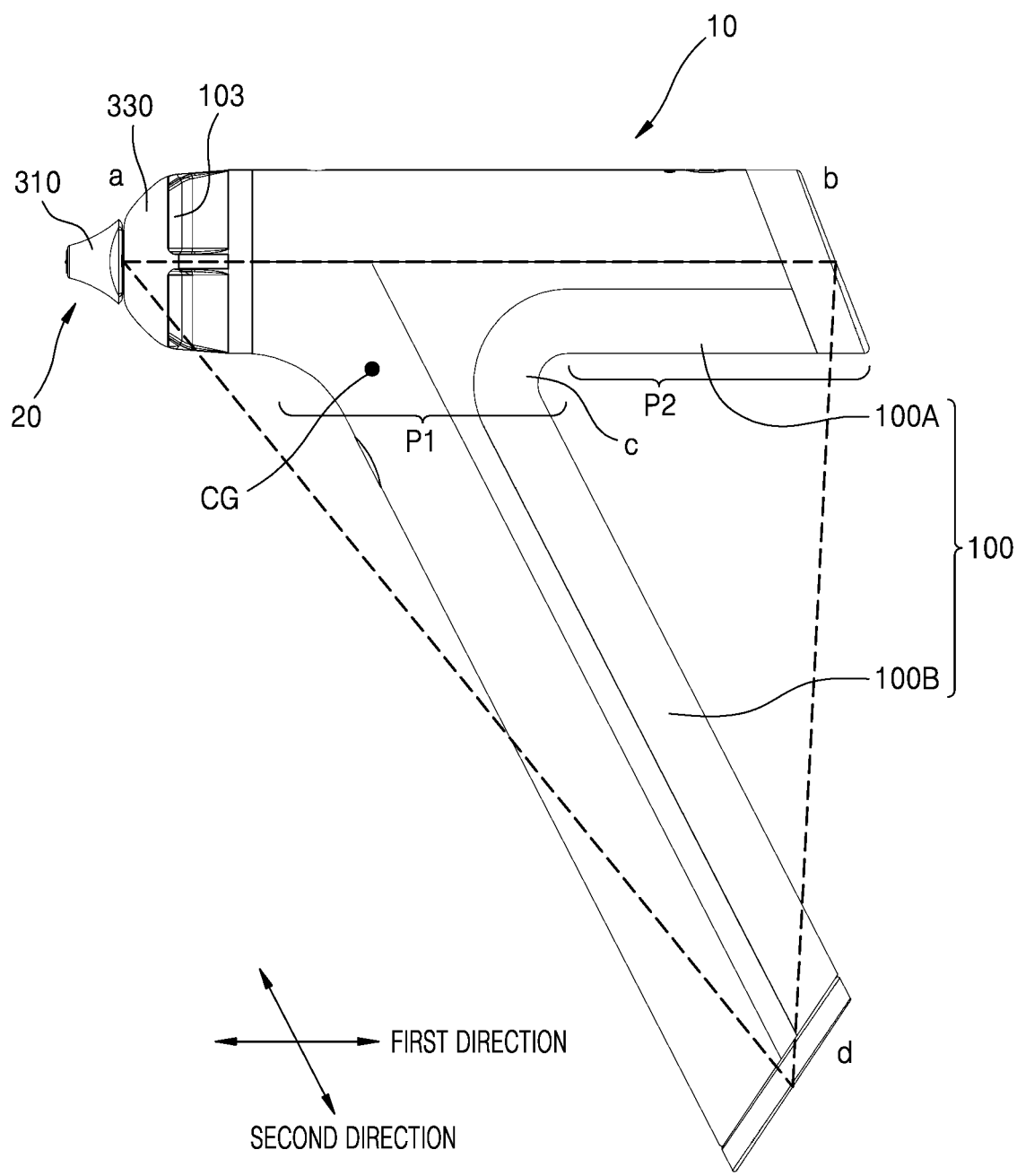
Figure 1E:
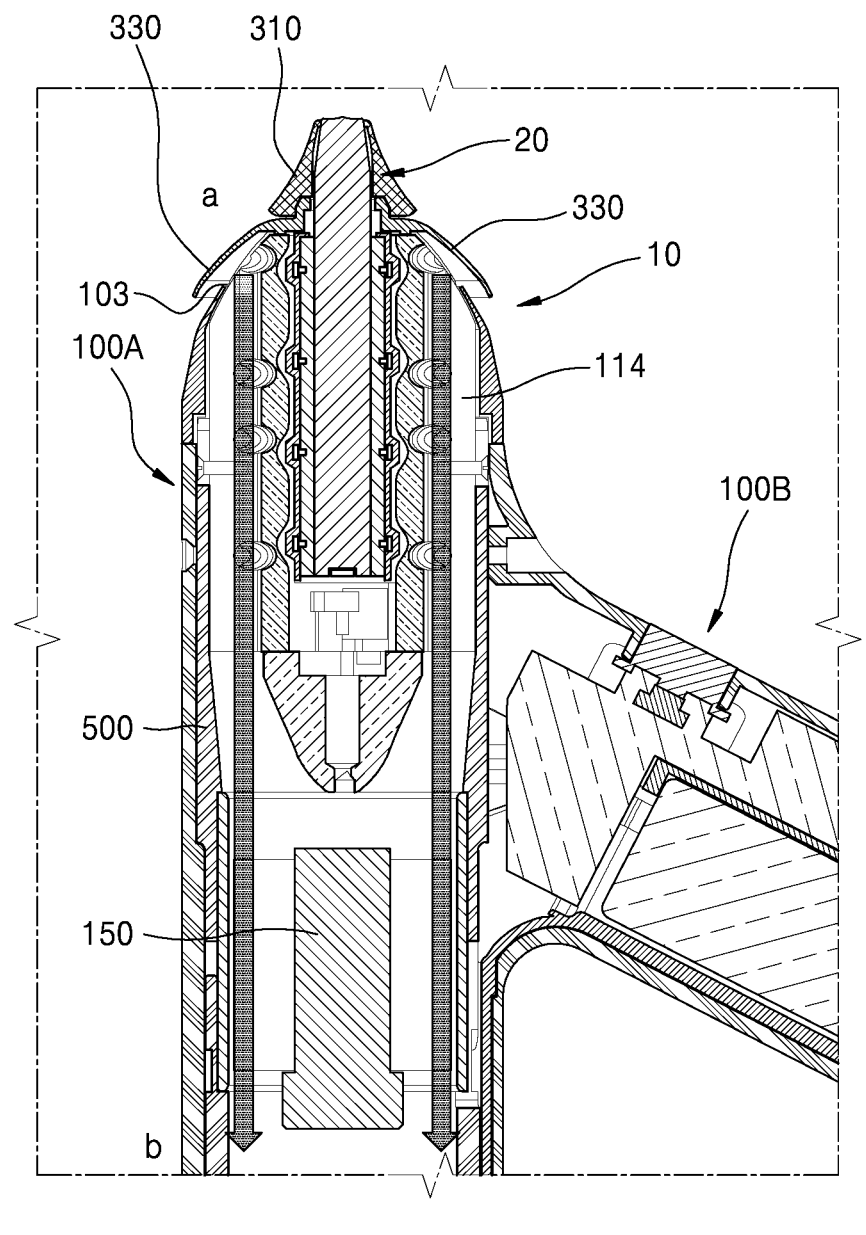
Figure 1F:
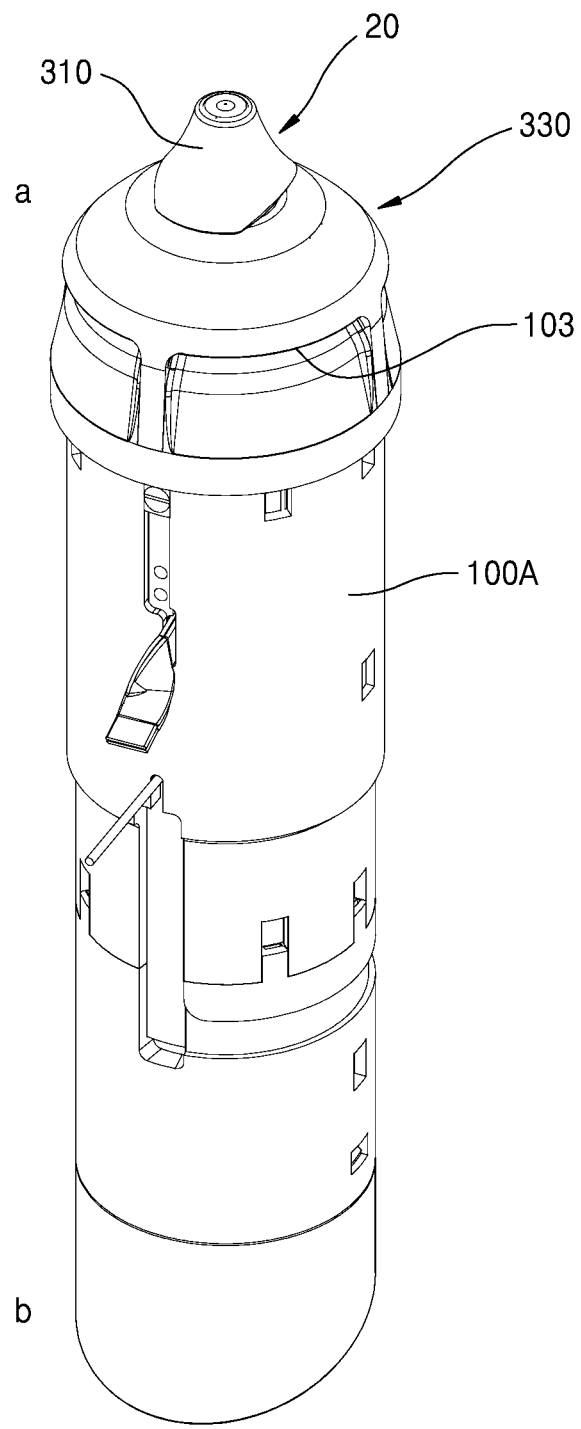
Figure 1G:
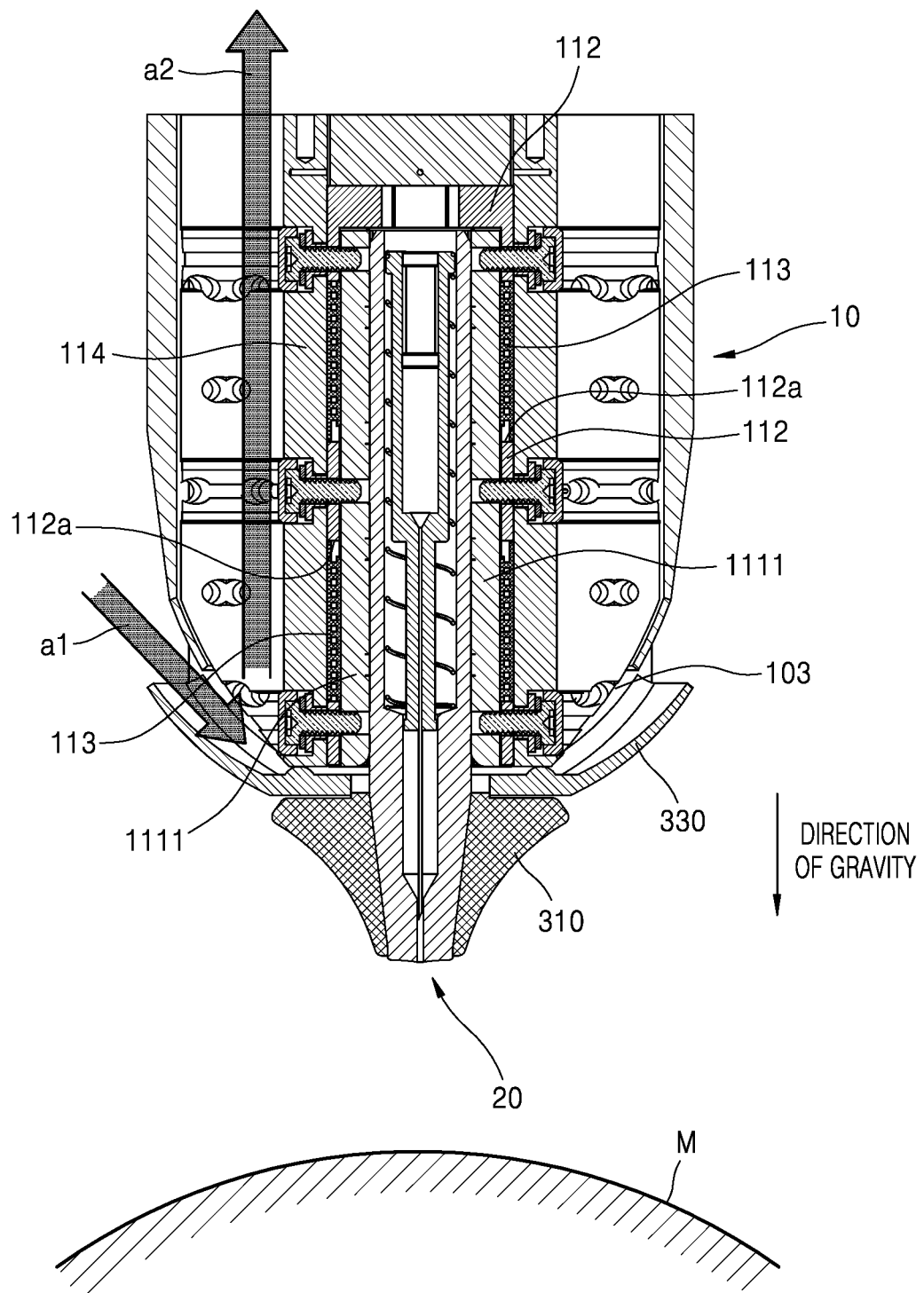
Figure 1H:
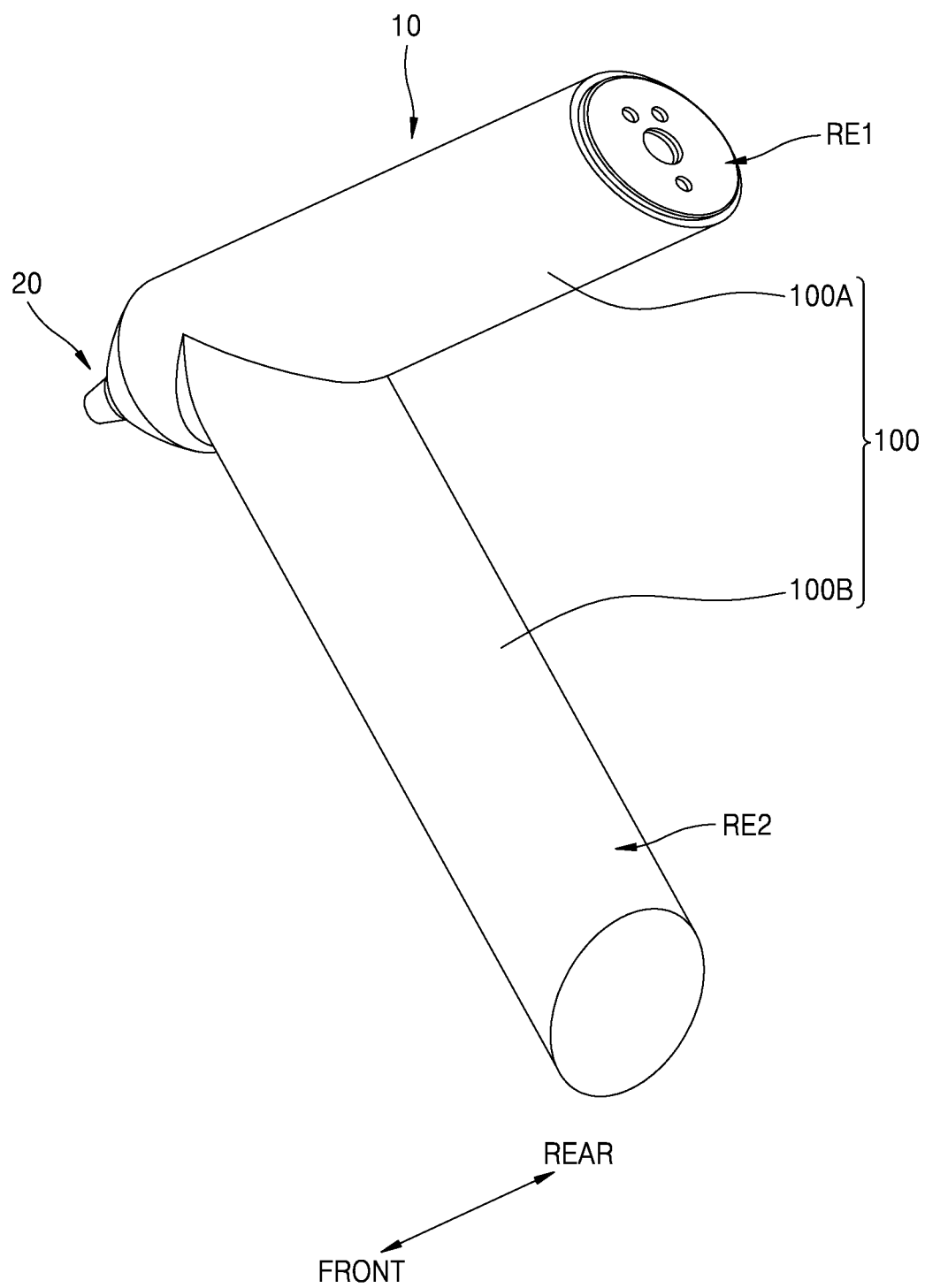

FIG. 1D is a view for explaining a structure of a main body of the medical cooling device according to the example of the present disclosure, and FIGS. 1E and 1F are conceptual views for schematically showing another structure of the medical cooling device of FIG. 1D. FIG. 1G is a conceptual view for explaining air flow in the medical cooling device of FIG. 1D. FIG. 1H is a rear view of the medical cooling device or system. In the present disclosure, the main body may refer to the same configuration as a body of the medical cooling device, according to the basic definition or alternative definition as discussed above.

Referring to FIG. 1D, a main body 100 of the medical cooling device 10 according to the example of the present disclosure may include a first body 100A and a second body 100B. In one example, the main body 100 of the medical cooling device 10 may have a triangular structure. According to a preferred example, the first body 100A may be configured to perform the cooling function and the second body 100B may be configured to perform a power supplying function. In order to increase convenience in use, the main body 100 may not have any additional gripping portion.

The main body 100 of the medical cooling device 10 may have various forms in view of a hand size, habit, and so forth of a user. For this purpose, the triangular structure that may be conveniently used without additional components may be provided to the main body 100. Therefore, in the present disclosure, any grip portion may not be included in the first body 100A or the second body 100B.

Specifically, as shown in FIGS. 1C and 1G, the first body 100A may receive or house a cooling medium accommodating unit 111 therein. Here, the cooling medium accommodating unit 111 may be configured to thermally couple with the cooling medium 20 and to accommodate the cooling medium 20.

The first body 100A may perform a function of cooling the target area through at least one of a first thermal coupling and a second thermal coupling with the target area. Here, the first thermal coupling may include a thermal coupling achieved through contact with the target area, and the second thermal coupling may include a thermal coupling through non-contacting with the target area. More specifically, the first thermal coupling may mean that the medical cooling device 10 directly performs the cooling function by directly contacting the target area. The second thermal coupling may mean that the medical cooling device 10 cools the target area using a coolant or a refrigerant such as liquid nitrogen or carbon dioxide while the medical cooling device 10 is not in direct contact with the target area. That is, the second thermal coupling may be achieved when the medical cooling device 10 is provided with a spay unit (not shown) and sprays to the target area various materials such as the coolant of refrigerant (i.e., liquid nitrogen and carbon dioxide), air cooled at a low temperature and the like, such that the target area is cooled by the sprayed material while the device 10 is not in contact with the target area.

The first body 100A may extend along a first direction which corresponds to a longitudinal direction of the accommodating unit 111 (or the first body 100A) while receiving the accommodating unit 111 therein. In addition, the first body 100A may house a cooling generating unit 113, the heat emitting or dissipating unit 114, and the blowing unit 150 therein. The first body 100A may include a first end portion a disposed adjacent to the cooling medium accommodating unit 111 and second end portion b disposed opposite to the first end portion a. The first body 100A may include an overlapping region P1 which is connected to and overlaps with the second body 100B and a non-overlapping region P2 which does not overlaps with the second body 100B. As shown in the related drawings, the overlapping region P1 may be configured to contact the second body 100B, and thus the overlapping region P1 may be defined as a contact region or portion with the second body 100B while the non-overlapping region P2 may be defined as a non-contact region or portion with the second body 100B. In view of a relative position with regard to the target area, the first end portion a may include a first end facing or being adjacent to the target area and a portion of the first body 100A extending from the first end by a predetermined length toward an opposite end of the first body 100A, i.e., the second end portion b. Likewise, the second end portion b may include a second end farther away than the first end from the target area and a portion of the first body 100A extending from the second end toward the first end portion a by a predetermined length. Alternatively, the first end and the first end portion a may be regarded as a proximal end and a proximal end portion which are close to the target are. In the same manner, the second end and the second end portion b may be regarded as a distal end and a distal end portion.

The second body 100B may be connected to the first body 100A and may extend in a direction (a second direction) different from the direction in which the first body 100A extends (the first direction). The second body 100B may include an overlapping region overlapping with the first body 100A and a non-overlapping region not overlapping with the first body 100A. As shown in the related drawings, the overlapping region of the second body 100B may be configured to contact the first body 100A, and thus the overlapping region of the second body 100B may be defined as a contact region or portion with the first body 100A while the non-overlapping region of the second body 100B may be defined as a non-contact region or portion with the first body 100A. The first body 100A may be a portion for receiving the cooling medium accommodating part 111 to perform the cooling function and the second body 100B may be a handle for the device 10, specifically for the first body 100A. The second body 100B may extend from the first body 100A at a predetermined angle to be inclined with respect to the first body 100A for convenient use. The second body 100B may include a first end portion c connected to the first body 100A and a second end portion d disposed opposite to the first end portion c. In view of a relative position with regard to the first body 100A, the first end portion c may include a first end facing or be adjacent to the first body 100A and a portion of the second body 100B extending form the first end by a predetermined length toward an opposite end of the second body 100B, i.e., the second end portion d. Likewise, the second end portion d may include a second end farther away than the first end from the first body 100A and a portion of the second body 100b extending from the second end toward the first end portion c by a predetermined length. Alternatively, the first end and the first end portion c may be regarded as a proximal end and a proximal end portion which are close to the first body 100A. In the same manner, the second end and the second end portion d may be regarded as a distal end and a distal end portion.

Meanwhile, as shown in FIG. 1B, a power source unit 191 may be disposed in the second body 100B. The power source unit 191 may supply power required for a cooling generating unit 113, a controlling unit 170, a blowing unit 150, and the like. The power source unit 191 may be connected to an external power source or may supply the power through a built-in battery. In view of a configuration as above, the power source unit 191 may be referred to as a power source, a power supply, and the like.

The main body 100 having a configuration described above may form the triangular structure by the first body 100A and the second body 100B. As shown in FIG. 1D, the first end portion a of the first body 100A, the second end portion b of the first body 100A and the second end portion d of the second body 100B may correspond to vertexes of the triangular structure of the main body 100.

A center of gravity CG of the main body 100 may be positioned eccentric toward the first end portion a of the first body 100A. Particularly, as the second body 100B accommodates a heavy component such as the battery therein, the center of gravity CG of the main body 100 may vary depending on a position of the second body 100B. Therefore, by disposing the second body 100B adjacent to the first end portion a of the first body 100A, the center of gravity CG of the main body 100 1 may be located eccentric or adjacent to the first end portion a of the first body 100A.

Further, in some examples, a position of the center of gravity may be optimized according to types of components contained in the first and second bodies 100A and 100B. That is, the position of the center of gravity may be adjusted according to weight of heavy components such as the battery, the cooling medium 20, the heat dissipating unit 114 accommodated in the first and second bodies 100A and 100B.

The first direction in which the first body 100A extends and the second direction in which the second body 100B extends may cross in the overlapping region P1 of the first body 100A, and the overlapping region P1 may be disposed closer to the center of gravity CG than the non-overlapping region P2. That is, a center of gravity region of the main body 100 may be formed within the overlapping region P1 of the first body 100A. The first end portion a of the first body 100A may be a portion in which the cooling medium 20 is disposed to perform the cooling function, and thus the cooling medium 20 may stably contact and cool the target area due to the configuration regarding the center of gravity as discussed above, especially the center of gravity eccentric or adjacent toward the first end portion a.

In addition, the overlapping region P1 may include a center of gravity of only the first body 100A instead of the center of gravity of the entire device 10 (i.e., the first and second bodies 100A and 100B). Since the center of gravity of the first body 100A itself is included in the overlapping region P1 as described above, the momentum occurred during manipulation of the first body 100A with the gripping second body part 100B is minimized. The weights of both the first body 100A and the second body 100B represent a significant portion of the weight of the entire device 10, and the coupling of the first body 100A and the second body part 100B may be mechanically strong and stable in order to ensure mechanical integrity to the entire device 10.

Referring to FIG. 1E, the medical cooling device 10 according to the example of the present disclosure may further include an inner case 500 mounted inside the first body 100A.

The inner case 500 may be a member disposed in the first body 100A, and may be arranged to surround an outer periphery of the heat dissipating unit 114 while being spaced apart therefrom by a minimum distance. The inner case 500 may extend in the longitudinal direction of the first body 100A to cover the heat dissipating unit 114 and the blowing unit 150, i.e. a fan or a blower. The inner case 500 may form an air flow path that communicates with the first end portion a where an end of the heat dissipating unit 114 is located and the second end portion b, respectively. As the inner case 500 may have a closed structure connecting the first and second end portions a and b of the first body 100A while maintaining a minimum distance from the heat dissipating unit 114, the inner case 500 may function as a duct which guides all air flow to pass through the heat dissipating unit 114.

The inner case 500 may be configured to be detachable from the first body 100A and may be attached to or detached from the medical cooling device 10 as required. The inner case 500 may be disposed inside the medical cooling device 10 such that the airflow may be linearly formed from the first end portion a to the second end portion b of the first body 100A, as shown in FIG. 1E.

According to the configuration of the present disclosure, the medical cooling device 10 may have the separate inner case 500 capable of generating the concentrated air flow, thereby providing such air flow to the heat dissipating unit 114. Further, in the present disclosure, the air flow path requiring a complex shape may be integrally formed at the inner case such that an outer case of the device 10 may be simplified and an assembling process thereof may be made efficient.

Referring to FIG. 1F, as another example of the medical cooling device 10 shown in FIG. 1E, the first body 100A itself may be formed to concentrate the air flow therein. The first body 100A may include an outer surface and an inner surface opposed to the outer surface, and the inner surface of the first body 100A may be formed to have an air flow path between the first and second end portions a and b, through which the air flow passes through the heat radiating part 114. While the inner case 500 of FIG. 1E may be a member or structure separable from the first body 100A, the first body 100A of FIG. 1F itself may be configured to force all the airflow in the first body 100A to pass through the heat dissipating unit 114. For this purpose, a structure like the inner case 500 may be formed as a one body with the inner surface of the first body 100A.

Further, a filter (not shown) may be installed at an inlet located at the first end portion a and/or at an outlet located at the second end portion b of the first body 100A to protect the internal structures and components from external contaminants such as dust.

Referring to FIGS. 1D, 1E and 1G, the medical cooling system 1 may further include a guide member 330 installed to the first end portion a of the medical cooling device 10.

The guide member 330 may be disposed at the first end portion a of the first body 100A and may cover the main body 100 and the components therein. The guide member 330 may serve as a protective air flow director that may protect foreign material from entering in the device 10 and may also guide outer air to flow into the device 10. In one example, the guide member 330 may be configured to be included in the first body 100A, and may be configured to be formed separately from a mounter 310 of the cooling medium 20. Particularly, the guide member 330 may be formed integrally with the first body 100A or may be coupled to the first body 100A as a separate member. However, the present disclosure is not limited thereto, and the guide member 330 may be integrated with the mounter 310 of the cooling medium 20 to be installed to the first body 100A together, to enlarge the disposable portion of the entire device 10.

The mounter 310 may be integrally formed with the cooling medium 20 and may have a shape to be easily held by the user, such that installing the cooling medium 20 to the first body 100A may be facilitated.

The mounter 310 may be made of a material having low thermal conductivity such as plastic to minimize loss of cooling power toward an outside of the cooling medium 20. The thickness of the mounter 310 is to be chosen such as a thickness larger than 0.5 mm or the mounter 310 may contain an inner empty space, in order to ensure adequate thermal insulation of the cooling medium 20.

The mounter 310 may closely contact the cooling medium 20 and the medical cooling device 10, and thus the air flow within or outside the first body 100A may not reach the cooling medium 20 to reduce the loss of the cooling power. The mounter 310 may mechanically couple with the medical cooling device 10 with, but not limited to, a snap joint, a magnet, or thread. The mounter 310 may further provide extended region of disposable portion adjacent to the cooling medium 20.

The mounter 310 may provide a surface easily gripped by the user when the cooling medium 20 is inserted into the medical cooling device 10 such that the user may install the cooling medium 20 in the medical cooling device 10 without holding any surface or portion of the cooling medium 20 to be in contact with the target area M. A protective film for sealing may be provided on the surface or the portion of the cooling medium 20 that contacts the target area M, for a hygienic reason. The protective film may be removed after the insertion of the cooling medium 20.

The guide member 330 may be disposed along an outer periphery or circumference of the mounter 310 and may extend radially from the outer periphery or circumference thereof. An inlet 103 may be formed at the first end portion a, and an inner space of the first body 100A may communicate with the outside of the device 10 via the inlet 103. The guide member 330 may be configured to be spaced apart from the first body 100A and the inlet 103 formed thereon to form a space allowing the air to smoothly flow into the first body 100A. An outside air a1 may be sucked into the medical cooling device 10 through the inlet 103 and then the sucked outside air a1 may be discharged to the outside of the first body 100A after passing through an inner space of the first body 100A. Further, as the guide member 330 extending radially covers the inlet 103, the air flow within the first body 100A may be prevented from being flowing back from the 103 and travelling toward the target area. Therefore, by facilitating the air flow into the first body 100A and preventing any back flow from the first body 100A, the guide member 330 may minimize the air flow near the target area M, for example, an eyeball surface. In other words, the guide member 330 may prevent the air from flowing from the device 10 to the patient's eyes, thereby reducing the risk of eye dryness, endophthalmitis, and the like. Further, the guide member 330 may prevent foreign substances from entering the medical cooling device 10 through the inlet 103 and may minimize cooling energy loss due to the airflow generated around the cooling medium 20, i.e., the heat transfer from the cooling medium 20 to such air flow. That is, during the anesthesia, the risk caused by the foreign substances or bacteria that may be transmitted from the air flow to the patient's eye may be minimized, and the foreign matter introduced into the device 10 may be also minimized to reduce the risk of the device malfunction.

Here, the guide member 330 may adjust a flowing angle of the air in the vicinity of the target area M to be 0° to 120° with regard to a vertical direction to the patient's target area, i.e. the eye surface.

In addition, by the guide member 330, any inlet or outlet of the air may be spaced way from the target area M by at least 15 mm. Further, with such a guide member 330, a direction of the sucked air a1 may have an angle of 0° to 120° with regard to a direction of the discharged air a2.

Meanwhile, the airflow guided by the guide member 330, passing through the inside of the first body 100A and finally discharged outside the first body 100A may be formed by the blowing unit 150 in the first body 100A. However, such air flow may be formed not only by the blowing unit 150 (i.e., active air flow), but also by difference in specific gravity of the air that caused by difference in temperature of the air (passive air flow).

Generally, the cooling device 10 may be manipulated with a predetermined angle with regard to the ground or the target area. In this case, the air in the device 10 may be heated by the components therein and thus a temperature of such heated air may be higher than a surrounding air temperature. Further, the heated air may move upward, i.e. in the direction opposite to the gravity or in a direction vertical to the ground due to the difference of the specific gravity and may exit outside the device 10. Such airflow by the specific gravity difference (i.e., the passive airflow) may be generated in substantially the same direction as the air flow generated by the blowing unit 150 (i.e., the active air flow) and may act the additional force to discharge the air in the device, while the cooling device 10 has a posture inclined with regard to the ground during use. Further, as shown in FIGS. 1E and 1G, an internal path for the discharged air a2 may be formed straight to reduce any resistance for the air flow within the device 10. Therefore, with such a configuration, the air in the device 10 may be discharged effectively and efficiently, and thus performance of the cooling device 10 may be enhance by properly dissipating the heat generated by the components.

Further, the mounter 310 or the guide member 330 may serve as an optical injection site guider. That is, at least portion of the mounter 310 and/or the guide member 330 may be made of transparent material or material having a high reflectance such that the target area M may be easily seen by the user. Moreover, the mounter 310 and/or the guide member 330 may be entirely made of the transparent material, or an entire outer surface thereof may be made of the material having the high reflectance. With such mounter 310 and the guide member 330, the user may easily monitor the target area M using refractive or reflective characteristics of the mounter 310 and the guide member 330.

Meanwhile, referring to FIG. 1H, the medical cooling device 10 may further include a control button (not shown) for allowing the user to control the device 10 or/and a display unit (not shown) for allowing the user to monitor a status of the device 10.

The control button and/or the display unit may be disposed at a rear portion of the medical cooling device 10. For example, the medical cooling apparatus 10 may include a control button (not shown) and/or a display unit (not shown) on a rear portion (or surface) RE1 of the first body 100A or a rear surface (or portion) RE2 of the second body part 100B. Alternatively, the medical cooling device 10 may be provided with a control button (not shown) and/or a display unit (not shown) disposed at a position of the body 100 that the user may recognize directly and instantly when looking at the device 10 from the rear. Accordingly, the user may operate the device 10 using the control button disposed on the rear portion or surface even when the device 10 is being precooled before use, and may monitor a status of precooling through the display unit. Further, the user may be guided to grip the device 10 such that the tip of the cooling medium 20 (i.e., the first and front end portion a) is directed downward, while monitoring and controlling the device 10 using the control button and the display unit disposed at the rear portion thereof. With such a configuration, the device 10, particularly the body 100 thereof may be configured to guide the first end portion a to be directed downward. More specifically, the components of the device 10, for example, the components for controlling/manipulating and/or monitoring the device 10 may be located to guide the first end portion a to be directed downward. Therefore, as described above, with such a guided posture of the device 10, the passive air flow by the gravity may be formed and the cooling efficiency may be improved.

II. Cooling Unit

Figure 2A:
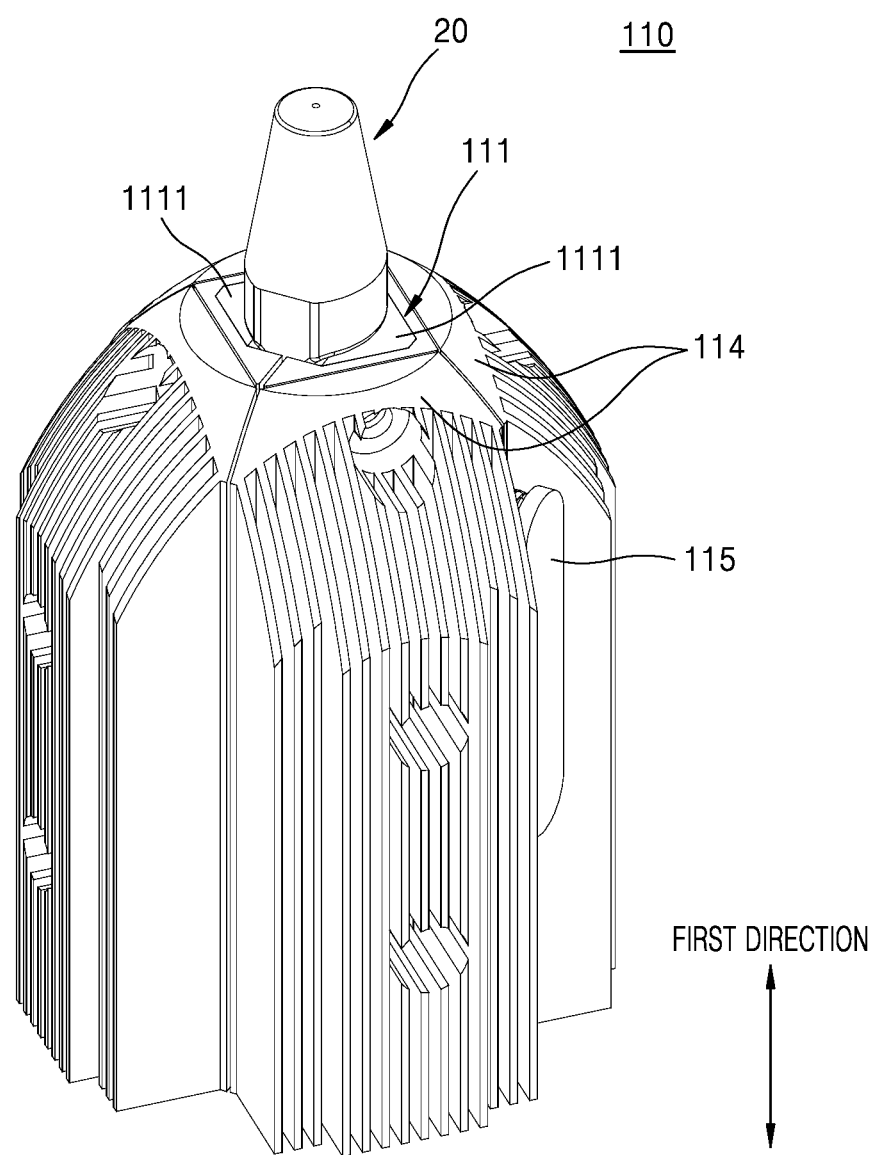
FIGS. 2A to 2K are views illustrating examples of an accommodating unit and a divided member of the medical cooling device.
Figure 2B:
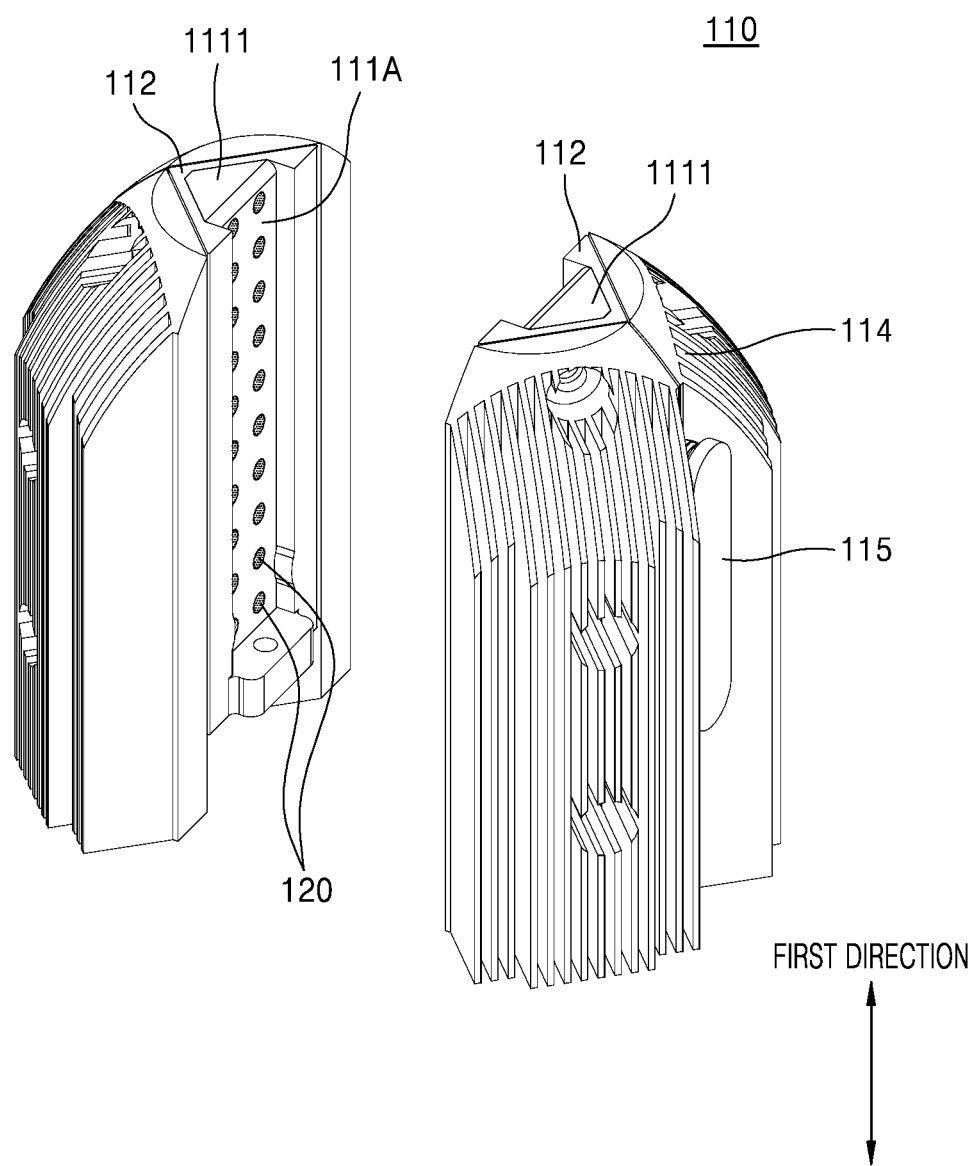
Figure 2C:
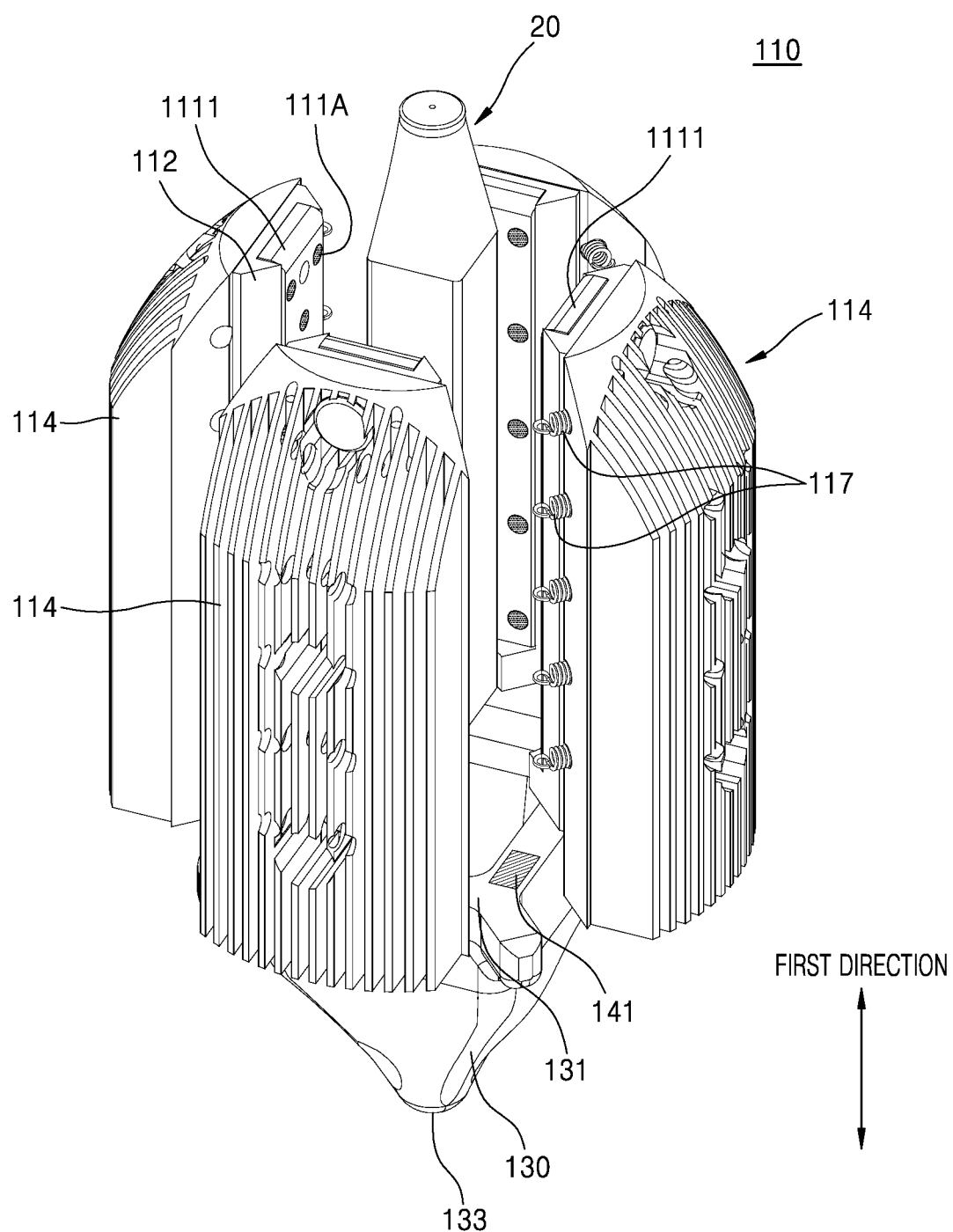
Figure 2D:
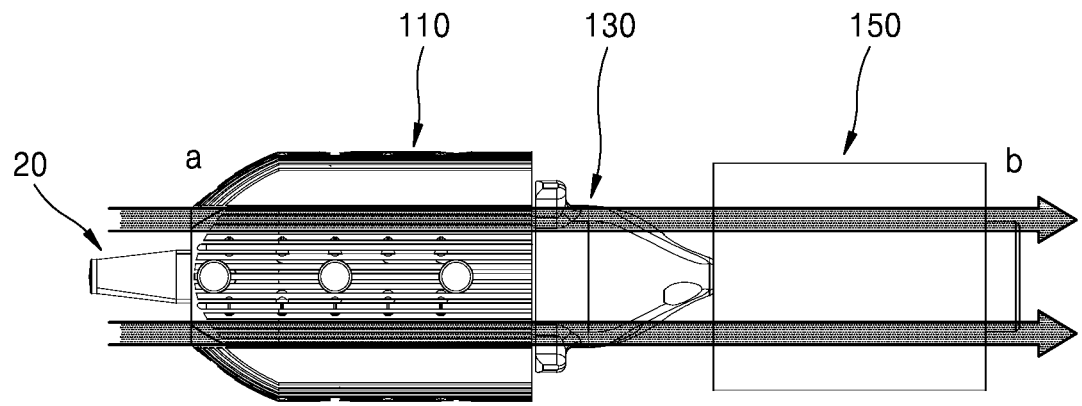
Figure 2E:
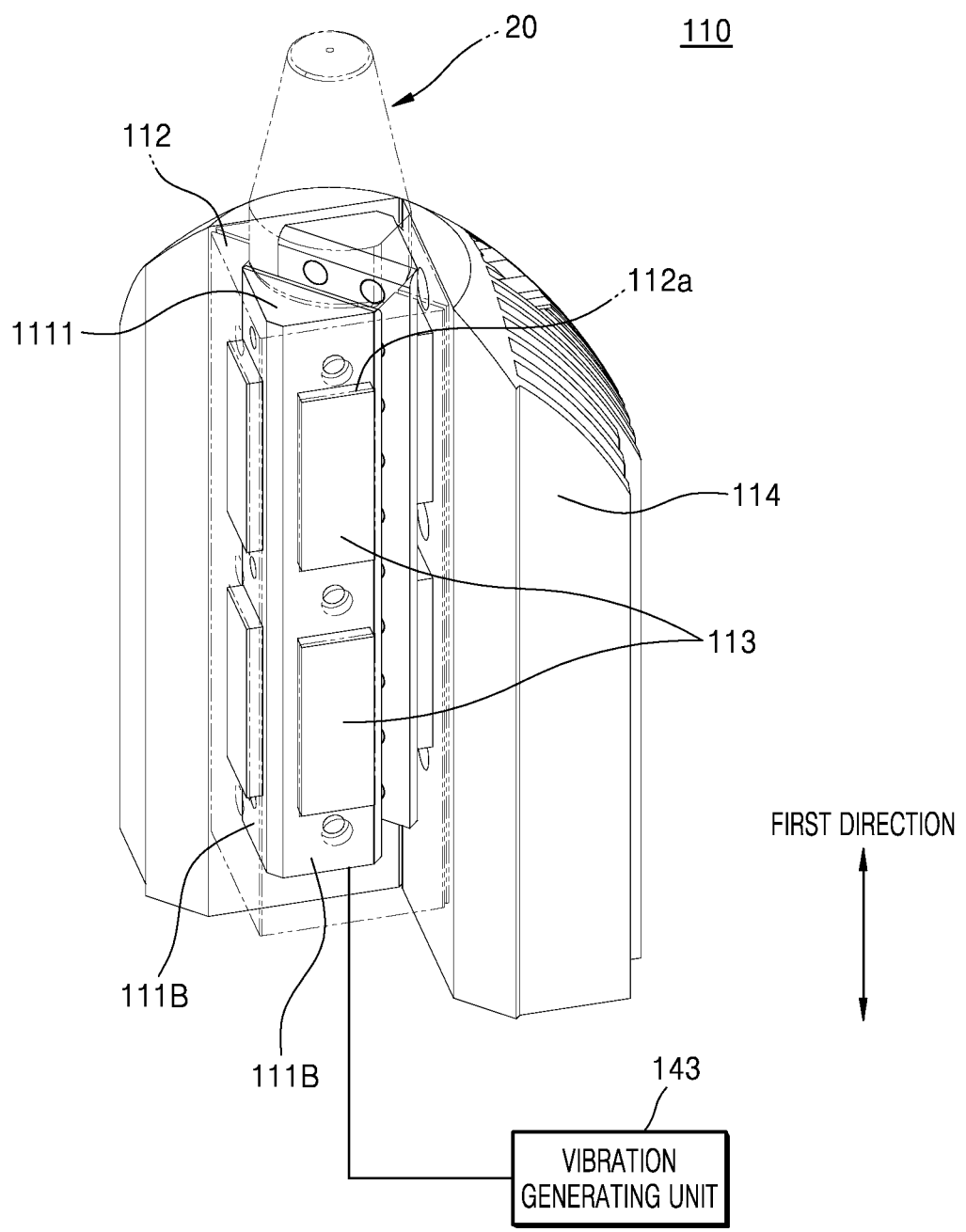
Figure 2F:
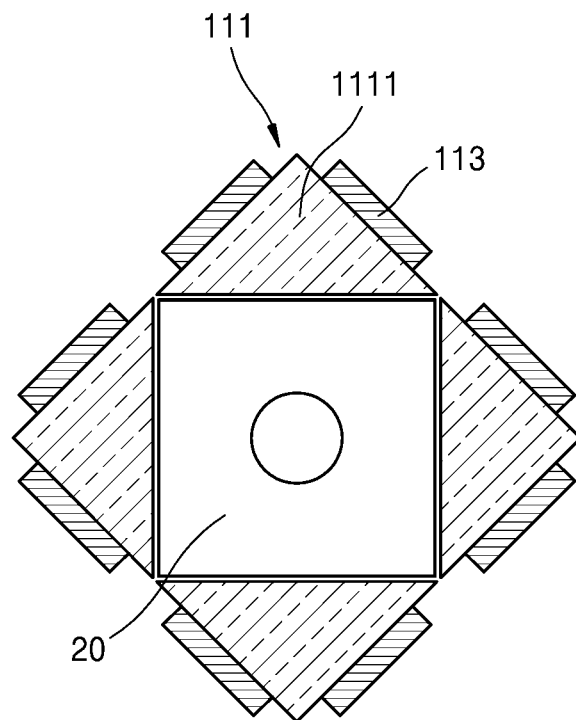
Figure 2G:
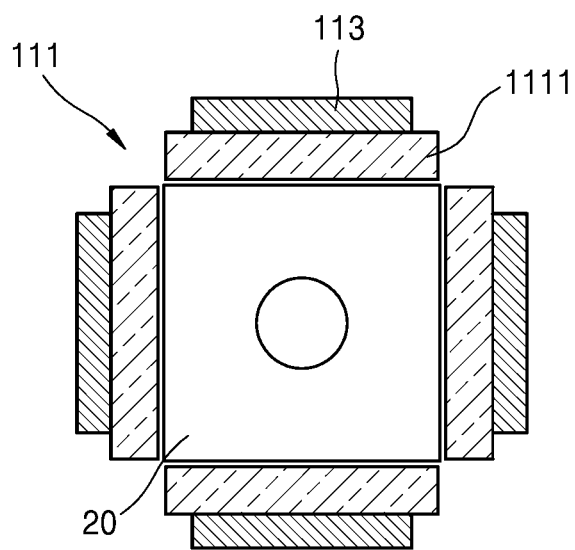
Figure 2H:
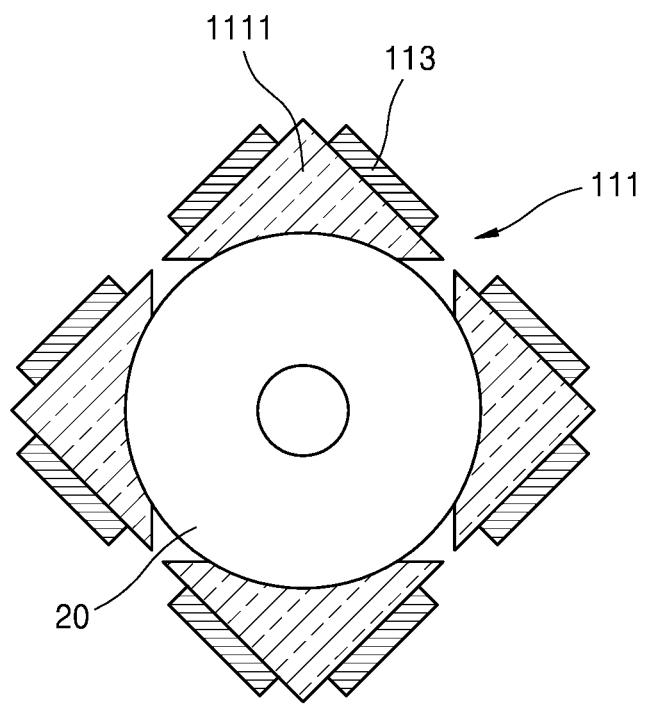
Figure 2I:
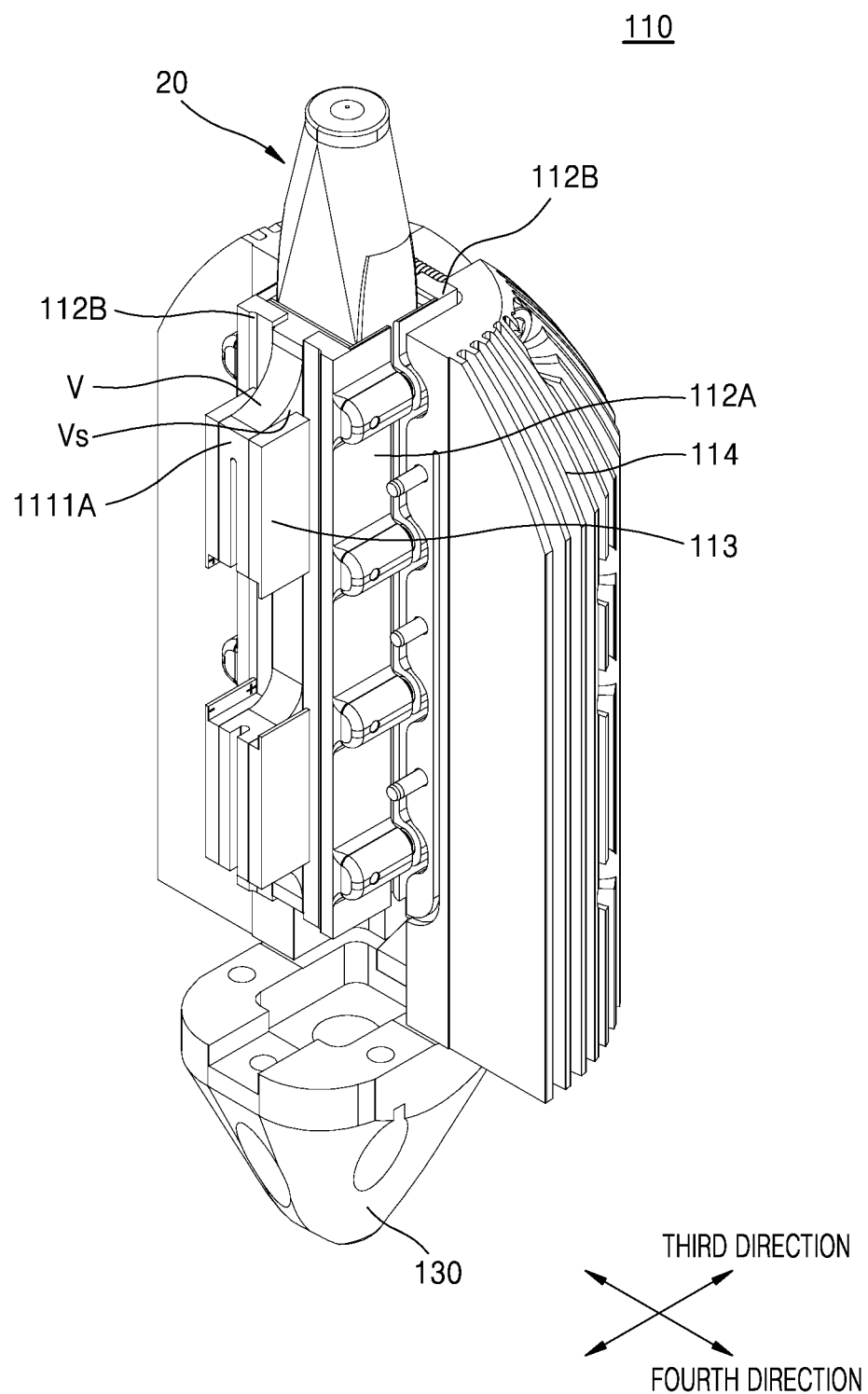
Figure 2J:
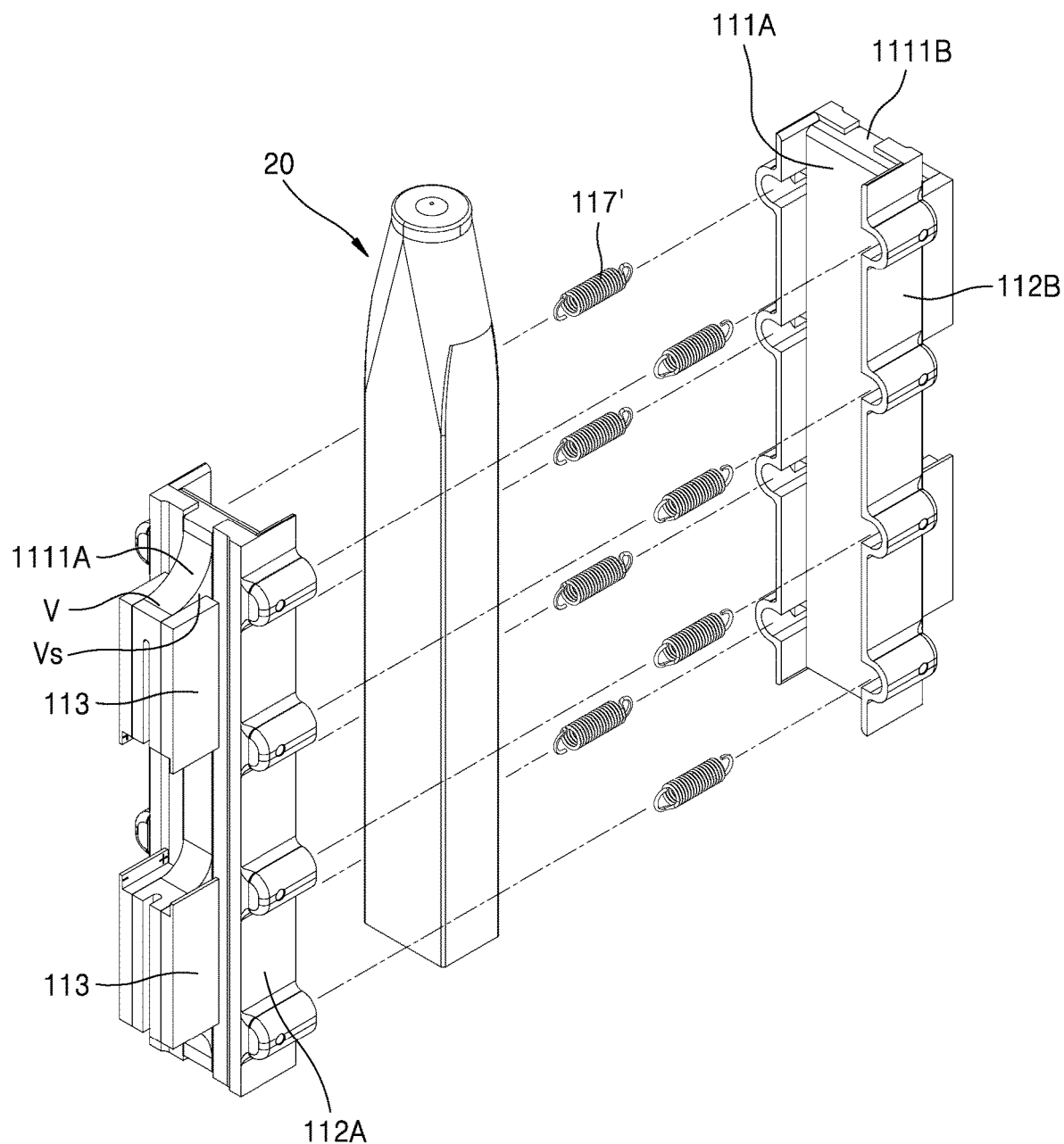
Figure 2K:
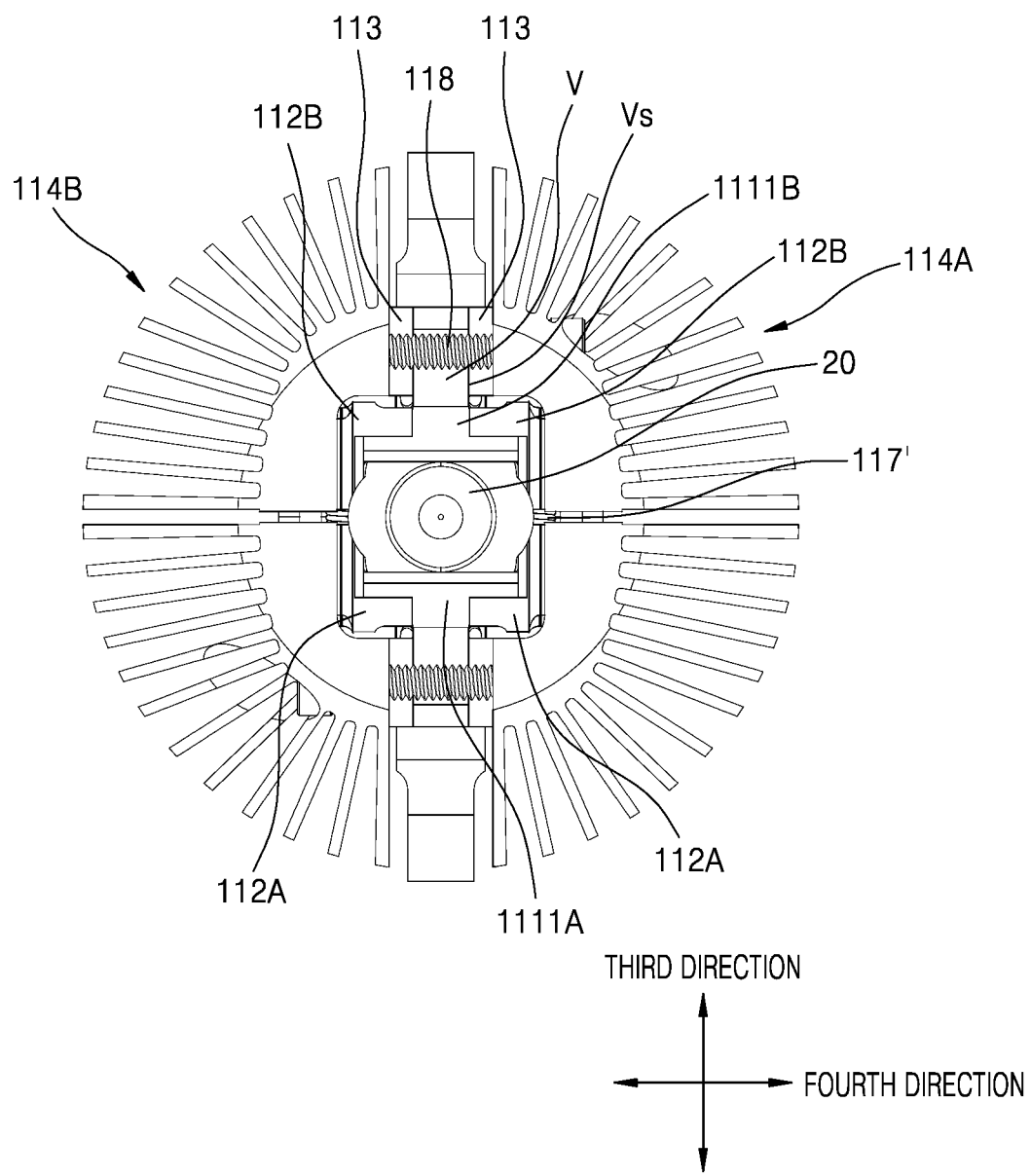

FIGS. 2A to 2H are views for explaining features related to a divided member of the medical cooling device, and FIGS. 2I to 2K are views for explaining features related to a coupling structure, i.e., an orthogonal coupling of the medical cooling device. FIGS. 3A to 3D are views for explaining features related to a lubricating member of the medical cooling device. Hereinafter, the divided member, the coupling structure and the lubricating member will be described with reference to the drawings.

FIG. 2A is a perspective view showing a cooling unit when the cooling medium is inserted into the medical cooling device of FIG. 1A, and FIG. 2B is a partial perspective view showing a cooling unit of FIG. 2A. FIG. 2C is an exploded perspective view of the cooling unit of FIG. 2A. FIG. 2D is a view including some of the components to illustrate air flow in the medical cooling device of FIG. 1A. FIG. 2E is a partial perspective view showing the cooling unit of FIG. 2A from which some components are removed. FIGS. 2F to 2H are sectional views showing the cooling unit of FIG. 2A in various examples.

Referring to FIGS. 1B, 1C, and 2A-2H, the medical cooling device 10 according to one example of the present disclosure may include the body 100, the cooling medium accommodating unit 111, the cooling generating unit 113, the heat dissipating unit 114, the blowing unit 150, a lubricating member 120, and the power source unit 191, most of which are already briefly discussed in Section I. As shown in FIG. 1C, among the components of the cooling device 10, the components 111-114 forming an engine for generating the cooling power may be specifically defined as a cooling unit 110, and such a cooling unit 110 is shown in FIGS. 2A-2K in detail. The body 100 is the same as the main body 100 described above, and hereinafter will be simply referred to as the body 100 for convenience of explanation.

The body 100 may form an exterior of the medical cooling device 10, and the components may be housed therein. The body 100 may include an opening formed at one side thereof such that a portion of the cooling medium 20 accommodated in the medical cooling device 10 may be exposed to the outside of the device 10. According to a preferred example of the present disclosure, the body 100 may has the triangular structure which does not include the additional grip portion. However, the present disclosure is not limited to such a triangular structure, and the body 100 may be formed in the various structures that may be easily used by the user and may be effective for the anesthesia and the injection of the medicine. For example, the body 100 may be configured to have the same grip portion as a pen, an instrument for writing has such that the user may grip the body 100 as if holding the pen.

The cooling medium accommodating unit 111 (hereinafter, referred to as "accommodating unit") may accommodate the cooling medium 20 and may be thermally coupled with the cooling medium 20 to transfer the cooling energy or power from the cooling generating unit 113 to the cooling medium 20. The accommodating unit 111 may be made of metallic material having a high thermal conductivity to efficiently transfer the cooling energy. The accommodating unit 111 may function as a cooling distributor for dispersing or distributing over a large surface or area of the cooling medium 20, the cooling energy collected from a relatively small surface or area of the cooling generating unit 113. For this purpose, the accommodating unit 111 may extend along the cooling medium 20 and thus may be in contact with an entire surface of the cooling medium 20 that the accommodating unit 111 faces. With such a cooling distributing function, the cooling energy generated by the cooling generating unit 113 may be efficiently transferred to the cooling medium 20. Further, in view of a structural aspect thereof, the accommodating unit 111 may be referred to as a container for the cooling medium 20. Meanwhile, the cooling medium 20 receives or collects the cooling power distributed by the accommodating unit 111. The cooling medium 20 may be further configured to concentrate the collected cooling power on the target area for the rapid cooling. Thus, the cooling medium 20 may be referred to as a receiver, a collector or a concentrator.

The accommodating unit 111 may comprises a plurality of divided members or partitioned members 1111 having a contact surface 111A that thermally engages with the cooling medium 20. The divided members 1111 may be referred to as contact members or sections, in view of the configuration thereof. The accommodating unit 111 may form a space for accommodating the cooling medium 20 by coupling the plurality of divided members 1111 to be spaced apart from each other. The cooling medium 20 may be accommodated in the formed space and may be cooled by the thermal coupling with the contact surfaces 111A of the plurality of divided members 1111. The contact surface 111A may extend along the longitudinal direction (i.e., the first direction) of the accommodating unit 111. Further, each contact surface 111A may entirely contact the corresponding surface of the cooling medium 20 for more efficient heat transfer from the cooling generating unit 113.

In one example as shown in FIG. 2A, the accommodating unit 111 may comprise two divided members 1111, and these two divided members 1111 are oppositely disposed to form the space for the cooling medium 20. In another example as shown in FIG. 2C, the accommodating unit 111 may comprises four divided members to form the space for receiving the cooling medium 20. However, the present disclosure is not limited to these examples, and it should be understood that the accommodating unit 111 may include various numbers of the divided members 1111 to form various shapes of the spaces for the cooling medium 20.

Although the contact surface 111A is shown as being planar in the drawings, the present disclosure is not limited thereto. The contact surface 111A may have a various shape, for example, a curved shape that efficiently performs heat transfer between the accommodating unit 111 and the cooling medium 20 and minimizes friction therebetween. The contact surface 111A may be formed in a shape corresponding to a shape of the cooling medium 20. As shown in FIG. 2F or 2G, when the cross section of the cooling medium 20 has a rectangular shape, the contact surface 111A of the divided members 1111 may be in a planar shape corresponding thereto. As shown in FIG. 2H, when the cross section of the cooling medium 20 is circular, the contact surface 111A of the divided members 1111 may be a curved surface having a curvature corresponding thereto.

Referring to FIG. 2C, the plurality of divided members 1111 may be connected to one another by the first elastic member or mechanism 117. This first elastic member 117 may be also referred to as a first elastic unit or a first connector, in view of a configuration thereof. The first elastic member 117 may connect the plurality of divided members 1111 for thermal coupling between the cooling medium 20 and the contact surface 111A. In addition, the first elastic member 117 may achieve mechanical and physical coupling between the cooling medium 20 and the contact surface 111A. The first elastic member 117 may provide elastic force between the plurality of divided members 1111 while connecting the divided members 1111. Therefore, the divided members 1111 may be pulled toward one another. Simultaneously, the connected divided members 1111 may be placed closer by the provided elastic force and thus may be relatively pushed against the cooling medium 20. For these reasons, the divided members 1111 may be firmly coupled to one another and the cooling medium 20 may be stably fixed in the space formed by the divided members 1111. The first elastic member 117 may be any mechanism capable of providing the elastic force. For example, the first elastic member 117 may comprise a spring or may comprise a tube made of elastic material that contact and surrounds the accommodating unit 111. Further, when the heat dissipating unit 114 is disposed on the accommodating unit 111, such a first elastic member 117 comprising the elastic tube may surround the heat dissipating unit 114. When the first elastic member 117 is the elastic tube, such an elastic tube may be made of thermally insulating materials such as soft or flexible plastic material to further insulate the accommodating unite 111.

The first elastic member 117 may not be applied to the plurality of divided members 1111 but may be applied to a coupling unit 112 or the heat dissipating unit 114, which may be divided into a plurality of members like the divided members of 1111 of the accommodating unit 111. The plurality of divided members 1111 may be coupled to the plurality of heat dissipating units 114 by the coupling units 112. As shown in FIG. 2C, the heat dissipating units 114 and the coupling units 112 may be divided into the number of members that corresponds to the number of the divided members 1111. Therefore, the first elastic member 117 may connect the plurality of divided members 1111 by coupling the coupling units 112 or the heat dissipating units 114.

As well shown in FIGS. 1G and 2E, the coupling unit (or the coupler) 112 may be interposed between the accommodating unit 111 and the heat dissipating unit 114. The cooling generating unit 113 may be disposed within the coupling unit 112 while directly contacting the accommodating unit 111 and the heat dissipating unit 114. The coupling unit 112 may have a shape and a structure corresponding to shapes and structures of the cooling generating unit 113 and the heat dissipating unit 114 such that the cooling generating unit 113 and the heat dissipating unit 114 may be combined as an assembly using the coupling unit 112. Further, the coupling unit 112 may be configured to accommodate a preassembly of the cooling medium 20 and the accommodating unit 111. i.e., to form a space for such a preassembly. Therefore, with the coupling unit 112, the preassembly (i.e., the medium 20 and the unit 111), the cooling generating unit 113, and the heat dissipating unit 114 may be combined or coupled to establish the physical and thermal coupling with one another. For these reasons, using the coupling unit 112, these components 20, 111, 113, and 114 may form a single module or engine, i.e., the cooling unit 110 to generate the cooling power required to anesthetize the target area. The coupling unit 112 may be made of material with the low thermal conductivity, and thus may thermally isolate the cooling medium 20/the accommodating unit 111 from the heat dissipating unit 114 to prevent the heat of the unit 114 from being transferred to the medium 20 and the unit 111.

More specifically, the coupling unit 112 may comprise the plurality of members coupled together to form the space receiving the preassembly and also to be easily coupled to other components nearby. Further, the coupling unit 112 may include a recess or an opening 112a configured to receive the cooling generating unit 113. The opening 112a may be shaped to correspond to an outer shape of the cooling generating unit 113 and thus may immovably receive the same. The cooling generating unit 113 may be stably inserted and seated in the opening 112a while exposing from the coupling unit 112 two opposite heat absorbing and emitting surfaces thereof. Thus, the accommodating unit 111 and the heat dissipating unit 114 may contact these exposed surfaces, respectively to be thermally coupled with the cooling generating unit 113. Further, the coupling unit 112 may also have a rib or a flange configured to support ends of the unit 113 and medium 20 that are opposite to the other end thereof adjacent to the target area. Therefore, coupling unit 112 may contain the preassembly of the unit 111 and the medium 20 more stably.

Referring to FIGS. 2A to 2C, the accommodating unit 111 may be provided with compressive force by a second elastic member or mechanism 115. This second elastic member 115 may be also referred to as a second elastic unit or a second connector, in view of a configuration thereof. The second elastic member 115 may be disposed on the accommodating unit 111 and may provide the compressive force toward the cooling medium 20. As shown in the drawings, the second elastic member 115 may be disposed in a region other than the contact surface 111A of the divided members 1111 to provide the compression force. Therefore, the plurality of divided members 1111 may be tightened or pushed toward the cooling medium 20, and thus the reliable mechanical and thermal coupling with the cooling medium 20 may be achieved. For example, the second elastic member 115 may comprises a compression spring.

Meanwhile, as also shown in FIG. 1E, the medical cooling device 10 may have a gap formed between the body 100 (i.e., an outer case) and the inner case 500 where the cooling unit 110 is installed or between the body 100 and the heat dissipating unit 114. In addition, the aforementioned elastic assembly described is mechanically separated from other parts of the medical device 10. For example, the cooling medium 20 that may directly absorb external impact does not directly transfer this external impact to the cooling generating unit 113 that can be fragile. Therefore, the external impact applied to the outer case of the body 100 may be prevented from being directly transmitted to the cooling unit 110 inside the medical cooling device 10. In other words, the medical cooling device 10 may have a gap formed between the body 100 and the inner case 500 and between the body 100 and the heat radiating part 114, such that the external impact may be absorbed by deformation of the outer case into a space formed by the gap.

Referring to FIG. 2E, the cooling generating unit 113 may be disposed on a surface 111B (i.e. a second surface), which is opposite to the contact surface 111A (i.e. a first surface) of the divided member 1111, and may supply the cooling energy or the cooling power to the accommodating unit 111. In the present disclosure, the cooling energy and the provision of the cooling energy are the concept opposite to the heat energy and the provision of the heat energy. In practice, cooling means lowering a temperature of an object through an endothermic reaction, i.e, absorbing the heat from the object. However, for convenience of explanation, the cooling is defined as providing or transferring the cooling energy to the object to lower the temperature thereof.

The cooling generating unit 113 may comprise any mechanism capable of supplying the cooling energy to the accommodating unit 111 and may include one or more cooling elements capable of generating cooling energy. At least one cooling element may be disposed on the second surface 111B of the divided member 1111. The cooling element may adopt a thermodynamic cycle such as a stirling cooler or a vapor compression refrigeration cycle, a liquid evaporation, or a Joule-Thomson method using inflation gas to generate the cooling energy, i.e. to absorb the heat. Further, the cooling element may generate the cooling energy using liquid nitrogen or carbon dioxide, or may supply the cooling energy using a thermoelectric element such as a Peltier element. In the present disclosure, there is no limitation on the cooling element, but for convenience of explanation, the cooling generating unit 113 using the thermoelectric element will be described below. In view of a configuration thereof, the cooling generating unit 113 may be referred to as a cooler, a cooling generator, and the so on.

Here, the Peltier effect refers to a phenomenon in which when a current flows through a pair of n-type and p-type thermoelectric materials, the heat is emitted on one side of the pair and the heat is absorbed (i.e. cooling) on the other side thereof. This Peltier effect may be referred to as a heat-pump, to which a feedback control may be applied.

In addition, the surface of the thermoelectric element where the heat absorption occurs may be changed depending on a direction of the current provided thereto. In this case, an amount of heat absorbed on such a surface may be defined as a following equation:

$$|Q_p|=\alpha_{ab}T_jI=\pi I$$

Here, $|Q_p|$ is an absolute value of heat absorbed in unit time period, $\alpha_{ab}$ is a relative thermoelectric capacity of two materials a and b according to an ambient temperature, $\pi$ (i.e., $\alpha_{ab}T_j$) is a Peltier coefficient, and I is a current.

When the current is applied to the thermoelectric element of the cooling generating unit 113, the surface of the thermoelectric element in contact with the accommodating unit 111 may absorb the heat and the surface thereof in contact with the heat dissipating unit 114 may radiate the heat by the Peltier effect. The heat in a region where the cooling medium 20 and the object come into contact with each other may be transferred to the cooling generating unit 113 via the cooling medium 20 and the accommodating unit 111 and then may be further transferred to the heat dissipating unit 114 to be radiated outside the device 10.

The heat dissipating unit 114 may be configured to discharge the heat emitted from the cooling generating unit 113 to the outside. The heat dissipating unit 114 may be also referred to as a heat sink, a heat emitting unit, a heat radiating unit, and so on. The heat dissipating unit 114 may be made of thermally conductive material to efficiently discharge the heat generated while the cooling generating unit 113 produces the cooling energy. The heat dissipating unit 114 may be formed of two or more heat dissipating members coupled to each other and may be divided into the number corresponding to the number of the divided members 1111.

As shown in FIGS. 2A and 2B, when the accommodating unit 111 includes two divided members 1111, the heat dissipating unit 114 may include two or more heat dissipating members, i.e., at least two heat dissipating members coupled to the divided members 111, respectively. In another example as shown in FIG. 2C, when the accommodating unit 111 includes four divided members 1111, the heat dissipation unit 114 may include four or more heat dissipating members coupled to the divided members 1111, respectively. The heat dissipating members may be coupled to the divided members 1111 using a fastening means such as a bolt. Further, the cooling generation unit 113 may be interposed between the heat dissipating unit 114 and the accommodating unit 111 using the coupling unit 112 as described above and thus may be fixed therebetween by pressure provided when these two units 113 and 114 are fastened. Further, as well shown in FIG. 1G, when units 113 and 114 are fastened using the fastening member like the bolt, the coupling unit 112 interposed therebetween may also be fastened together using the same fastening member.

In one example, the heat dissipating unit 114 may be disposed radially around the accommodating unit 111 and the cooling generating unit 113. The heat dissipating unit 114 may include a plurality of heat dissipating fins provided on a surface opposite to a surface contacting the cooling generating unit 113, thereby maximizing heat dissipating efficiency.

Meanwhile, as shown in FIGS. 2C and 2I, the medical cooling device 10 may further include a seating unit 130 for allowing the cooling medium 20 to stably seat thereon. The seating unit 130 may be disposed on and coupled to a rear end of the cooling unit 110 which is an assembly of the accommodating unit 111, the coupling unit 112, the heat generating unit 113 and the heat dissipating unit 114. A rear end portion of the cooling medium 20 may be supported by the seating unit 130 or may be inserted into a recess formed in the seating unit 130. Likewise, other components of the cooling unit 110 such as the accommodating unit 111, the coupling unit 112, and/or the heat dissipating unit 114 may be supported by or inserted into the seating unit 130. Further, the seating unit 130 may include a connector 131 configured to be coupled to the cooling unit 110, and the connector 131 may comprise shock absorbing material. With such a connector 131, the seating unit 130 may protect the cooling unit 110 from the external impact. With such a configuration as described above, the seating unit 130 may be considered to be a cover or a cap configured to be disposed at a rear portion of the cooling unit 110 and to cover or protect the same.

Referring to FIG. 2D, the medical cooling device 10 may include the blowing unit 150 disposed inside the body 100, and may be configured to form a unidirectional air flow from the first end portion a to the second end portion b of the body 100. The blowing unit 150 may suck the outside air into the first end portion a of the body 100 to cool the heat dissipating unit 114 and may discharge the air to the second end portion b located in a rear of the first end portion a. The blowing unit 150 may include the fan, but is not limited thereto. Any device such as a compressed air tank, a blower, or the like capable of producing the unidirectional air flow may be applied. Accordingly, the blowing unit 150 may also be referred to as a ventilator and a circulator.

Referring back to FIG. 1B, the first mesh 101 may be provided at the second end portion b of the body 100 such that the air inside the body 100 may be discharged though the first mesh 101. Further referring to FIGS. 2C, 2D and 2I, the seating unit 130 may have a vertical section with regard to the longitudinal direction that gradually decreases from a first end 131 (i.e., the connector) adjacent to the cooling unit 110 to a second end 133 opposite to the first end 131. Further, the seating unit 130 may have a circumferential surface inclined toward the longitudinal axis of the body 100. That is, the seating unit 133 may have a cone shape. Moreover, an outer surface of the seating unit 130 may be curved inwardly. With such a configuration as described above, the seating unit 130 may smoothly guide the airflow to the second end portion b, while minimizing resistance to the airflow discharged from the heat dissipating 114. Therefore, When the airflow is formed from the first end portion a to the second end portion b as described above, the seating unit 130 may improve the heat discharging efficiency by facilitating the air flow within the cooling device 10. Thus, in light of a functional aspect described above, the seating unit 130 may serve as a guider or a regulator that is configured to smoothly guide the air flow toward the second end b, i.e., the outlet while regulating the air flow due to an outer contour thereof reducing the resistance, so as to expedite the discharge of the air. Further, the seat unit 130 may be made of material having the high thermal conductivity, and thus may perform additional heat dissipation along with the dissipating unit 114.

Meanwhile, as shown in FIGS. 1C and 2C, the medical cooling device 10 may further include a pressure sensor unit 141 for sensing a pressure applied when the cooling medium 20 is in contact with the target area of the object and generating a signal indicating the pressure. The pressure sensor unit 141 may be disposed on the accommodating unit 111 or the seating unit 130. More specifically, the sensor unit 141 may be disposed on the first end 131 of the seating unit 130 to sense the pressure applied to the cooling medium 20 from the target area. The sensor unit 141 may be configured to directly contact the cooling medium 20 to sense the pressure directly from the medium 20. Alternatively, the sensor unit 141 may be configured to contact the accommodating unit 111 or the coupling unit 112. In this instance, the sensor unit 141 may sense the pressure transferred through the unit 111 or the unit 112 from the medium 20 which directly or indirectly contact these units 111 or 112.

As shown in FIG. 2E, the medical cooling device 10 may further include a vibration generating unit (or a vibrator) 143 that generates vibration at the cooling medium 20. The vibration generating unit 143 may cause the cooling medium 20 to vibrate while the anesthesia is being performed or the medicine is being injected using the cooling medium 20, thereby reducing the pain of the patient. The vibration generating unit 143 may generate the vibration at the accommodating unit 111 to transfer the generated vibration to the cooling medium 20.

Referring to FIG. 1C, the medical cooling device 10 may further include a temperature sensor unit (or a temperature sensor) 145 for sensing a temperature of the cooling medium 20 or the accommodating unit 111. If the temperature sensor unit 145 comprises a contact sensor, such a unit 145 may be configured to be disposed at the cooling unit 110 to directly contact the accommodating unit 111 or the cooling medium 20. For example, the plurality of units 145 may be placed on the medium 20 and unit 111, respectively, Alternatively, the unit 145 may be disposed on a portion of the unit 111 that contracts the medium 20, such as the contact surface 111A such that sensing the temperatures of both medium 20 and the unit 111 is enabled by the single unit 145. In particular, the temperature sensor unit 15 installed in the accommodating unit 111 may be used to control the power provided to the cooling generating unit 113, and the temperature sensor unit 15 is installed within the thermally conductive portion of the accommodating unit 111. For example, the temperature sensor unit 14 installed in the accommodating unit 111 may be installed in a small hole of the divided unit 1111. When the cooling medium 20 is configured to be replaceable, the temperature sensor unit 145 for measuring the temperature of the cooling medium 20 may be sensed by a non-contact temperature sensor, for example, an infrared ray sensor. Further, additional sensor units may be provided to the cooling unit 110 to sense temperatures of other components (e.g., the units 113 and 114) and an overall inner temperature of the device 10.

The controlling unit (or a controller) 170 may control operation of the cooling generating unit 113 based on the temperature sensed by the temperature sensor unit 145. For example, the controlling unit 170 may control a time period for performing the anesthesia based on an ambient air temperature and the temperature of the cooling medium 20 provided from the temperature sensor unit 145. In addition, the controlling unit 170 may control the time period for performing the anesthesia based on the pressure provided from the pressure sensor 141.

Particularly, the controlling unit 170 may control the temperature of the cooling medium 20 by controlling the operation of the cooling generating unit 113 based on the temperature sensed by the temperature sensor unit 145. The medical cooling device 10 may anesthetize the target area by cooling the target area at a preset temperature and time period. For example, the preset temperature may range from about −15° C. to 5° C., and the preset time period may range from about 1 second to 120 seconds.

If anesthetizing temperature and period exceeds the preset temperature and time, the controlling unit 170 may prevent excessive cooling of the target area through controlling of the device 10 such as turning off the cooling generating unit 113. This is merely one example or implementation, and the temperature and time period may be preset in various ranges.

Here, the controlling unit 170 may include all kinds of devices capable of processing data, such as a processor. The processor may refer to a data processing device embedded in hardware and having a circuit physically structured to perform a function represented by a code or a command contained in a program. As an example of the data processing device built in the hardware, a microprocessor, a central processing unit (CPU), a processor core, a multiprocessor, an application-specific integrated circuit (ASIC), and a field programmable gate array (FPGA), but the scope of the present disclosure is not limited thereto.

In addition, the controlling unit 170 may control the cooling generating unit 113 such that the cooling medium 20 may be maintained at a constant temperature for the time period during which the anesthesia is performed. As another example, the controlling unit 170 may control the cooling generating unit 113 such that two or more temperature values are preset and the cooling medium 20 has the respective temperature values sequentially or periodically during the cooling is performed.

Thus, the medical cooling system 1 or device 10 may have various clinical effects such as the anesthesia as well as antibacterial action/vasoconstriction through various stages or steps of the cooling in different cooling conditions. In addition, it may be enabled to minimize the occurrence of ice on a tip portion 225 of the cooling medium 20 (see FIG. 5A) through the cooling condition (i.e. the cooling temperature) higher than a freezing point. In particular, the non-freezing temperature can be chosen as the initial cooling temperature prior to the application of the cooling medium 20 on the target area to prevent undesired adhesion between the cooling medium 20 and the target area. In addition, the controlling unit 170 may control the cooling generating unit 113 to cool the medium 20 to a first temperature during the anesthesia is performed, and to cool (or heat) the medium 20 to the initial temperature higher than the freezing temperature to prevent undesired adhesion between the cooling medium 20 and the target area after the application of the cooling medium 20 on the target area.

Meanwhile, the controlling unit 170 may receive the pressure signal indicating the sensed pressure from the pressure sensor unit 141 and may determine that the tip portion 225 of the cooling medium 20 has contacted the target area of the patient when the pressure signal (i.e., the sensed pressure) is greater than a preset reference value.

Further, the controlling unit 170 may receive and check the time period and the temperature signals (i.e., the sensed temperature) during the contact with the patient's target area, and may determine that the anesthesia is completed in the patient's target area if the target area is cooled for the preset period of time at the preset temperature. For example, when the force of 0.5 N or more is applied to the target area for 10 seconds at a temperature of −10° C., the controlling unit 170 may determine that the anesthesia is completed and provide a signal indicating completion of the anesthesia to the user. Therefore, the medical cooling system 1 or device 10 may accurately inform the user of the completion of the anesthesia through the configuration of the controlling unit 170 as described above, even when environment in use is changed.

Meanwhile, the controlling unit 170 determines a state of thermal coupling between the cooling medium 20 and the accommodating unit 111 based on a speed at which the temperature sensed by the temperature sensor unit 145 that provided to the accommodating unit 111 changes. This is because the heat capacity of the object to be cooled by the cooling generating unit 113 may vary depending on the state or the degree of the thermal coupling between the cooling medium 20 and the accommodating unit 111, and thus the speed at which the temperature sensed by the temperature sensor unit 145 may vary at the same cooling energy provided by the generating unit 113. That is, such a speed may accurately reflect the state or the degree of the thermal coupling between the cooling medium 20 and the accommodating unit 111.

Further, the controlling unit 170 may cool the target area at various stages or steps of temperatures. For example, the controlling unit 170 may perform rapid cooling at a low temperature at an initial stage (or step) of the treatment, and may cool the target area at a temperature higher than the temperature of the initial stage at a middle stage of the treatment. The controlling unit 170 may further control the temperature of the accommodating unit 111 such that there is no ice on the surface of the cooling medium 20 when the treatment is finished. The process for removing the ice may be performed before informing the user that the cooling process or the treatment (i.e., the anesthesia) has been completed. For example, the target area may be touched at 0° C., and then may be cooled at −10° C. for the first 5 seconds, −5° C. for 13 seconds, and 0° C. for last 2 seconds. After completion of such entire cooling period, the medical device 10 may notify a user with sound, light, or both, to ensure anesthesia and no ice adhesion between the cooling medium 20 and the target area at the moment of a user trying to detach the cooling medium 20 from the target area.

As a certain surface of the thermoelectric element may switch between the heat absorption surface and the heat radiation surface depending on the direction of the current, the cooling generating unit 113 may heat the accommodating unit 111 after use, to remove moisture, impurities, and the like.

With the configuration of the present disclosure as described above, the medical cooling system 1 or device 10 may cool the target area of the object in contact with the cooling medium 20 quickly and safely. Due to such quick and safe cooling, the medical cooling system 1 or device 10 may improve a life span and various characteristics thereof. Further, since the medical cooling system 1 or device 10 controls the heating and the cooling using electronic components thereof, precise temperature control may be obtained. The medical cooling system 1 or device 10 may also cool the object rapidly and locally after the power is supplied. Further, the medical cooling system 1 or device 10 may also operate in any position or direction regardless of the direction of gravity. The medical cooling system 1 or device 10 may also have a reduced size and weight, and may realize low noise and low vibration cooling.

FIGS. 2I to 2K are views for explaining features related to the orthogonal coupling of the medical cooling device. FIG. 2I is a perspective view showing an internal configuration of the cooling unit according to another example of the present disclosure, and FIG. 2J is a perspective view showing some components of the cooling unit in FIG. 2I. FIG. 2K is a front view as viewed in a direction in which the cooling medium of FIG. 2I is inserted.

Referring to FIGS. 2I to 2K, the cooling unit 110 according to another example of the present disclosure may include a first divided member 1111A, a second divided member 1111B, a first coupling member 112A, a second coupling member 112B, a first heat dissipating member 114A, and a second heat dissipating member 114B. That is, in this example, the accommodating unit 111 may comprises the first and second divided members 1111A and 1111B, the coupling unit 112 may comprises the first and second coupling members 112A and 112B, and the heat dissipating unit 114 may comprises the first and second heat dissipating members 114A and 114B.

In the cooling unit 110 as shown in FIGS. 2I to 2K, a plurality of divided members 1111A and 1111B may not be arranged parallel to a plurality of heat dissipating members 114A and 114B. That is, the divided members 1111A and 1111B may be arranged along a direction different from a direction along which the heat dissipating members 114A and 114B may be arranged. Particularly, the direction in which the divided members 1111A and 1111B are arranged (a third direction) may not coincide with or not be parallel to the direction in which the heat dissipating members 114A and 114B are arranged (a fourth direction). Further, the divided members 1111A and 1111B may be joined together using a first fastening member, the heat dissipating members 114A 114B may be joined together using a second fastening member, and the first and second fastening member may be separated from each other. Particularly, the divided members 1111A and 1111B may be coupled together using an elastic member 117' that is arranged along the third direction. Actually, the elastic member 117' may couple the coupling members 112A and 112B and by such coupling of members 112A and 112B, the divided members 1111A and 1111B housed in the coupling members 112A and 112B may be coupled. The heat dissipating members 114A and 114B may be coupled together using a screw 118 that is a member independent of the elastic member 117' and arranged along the fourth direction. Therefore, with such a configuration, the accommodating unit 111 and the heat dissipating unit 114 are thermally isolated from each other.

More specifically, the first and second divided members 1111A and 1111B may be each provided with a contact surface 111A contacting with the cooling medium 20, and may be arranged in the third direction to be opposite to each other with regard to the cooling medium 20. The first and second divided members 1111A and 1111B may be coupled to the first and second coupling members 112A and 112B, respectively. When the first and second coupling members 112A and 112B are coupled together along with the divided members 1111A and 1111B, these divided members 1111A and 1111B may be space apart from each other and thus may forms a space for accommodating the cooling medium 20.

The first coupling member 112A and the second coupling member 112B may be connected to each other using the elastic member 117'. By connecting and coupling the first and second coupling members 112A and 112A using the elastic member 117', the first and second divided members 1111A and 1111B may achieve the physical and thermal coupling between the contact surface 111A and the cooling medium 20. Meanwhile, the physical and mechanical coupling formed between the contact surface 111A and the cooling medium 20 may be easily loosed by the external impact thereto because the elastic member 117' may be deformed by the external impact due to elasticity thereof. Therefore, the components of the cooling unit 110 may be protected because the energy of the external impact may be absorbed by deforming elastic member 117' and releasing the physical coupling. Further, the elastic member 117' may connect the first and second divided members 1111A and 1111B and at the same time, may provide the elastic force pulling the divided members 1111A and 1111B toward each other, such that the cooling medium 20 may be securely received between the divided members 1111A and 1111B. The elastic member 117' may be any mechanism that provides the elastic force and may comprise the spring, for example.

In addition, as the elastic member 1117' may be elastically deformed, the space between the divided members 1111A and 1111b may be adjusted according to the shape of the cooling medium 20. Thus, even though a coupling surface of the cooling medium 20 has a substantially large tolerance, the thermal coupling (i.e., the physical contact) between the accommodating unit 111 and the cooling medium 20 may be optimally maintained by automatically adjusting the space or the distance between the divided members 1111A and 1111b when the cooling medium 20 is inserted between the members 1111A and 1111B. For these reasons, the coupling using the elastic member 117' may drastically reduce a manufacturing cost of the cooling medium 20, because a high precision in a size is not required.

Meanwhile, the first and second coupling members 112A and 112B may be made of material having the low thermal conductivity, such that the heat transfer between the cooling medium 20/the accommodating unit 111 and the heat dissipating unit 114 may be prevented. Therefore, the coupling members 112A and 112B may hinder the heating of the cooling medium 20 and the accommodating unit 111 by the heating dissipating unit 114, which result in reducing the cooling efficiency.

One or more cooling generating units 113 may be disposed on an installing surface of the accommodating unit 111 that is not opposite to the contact surface 111A with the cooling medium 20. Such an installing surface of the accommodating unit 111 may be located outside the coupling unit 112 and may be disposed normal to the contact surface 111A. With such orientation, the units 113 may inherently face and contact the unit 114 that is oriented normal to the unit 111. More specifically, the accommodating unit 111 may include an extension V extending normal to a body of the unit 111, i.e., in the third direction in which the divided members 1111 are arranged. Further, the extension V may extend through the coupling unit 112 to be exposed out of the coupling unit 112. The extension V may have an installing surface Vs formed at a portion of the extension V (i.e., a side of the extension V) exposed from the coupling unit 112. As shown in FIGS. 2I to 2K, the extension V may have two installing surfaces Vs formed at both sides thereof that are normal to the contact surface 111A. The plurality of cooling generating units 113 may be placed on these installing surfaces Vs. With such an extension V, the surface of the unit 111 on which the cooling generating unit 113 is allowed to be installed may be greatly increased, and thus the number of units 113 provided to the accommodating unit 111 may be increased. Therefore, the cooling performance of the device 10 may be enhanced.

The first and the second heat dissipating members 114A and 114B may be arranged along the direction (the fourth direction) intersecting the direction along which the first and second divided members 1111A and 1111B are arranged (the third direction). More specifically, the first and the second heat dissipating members 114A and 114B may be arranged along the direction (the fourth direction) perpendicular to, i.e., orthogonal to the direction along which the first and second divided members 1111A and 1111B are arranged (the third direction). However, the present disclosure is not limited thereto, and the heat dissipating members 114A and 114B may be arranged in symmetrical structures having various angles between the members (for example, 90 degrees, 120 degrees, or 180 degrees) according to the shape of the cooling medium 20.

In one example, as shown in FIGS. 2I to 2K, the first and second heat dissipating members 114A and 114B may be connected to each other through the screw 118 as shown. In this example, as the first and second coupling members 112A and 112B are coupled using the elastic member 117', and the first and second heat dissipating members 114A and 114B are coupled to each other using the screw 118, this may provide rigid coupling and flexible detachment. More specifically, since the cooling generating units 113 are located outside the coupling units 112, the cooling generating unit 113 may be interposed between the heat dissipating members 114A and 114B while directly contacting these members 114A and 114B. Therefore, the heat generating unit 113 may be securely fixed between the coupled heat dissipating members 114A and 114B with being pressed by the coupled members 114A and 114B and thus may be thermally coupled with the members 114A and 114B. Here, a direction in which the pressure by the screw 118 is applied may not be parallel with a direction in which the elastic force by the elastic member 117' is applied. In the configuration that a direction in which the pressure by the screw 118 is parallel with a direction in which the elastic force by the elastic member 117' is applied, the line of the pressure by the screw 118 is not collinear with the line of the pressure by the elastic member 117', allowing thermal isolation between the heat dissipating member 114 and the accommodating unit 111. Thus, the screw 118 used to couple the cooling generating unit 113 and the heat dissipation members 114 is independent of the elastic member 117' used to couple the cooling generating unit 113 and the accommodating unit 111, mechanically and hence thermally isolating the accommodating unit 111 from the heat dissipating unit 113.

In this example, one surface of the cooling generating unit 113 may be thermally coupled with the divided members 1111 of the accommodating unit 111 to absorb the heat therefrom. Further, the other surface of the cooling generating unit 113 may be thermally coupled with the heat dissipating unit 114 to radiate the heat thereto. As the heat dissipating unit 114 and the accommodating unit 111 may be indirectly connected by interposing the cooling generating unit 113 therebetween but not directly connected to each other, the heat dissipating unit 114 may be thermally isolated from the accommodating unit 111. Therefore, the heat radiating efficiency at the heat dissipating unit 114 as well as the cooling efficiency at the accommodating unit 111 may be greatly improved.

FIGS. 3A to 3D are views for explaining features related to the lubricating member of the medical cooling device.

More specifically, FIGS. 3A to 3D are views showing various examples for providing the lubricating member to the accommodating unit 111 of FIG. 1.

Referring to FIGS. 3A to 3D, a medical cooling system 1 according to one example of the present disclosure may be provided with a removable cooling medium 20 so as to be inserted into the medical cooling device 10 to be cooled. The cooling medium 20 may be easily detached from the medical cooling device 10 and may be configured to be disposable for hygienic reason so as to prevent contamination of the target area. For this purpose, the medical cooling device 10, specifically the accommodating unit 111 thereof may be provided with a lubricating member 120 so as to easily accommodate the removable cooling medium 20. As the lubricating member 120 is interposed between the accommodating unit 111 and the cooling medium 20 while physically contacting these unit 111 and medium 20, the lubricating member 120 may thermally couple the unit 111 with the medium 20. In the present disclosure, the cooling medium 20, the removable cooling medium 20, the detachable cooling medium 20, and the disposable cooling medium 20 may refer to the same configuration.

The lubricating member 120 may be formed on a portion of the contact surface 111A of the accommodating portion 111, at least and may provide lubrication between the accommodating portion 111 and the removable cooling medium 20. The lubricating member 120 may further improve wear resistance against repeated replacement of the removable cooling medium 20.

In one example, the lubricating member 120 may be formed on an entire portion of the contact surface 111A by polishing the contact surface 111A. The polished contact surface 111A may have a surface roughness less than those of other surfaces of the accommodating unit 111. For example, a center line average roughness Ra of the contact surface 111A may be 100 μm or less. For another example, the center line average roughness Ra of the contact surface 111A may be 25 μm or less. The accommodating unit 111 may have the smooth contact surface 111A due to the lubricating member 120, and thus detachment of the removable cooling medium 20 may be facilitated.

Figure 3A:
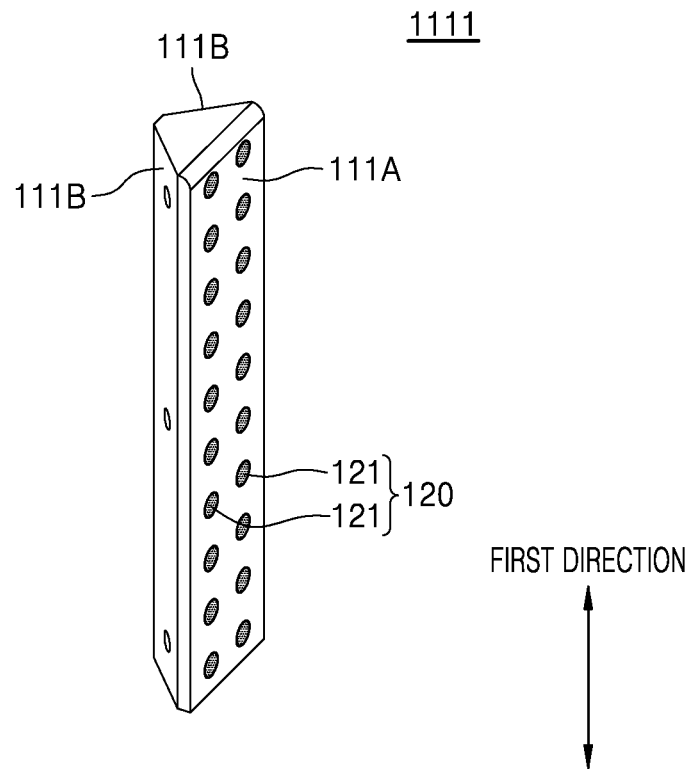
FIGS. 3A to 3D are views illustrating examples of a lubricating member of the medical cooling device
Figure 3B:
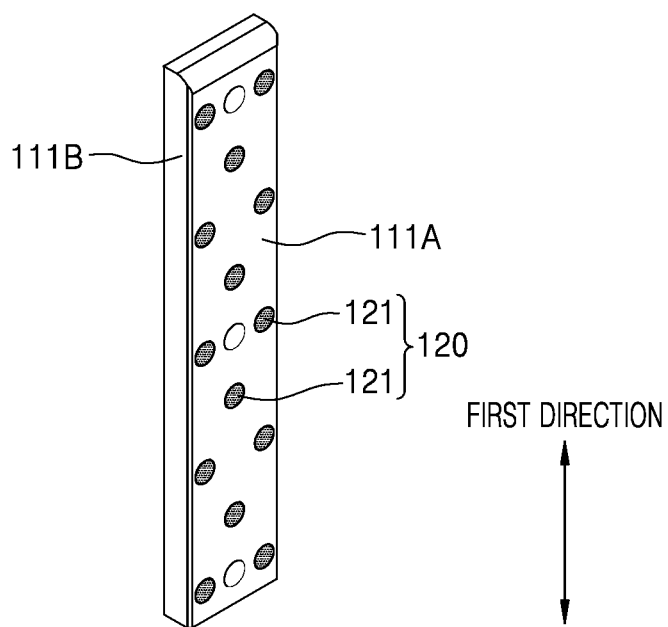
Figure 3C:
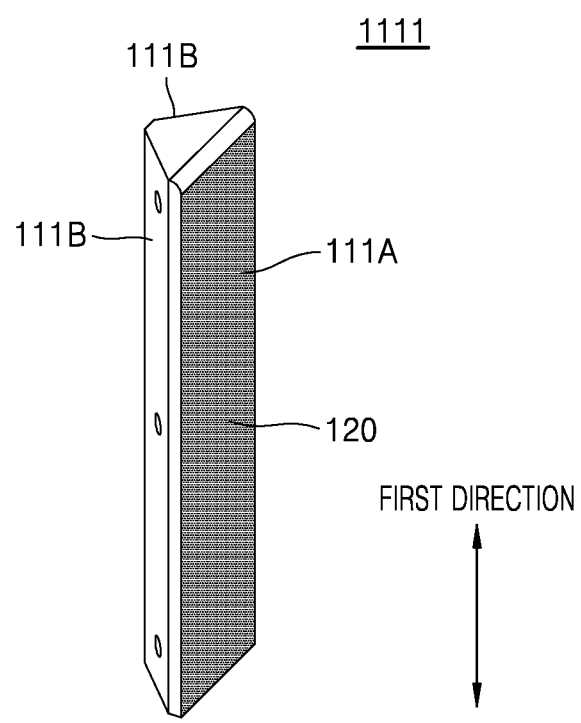
Figure 3D:
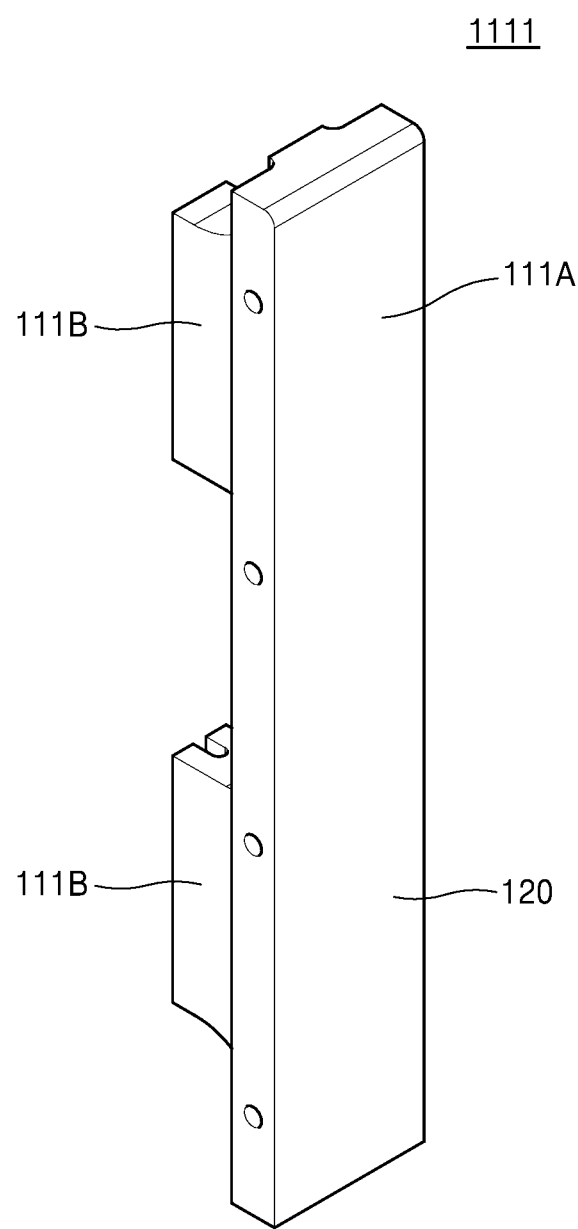

As another example, the lubricating member 120 may be formed by coating solid lubricant on the contact surface 111A of the divided members 1111, as shown in FIG. 3C. Referring to FIG. 3D, another lubricating member 120 formed on the contact surface 1111A is shown, and depending on the structure and shape of the divided member 1111, the lubricating member 120 may be variously formed.

The solid lubricant may be coated on the entire portion of the contact surface 111A or may be coated locally on the contact surface 111A. Such solid lubricant may include at least one of material having a low friction coefficient and high thermal conductivity, for example, diamond like carbon, graphite, graphene, and tungsten carbide, but is not limited thereto. Further, the solid lubricant may be at least one selected from the group consisting of molybdenum disulfide, graphite, cerium fluoride, zinc oxide, tungsten disulfide, mica, boron nitrate, boron nitride, borax, sulfuric acid, silver, cadmium iodide, lead iodide, barium fluoride, tin sulfide, fluorinated carbon, PTFE, zinc phosphide, zinc phosphates, diamonds, and mixtures thereof. The accommodating unit 111 may reduce the coefficient of friction of the contact surface 111A using the solid lubricant. Therefore, the replacement of the removable cooling medium 20 may be facilitated. Further, the impact applied to the cooling medium 20 may be absorbed by the lubricating member 120 itself or by movement of the medium 20 allowed via the reduced friction by the lubricating member 120 so as not be transmitted to other components of the medical cooling device 10.

As another example of the present disclosure, the lubricating member 120 may include one or more solid lubricating portions 121 that are locally disposed on the contact surface 111A. When the solid lubricant is coated on the entire contact surface 111A of the divided member 1111, the contact surface 111A may have the increased wear resistance, but the thermal conductivity thereof may be somewhat decreased. Therefore, the lubricating member 120 may increase the wear resistance while maintaining the heat transfer efficiency by disposing the solid lubricating portion 121 locally on the contact surface 111A of the divided member 1111.

As shown in FIGS. 3A to 3D, the lubricating member 120 may include a plurality of circular solid lubricating portions 121 that are disposed in a predetermined order or pattern on the contact surface 111A. For example, as shown in FIG. 3A, the solid lubricating portions 121 may be arranged at regular or fixed intervals along the longitudinal direction of the divided member 1111 (i.e., the first direction). Further, as shown in FIG. 3B, the solid lubricating portions 121 may be staggered, i.e. arranged in a zigzag manner along the longitudinal direction of the divided member 1111 (i.e., the first direction). However, the scope of the present disclosure is not limited thereto, and the solid lubricating portion 121 may be irregularly arranged on the contact surface 111A of the divided member 1111. Further, the solid lubricating portion 121 may have various shapes other than circular shape.

In another example, the lubricating member 120 may be formed by coating material including at least one of nickel, a nickel alloy, and a cobalt chromium alloy on the contact surface 111A. Hardness of the contact surface 111A, more specifically the hardness of a portion where the lubricating member 120 is formed may be greater than the hardness of other portions of the divided member 1111, while the friction coefficient of the contact surface 111A may be less than the friction coefficients of the other portions of the divided members 1111.

According to the configuration of the present disclosure as described above, the medical cooling system 1, particularly the cooling device 10 may increase the wear resistance to the repeated replacement of the removable cooling medium 20, and may permit the removable cooling medium 20 to be easily detached from the device 10. Further, in the medical cooling system 1 or device 10, the cooling medium 20 that is in direct contact with the target area may be replaced after use, and thus this may minimize contamination of the target area.

III. Heat Transferring Medium

FIGS. 4A to 4E are views for explaining features related to a heat transferring medium including a heat pipe of a medical cooling device.

Figure 4A:
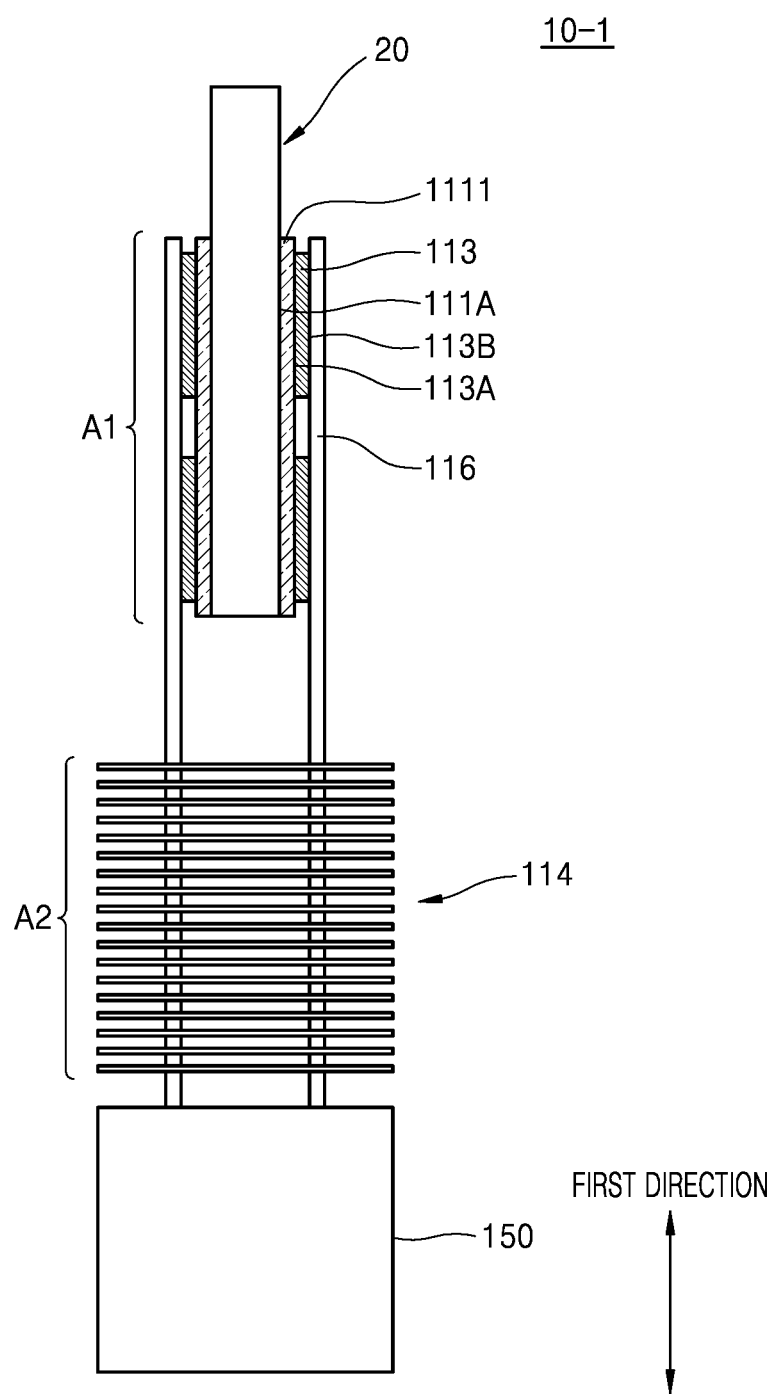
FIGS. 4A to 4E are views illustrating examples of a heat transferring medium of the medical cooling device.
Figure 4B:
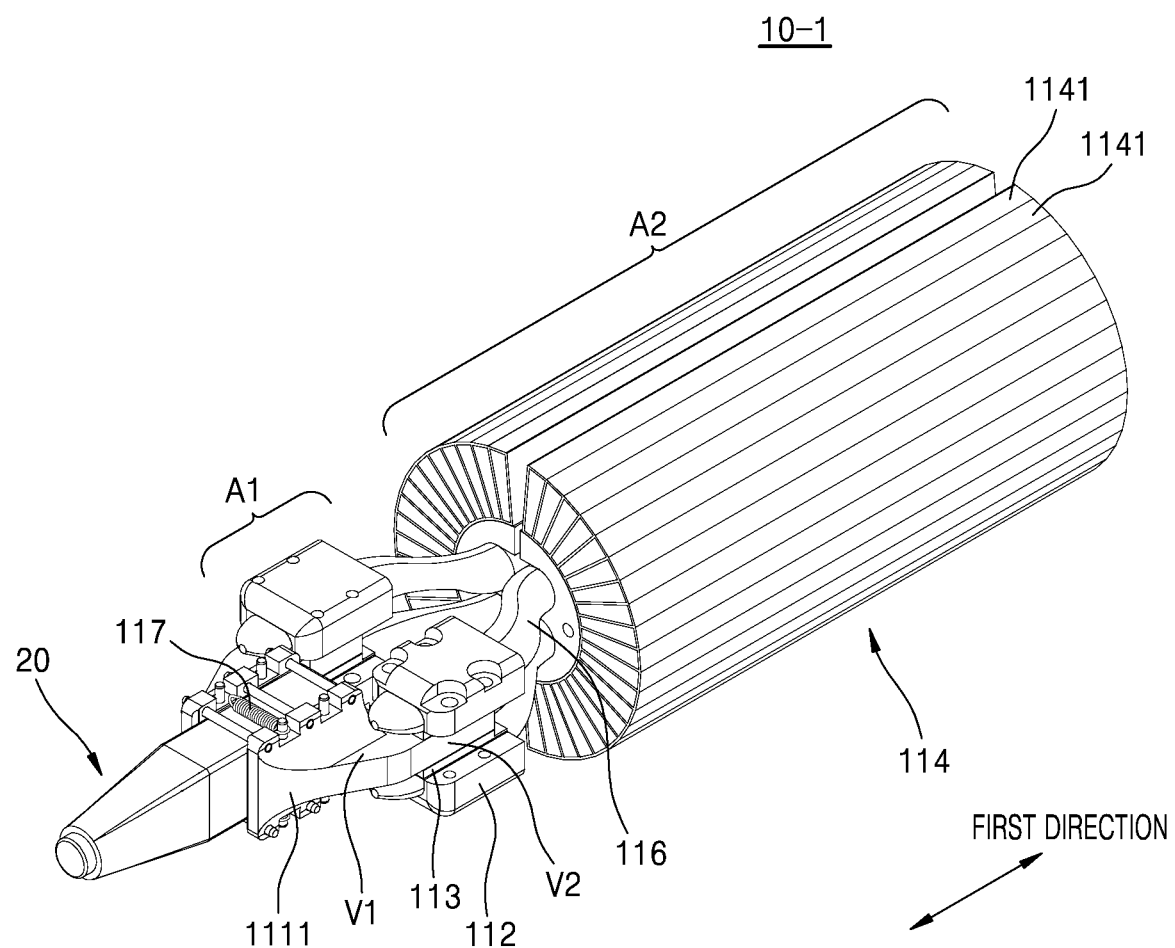

FIG. 4A is a conceptual view for explaining a medical cooling device according to another example of the present disclosure. FIG. 4B is a perspective view showing a configuration of the heat transferring medium according to a preferred example of the present disclosure. The medical cooling device according to another example of the present disclosure may be configured to separate the heat dissipating unit from the cooling medium by adopting the heat transferring medium to cool the cooling device in various blowing manners. For example, the heat generated at the cooling device may be dissipated by generating the air flow in a first direction parallel to the longitudinal direction of the body of the cooling device or by generating the airflow in a second direction that is not parallel to the longitudinal direction of the body. When the air is set to blown in the second direction, the blowing unit may include a plurality of fans to dissipate the heat more effectively.

Referring to 4A and 4B, a medical cooling device 10-1 may include a cooling medium accommodating unit 111, a cooling generating unit 113, a heat dissipating unit 114, a heat transferring medium 116, and a blowing unit 150. Hereinafter, for convenience of description, the same reference numerals are assigned to the same components as those of the examples as described above, and any repeated description for such same components will be omitted. In the medical cooling device 10-1 according to another example of the present disclosure, the heat dissipating unit 114 may not be closely adjacent to or directly contact the cooling generating unit 113 but may be spaced apart from the cooling generating unit 113 to radiate the heat from the unit 113.

The cooling medium accommodating unit 111, briefly the accommodating unit 111 may comprise the plurality of divided members 1111 each having the contact surface 111A that is thermally coupled with the cooling medium 20 via the directly contact with the cooling medium 20. The accommodating unit 111 may form the space for accommodating the cooling medium 20 by spacing the divided members 1111 with a predetermined distance. The cooling medium 20 may be accommodated in such a space and may be cooled via the thermal coupling with the contact surface 111A of the divided members 1111. The plurality of divided members 1111 may be coupled to each other using the elastic member 117.

The entire accommodating unit 111 may be disposed to overlap with or cover the cooling medium 20, as shown in FIG. 4A. Specifically, an entire surface of the unit 111 facing the medium 20, i.e., the entire contact surface 111A may contact the cooling medium 20. The cooling generating unit 113 may include a first surface 113A connected to the accommodating unit 111 and a second surface 113B opposite to the first surface 113A. The entire first surface 113A may directly contact the surface of the accommodating unit 111 that is opposite to the contact surface 111A. As the accommodating unit 111 is entirely overlapped with the cooling medium 20 as described above, the cooling generating unit 113 on the accommodating portion 111 may be also overlapped with the cooling medium 20.

As another example, a portion of the accommodating unit 111 may overlap with or cover the cooling medium 20, as shown in FIG. 4B. Actually, such a portion of the accommodating unit 111 may directly contact the cooling medium 20 and may forms a main body of the unit 111. Further, the accommodating unit 111 may have a first extension V1 protruding the main body thereof. The cooling generating unit 113 may be disposed on the extension V1. Moreover, the accommodating unit 111 may further include a second extension V2 extending backward, i.e., toward the heat dissipating unit 114 disposed in a rear of the medium 20 along the longitudinal direction (the first direction). With such a configuration of the second extension V2 disposed close to the heat dissipating unit 114, the accommodating unit 111 may be thermally coupled with the unit 114 more easily. Thus, as shown in FIG. 4B, the cooling generating unit 113 may be disposed on the second extension V2 instead of the first extension V1. These extensions V1 and V2 may also allow more the cooling generating units 113 to be installed on the accommodating units 111, and advantages thereof are already described with regard to the extension V and the surface Vs referring to FIGS. 2I to 2K.

Figure 4C:
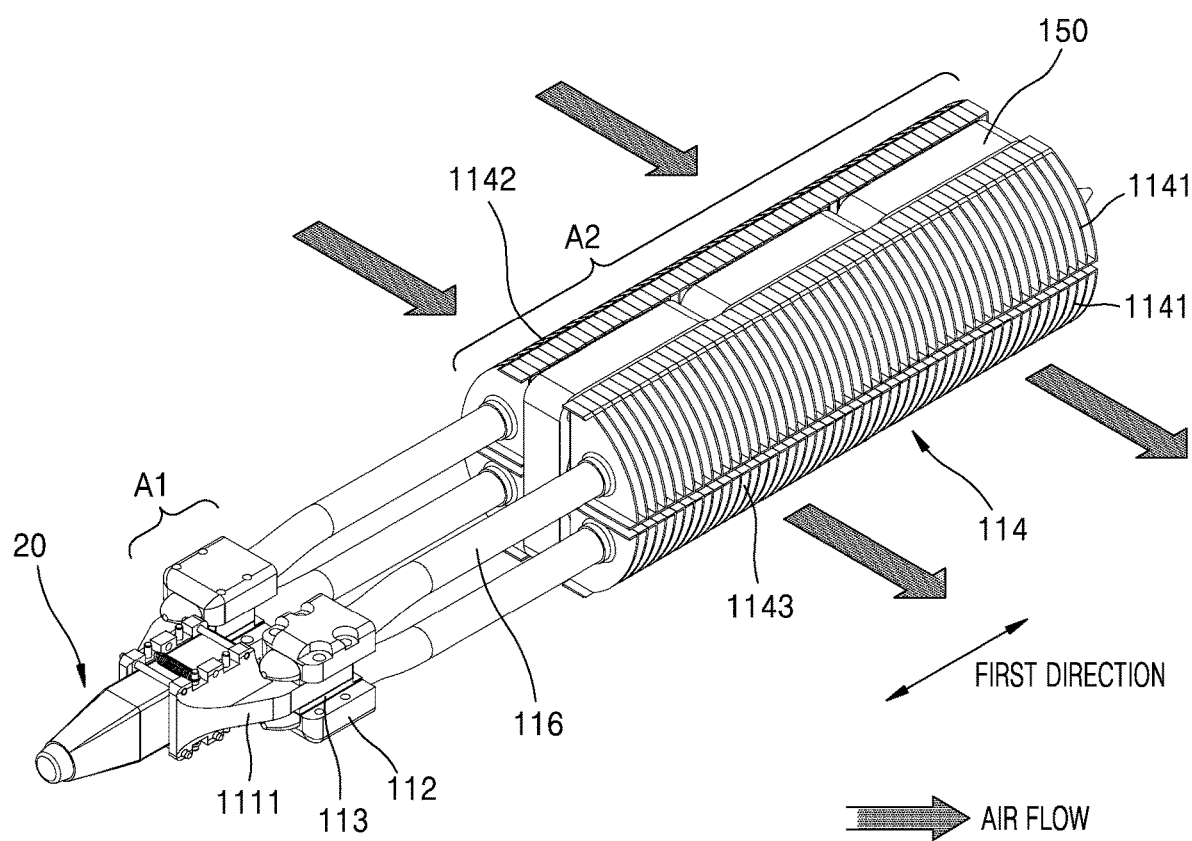
Figure 4D:
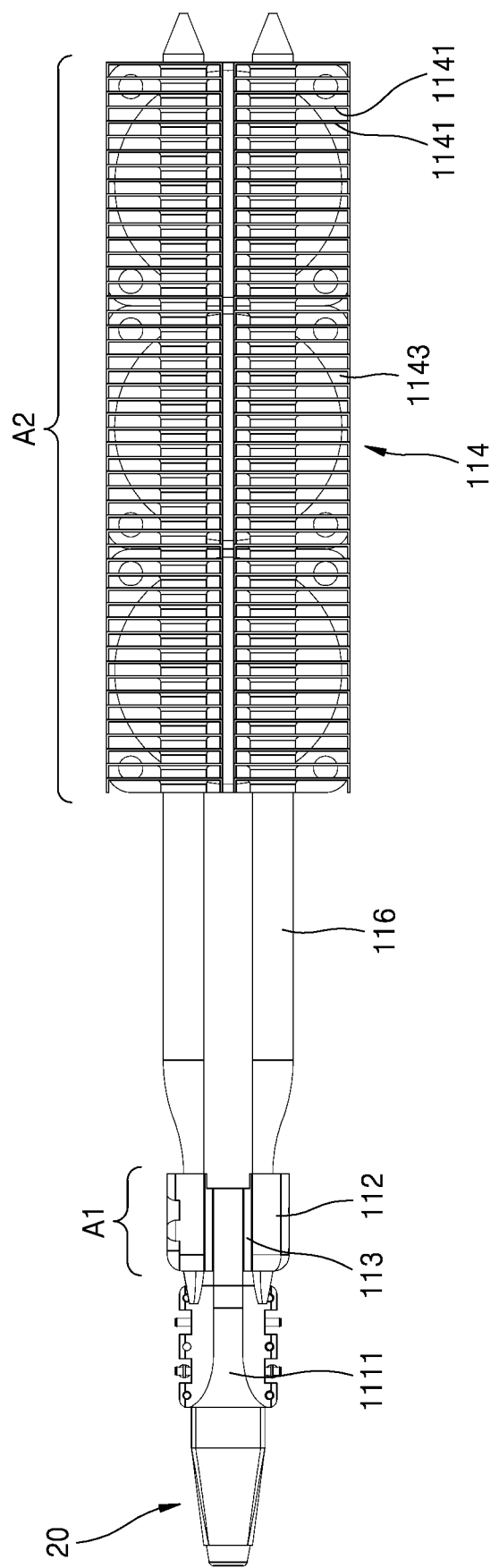

The heat transferring medium 116 may have a first region A1 coupled to the cooling generating unit 113 and a second region A2 coupled to the heat dissipating unit 114. In light of such a configuration, the heat transferring medium 116 may be referred to as a thermal connector configured to thermally connect the unit 113 to the unit 114 spaced apart from, particularly located in a rear of the unit 113. A first region A1 of the heat transferring medium 116 may be disposed on the cooling generating unit 113 on the accommodating unit 111 and the coupling unit 112 may be disposed on the first region A1. Therefore, by fixing the coupling unit 112, the first region A1, the accommodating unit 111 and the cooling generating unit 113 intervening between the region A1 and the unit 111 may be coupled altogether. To fix the heat transferring medium 116, as shown in FIGS. 4B-4D, a pair of coupling unit 112 may be disposed oppositely with regard to the accommodating unit 113 and may be coupled together using the fastening member such as the screw. As such a fastening member and the coupling unit 112 are not physically connected to the accommodating unit 111 and the elastic member 117 for coupling the accommodating unit 111, the heat transferring medium 116 may be thermally isolated from the accommodating unit 111.

The heat dissipating unit 114 may be spaced apart from the cooling generating unit 113, but may be thermally coupled to the cooling generating unit 113 to discharge the heat of the cooling generating unit 113 to the outside of the cooling device 10. The heat dissipating unit 114 may be disposed in a rear of the accommodating unit 111 and may be thermally coupled with the cooling generation unit 113 via the heat transferring medium 116. The heat dissipating units 114 may include a plurality of heat dissipating fins 1141 spaced from each other and disposed radially around the heat transfer medium 116. The blowing unit 150 may be disposed behind the heat dissipating unit 114 to generate an air flow in the longitudinal direction of the body 100. That is, the blowing unit 150 may generate the air flow in an axial direction of the heat dissipating unit 114 such that the air flow may travel along the heat dissipating fin 1141.

FIGS. 4C and 4D are views showing a blowing configuration according to another example of the present disclosure.

Referring to FIGS. 4C and 4D, a medical cooling device 10-2 may have the blowing unit 150 comprising a plurality of fans. As shown in FIGS. 4C and 4D, the heat dissipating unit 114 may include a plurality of heat dissipating sections, and the number of the heat dissipating sections may correspond to the number of the heat transferring medium 116. The heat dissipating sections may extend in the longitudinal direction (the first direction) of the body 100 and may be space apart from each other. As shown, the heat dissipating unit 114 may include at least a pair of sections spaced apart from the each other. The heat dissipating sections may be also referred to as heat dissipating members in view of a configuration thereof. The blowing unit 150 including at least one fan may be disposed in a space formed between the heat dissipating sections. As described above, the plurality of fans may be disposed in such a space. Alternatively, the blowing unit 150 may be disposed outside the heat dissipating sections (i.e., the heat dissipating unit 114).

The blowing unit 150, particularly a blowing direction thereof may be oriented not parallel to the longitudinal direction or the axial direction of the body 100 (the first direction) to cause the air to flow not parallel to the first direction. That is, the blowing unit 150 may form the air flow in a direction not parallel to the axial direction of the heat dissipating unit 114. More specifically, in the medical cooling device 10-2, the blowing unit 150 may be oriented perpendicular to the longitudinal direction of the body 100 (the first direction) and may also form the air flow perpendicular to the first direction. By disposing the blowing unit 150 in the divided heat dissipating unit 114, a path through which the air flows may be formed over a significantly large area of the heat dissipating unit 114 with a relatively short distance, and thus greatly enhance the heat transfer between the fins 1141 and the air. Alternatively, the blowing unit 150, particularly the blowing direction thereof may be oriented in the longitudinal direction or the axial direction of the body 100 (the first direction) to cause the air to flow in such a direction.

Further, when the blowing unit 150 has the plurality of fans, an arranging direction of the plurality of fans and the axial direction of the heat dissipating unit 114 may be parallel with each other, and the arranging direction of fans may intersect the blowing direction of the fans.

As shown in FIG. 4D, the heat dissipating unit 114 may include an inlet 1142 and an outlet 1143 formed between the fins 1141 to allow the air flow formed by the blowing unit 150 to pass therethrough. That is, the heat dissipating unit 114 may be formed with a plurality of inlet 1142 and outlet 1143 that extends in a direction not parallel to the axial direction of the body 100. When the blowing unit 150 includes the plurality of fans, a predetermined number of the inlet 1142 and the outlet 1143 may be assigned to each of fans. More specifically, the plurality of inlets 1142 and outlets 1143 may be assigned to each fan. Alternatively, a single inlet 1142 and a single outlet 1143 may assigned to each fan. That is, the number of the inlet 1142 and the number of the outlet 1143 may corresponds to the number of the fan. In view of such a configuration, the heat dissipating unit 114 may have at least one inlet 1142 and at least one outlet 1143 corresponding to each fan of the blowing unit 150. These inlet 1142 and outlet 1143 may be formed to pass through the heat dissipating unit 114. The air may be sucked through the inlet 1142 and may be discharged though the outlet 1143 when the blowing unit 150 operates. The inlet 1142 and the outlet 1143 may align with each other and the blowing unit 150, i.e., the fan may be disposed between the inlet and outlet 1143. As shown, the plurality of inlets 1142 may align with the plurality of outlets 1143, and thus a plurality of paths for air flow may be formed between the aligned inlets and outlets 1142 and 1143. With such a configuration of the inlet and outlet 1143, the heat transfer between the air and the heat dissipating unit 114 may be efficiently performed. In another example, a fan of the blowing unit 150 has the different direction of air flow with other fans of the blowing unit 150.

In addition, the heat dissipating unit 114 and the blowing unit 150 may be protected from foreign matter by providing a filter near a portion, i.e. the inlet 1142 through which the outer air is sucked. The filter may be installed at or near a portion of the outer case of the cooling device 10. Such a portion and the filter may be configured to be easily removed by the user, in order to easily clean the filter. For example, such a portion of the outer case may be configured to be detachably coupled to other portions of the outer case using a snap joint, a magnet, and the like and thus may be easily removed by the user.

The heat transferring medium 116 may connect the cooling generating unit 113 and the heat dissipating unit 114 to transfer the heat of the cooling generation unit 113 to the heat dissipation unit 114. The heat transfer medium 116 may comprise a heat pipe or a vapor chamber and may include a pipe body and phase change material (PCM) provided inside the pipe body. The pipe body may be made of material having the high thermal conductivity so as to effectively transfer the heat from the cooling generating unit 113 that is in contact with the heat transferring medium 116 to the PCM therein. The PCM is the material that is able to store a great amount of thermal energy or release the stored thermal energy through the phase change. Further, the PCM has a unique heat storage capacity.

Alternatively, the heat transferring medium 116 may comprise a pipe including a fluid that forcibly flows or circulates therein by using a pump or the like. The fluid (i.e., the working fluid) may have high heat transfer capacity. More specifically, the heat transferring medium 116 may have the first region A1 which is thermally coupled with the second surface 113B of the cooling generating unit 113 to absorb the heat energy from the cooling generating unit 113. Further, the heat transferring medium 116 may have a second region A2 which extends in the longitudinal direction (the first direction) of the accommodating unit 111 from the first region A1 and is thermally coupled to the heat dissipating unit 114. Thus, the heat transferring unit 116 may emit the heat energy absorbed at the first region A1 via the second region A2. Here, the second region A2 of the heat transfer medium 116 may not overlap with the accommodating unit 111, and more specifically, may not contact the accommodating unit 111. Such configurations of the first and second regions A1 and A2 may be similarly applied to the heat transferring medium 116 comprising the heat pipe or the vapor chamber as described above.

The medical cooling system 1 or device 10-1, 10-2 according to the present disclosure may use the heat transferring medium 116 containing the phase change material or the forcibly circulating fluid to effectively transfer the heat generated from the cooling generating unit 113 to the heat dissipating unit 114 in order to be radiated the outside of the device 10. That is, the amount of cooling energy per unit area generated at the cooling generating unit 113 (i.e., the thermoelectric element) may be greatly increased when the heat transferring medium 116 is used, because of superior heat transfer performance per unit area of the heat transferring medium 116. Accordingly, the accommodating unit 111 may effectively transfer the significant amount of the cooling energy received from the unit 113 to the cooling medium 20 even via a relatively small contact area with the cooling medium 20, and thus a size of the cooling medium 20 may be reduced.

As described above, the medical cooling device 10-1 or 10-2 may be configured to be slim like the pen, because the heat dissipating unit 114 is not disposed adjacent to the accommodating unit 111 but is disposed apart from the accommodating unit 111. Further, because the center of gravity is formed close to a middle point in the longitudinal direction of the device 10-1 or 10-2, the medical cooling device 10-1 or 10-2 may improve the convenience in use and enable the user to grip the device 10-1 or 10-2 easily. Moreover, as described above, the first body 100A including the cooling unit 110 may be configured separately from the second body 100B including the battery. The first body 100A and the second body 100B may be formed in the triangular structure and thus any portion of the bodies 100A and 100b may be freely gripped by the user without the additional grip as described above.

Further, the medical cooling device 10-1 or 10-2 may generate the air flow far from the target area by using the dissipating unit 114 and the blowing unit 150 disposed at the rear portion of the device 10-1 or 10-2. Therefore, In addition to the improvement of the heat dissipation efficiency, the cooling energy loss at the cooling medium 20 due to convection may be reduced by reducing the airflow near the cooling medium 20, and the risk of infection at the target area is reduced by reducing the airflow at the target area.

Figure 4E:
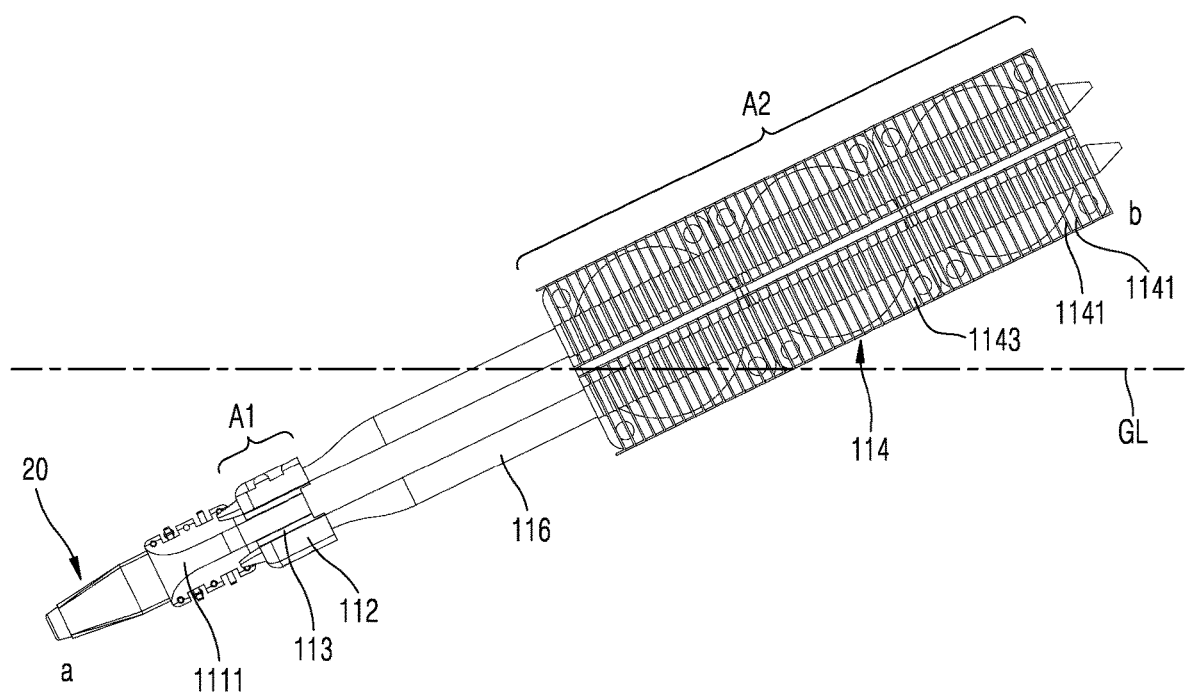

FIG. 4E is a view showing the principle of operation of the heat pipe according to the present disclosure.

Referring to FIG. 4E, when the heat transfer medium 116 comprises the heat pipe or the vapor chamber, the cooling device 10-2, particularly the body 100 thereof may be configured to guide the first end portion a (i.e. a front end portion) at which the cooling generating unit 113 is located to be lower than the second end portion b (i.e., a rear end portion) at which the heat dissipating unit 114 is located during the use of the device 10-2, with reference to a horizontal plane GL which is set on the device 10-2 and is parallel to the ground. That is, the first end portion a may be inclined down toward the ground. The PCM may be heated at the cooling generating unit 113 and thus may tend to move upward due to the changed phase and the changed specific gravity thereby. Therefore, with such a posture of the device 10-2, the heated PCM may easily move from the cooling generating unit 113 to the heat dissipating unit 114 to increase the heat transferring efficiency. For example, if the switch or the button of the medical cooling device 10-2 is located at the second end b, the first end portion a may be inherently guided to be lower than the second end portion b while the device 10-2 is being used. Further, as the cooling medium 20 is located at the first end portion a and the target area is usually located lower than the device 10-2, the first end portion a may be inherently located lower than the second end portion b while the cooling medium 20 contacts the target area for the anesthesia. Therefore, in some implementation, the components of the device 10-2 may be configured or positioned to guide the first end portion a to be lower than the second end portion b during use.

According to some implementation as above, an evaporating portion of the heat pipe (i.e., the heat transferring medium 116) may be located at or connected to the heat radiating portion of the cooling generating unit 113, and a condensing portion of the heat pipe may be located at or connected to the blowing unit 150 and/or the heat dissipating unit 114. As described above, the heat transferring efficiency of the medium 116 may be increased and thus a time period for reaching a target cooling temperature may be reduced by guiding the cooling generating unit 113 to be lower than the heat dissipating unit 114 during the operation of the cooling device.

As the first end portion a is used while being positioned lower than the second end portion b with reference to the horizontal plane GL, the phase change material which is the working fluid provided in the heat transferring medium 116, may actively circulated, increase the cooling effect, and thus effectively reduce the time period for reaching the target cooling temperature during the precooling and main cooling.

Further, as described above referring to FIG. 1H, the medical cooling device 10 may further include a control button (not shown) for allowing the user to control the device 10 or/and a display unit (not shown) for allowing the user to monitor a status of the device 10.

The control button and/or the display unit may be disposed adjacent to the heat dissipating unit 114 of the cooling device 10. That is, the control button and/or the display unit may be disposed at the rear portion of the device 10. Therefore, the user may operate the device 10 using the control button disposed on the rear portion or surface even when the device 10 is being precooled before use, and may monitor a status of precooling through the display unit. With such a configuration, the device 10, particularly the body 100 thereof may be also configured to guide the first end portion a to be lower than the second end portion b with reference to the horizontal plane GL.

IV. Removable Cooling Medium

FIGS. 5A to 5E are views for explaining features related to a tip of the removable cooling medium.

Figure 5A:
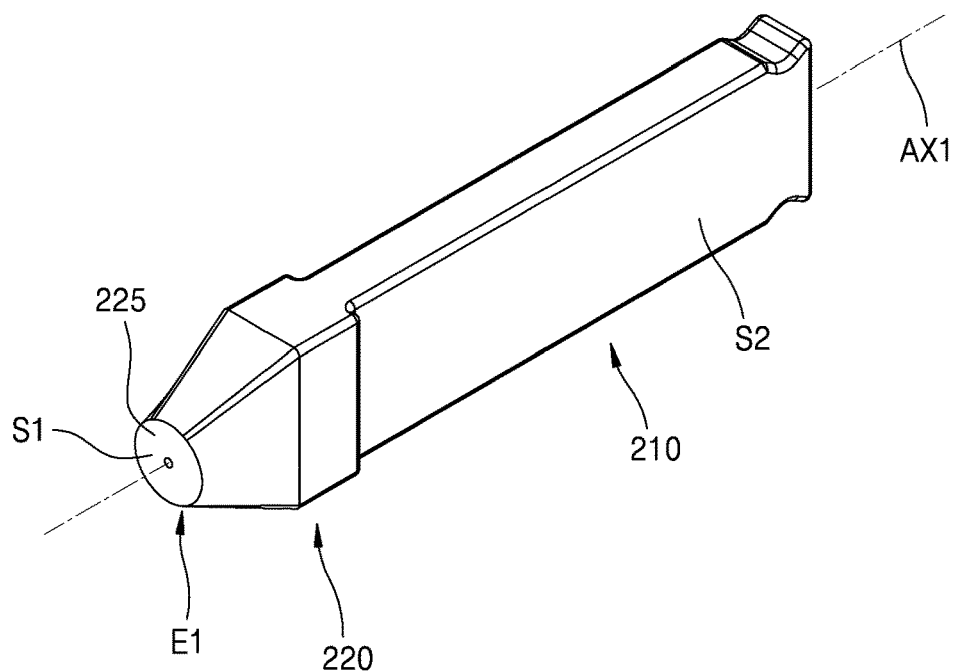
FIGS. 5A to 5E are views illustrating examples of a removable cooling medium.
Figure 5B:
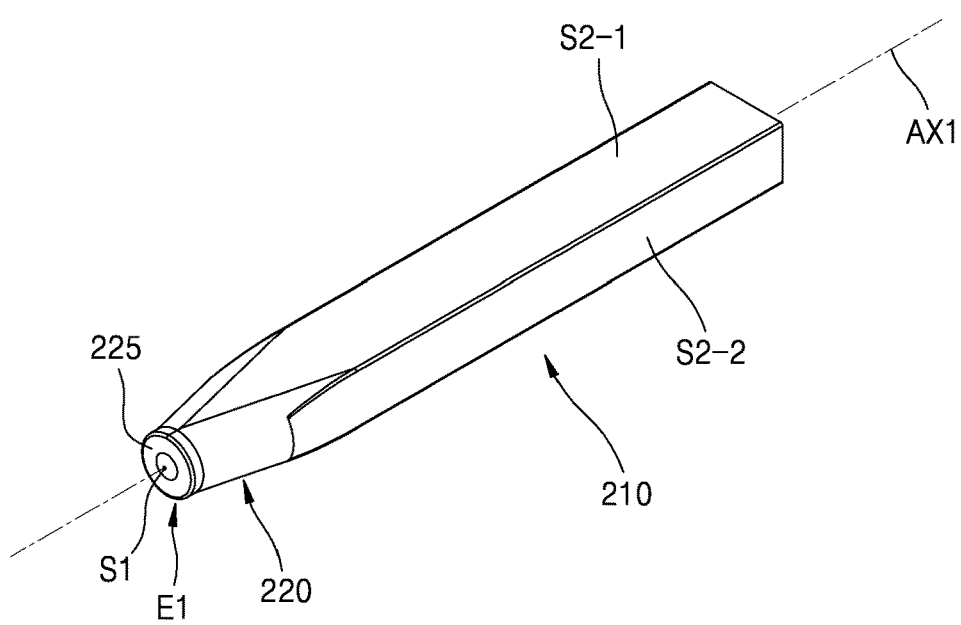
Figure 5C:
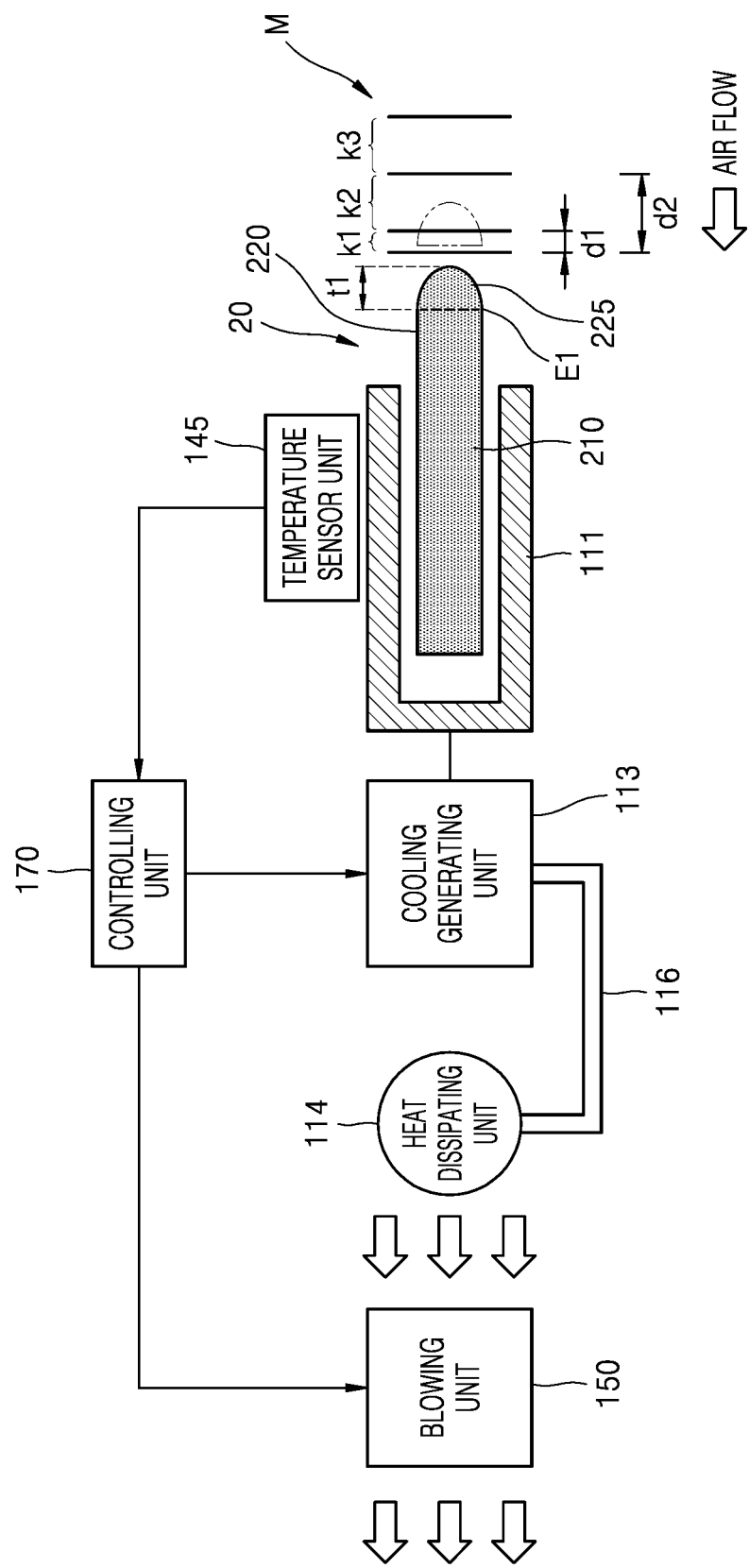

FIG. 5A is a perspective view showing a detachable or removable cooling medium according to one example of the present disclosure, and FIG. 5B is a perspective view showing another example of the removable cooling medium. FIG. 5C is a block diagram for explaining relationship between the removable cooling medium and the medical cooling device. Hereinafter, the removable cooling medium 20 according to an example of the present disclosure will be described in more detail.

Basically, as described in Sections II and Ill, the removable cooling medium 20 may receive and collect the cooling energy via the accommodating unit 111 comprising the single divided member 1111 or the plurality of divided members 1111. A tip 225 of the removable cooling medium 20, specifically a narrow area or region of the tip 225 may be further configured to concentrate the collected cooling energy thereon. This allows the medical cooling system 1 or device 10 to perform the anesthesia by effectively cooling the target area. The cooling medium 20 may be further configured to be easily separated from the medical cooling device 10 to minimize the risk of infection.

The function of the cooling medium 20 is primarily to perform the cooling for the target area such as the eye. In the present disclosure, the cooling medium 20 may be the removable cooling medium that is detachably installed to the medical cooling device 10 and is formed disposable. However, the scope of the present disclosure is not limited thereto, and the cooling medium 20 may not necessarily be provided in a removable manner. Hereinafter, for convenience of explanation, the cooling medium, the removable cooling medium, the disposable cooling medium, the detachable cooling medium and a cartridge type cooling medium may referred to as the same component.

Referring to FIGS. 5A to 5C, the removable cooling medium 20 may include an insertion portion 210 and a non-insertion portion 220. The insertion portion 210 (a first portion) may comprise a portion of the medium 20 that is inserted into the device 10 to contact the accommodating unit 111. Further, the non-insertion portion 220 (a second portion) may comprise a portion of the medium 20 that is not inserted into and thus exposed outside from the device 10 to contact the target area.

More specifically, the insertion portion 210 may be inserted into the accommodating unit 111 to collect the cooling power. In addition, the non-insertion portion, particularly the tip 225 thereof may contact the target area to cool the target area using the collected cooling power.

The insertion portion 210 may be inserted into the accommodating unit 111 and may transfer the cooling energy delivered from the accommodating unit 111 to the non-insertion portion 220. The insertion portion 210 may receive the cooling energy through an outer surface S2 that is in thermal contact with the accommodating unit 111.

The insertion portion 210 may be formed in a shape corresponding to the space formed by the divided members 1111 of the accommodating unit 111. For example, as shown in FIG. 2B, when the accommodating space is formed by the two divided members 1111 that is symmetrically disposed, the insertion portion 210 may have two outer surfaces S2 that are opposed to each other and is in contact with the divided members 1111, as shown in FIG. 5A. As another example, when the accommodating space is formed by the four divided members 1111 that is symmetrically disposed, as shown in FIG. 2C, the insertion portion 210 may have a pair of first outer surfaces S2-1 and a pair of second outer surfaces S2-2, as shown in FIG. 5B. The pair of first outer surfaces S2-1 may be opposed to each other and may contact the divided members 1111 disposed adjacent thereto. The same configuration may be applied to the pair of second outer surfaces S2-2.

As shown in FIGS. 5A and 5B, the cross section of the insertion portion 210 that is normal to an axial direction AX1 may have a rectangular shape. However, the scope of the present disclosure is not limited thereto, and the cross section may have a polygonal shape such as a circle or a triangle. Thus, the number of the outer surface S2 contacting the divided members 1111 may be two or more.

The non-insertion portion 220 may not be inserted into the medical cooling device 10 and may have tip 225 provided at an end E1 and thermally contacting the target area. The non-insertion portion 220 may extend along the axial direction AX1 from the insertion portion 210 and may have a diameter gradually decreased from the end E1. That is, the non-insertion portion 220 may be tapered when viewed in a section taken along the axial direction AX1.

The tip 225 provided at the non-insertion portion 220 may come into contact with the target area such as the eyeball and may cool the target area by receiving the cooling energy generated by the cooling generating unit 113 from the accommodating unit 111 and the insertion portion 210. In an alternative aspect, the tip 225 may come into contact and cool the target area by delivering the heat of the target area to the medical cooling device 10.

Although a shape, specifically a sectional shape of the tip 225 is shown as being circular, the scope of the present disclosure is not limited thereto, and the tip 225 may be formed in various shapes with which the cooling may be efficiently performed while contacting the target are. In addition, an area S1 of the tip 225 may be equal to or smaller than an area of the target area. With such an area S1, the removable cooling medium 20 may intensively cool the target area.

Further, as shown in FIG. 5C, the tip 225 may be formed of a convex surface protruding from the end E1 toward the outside or the target area. Since the anesthesia is generally performed on the human body, the tip 225 of the removable cooling medium 20 may come into contact with skin of the human body (i.e. the target area M). The skin is an organ covering the human body and consists of three layers disposed sequentially from the outside, that are epidermis k1, dermis k2 and subcutaneous fat layer k3. Similarly, the eye consists of conjunctiva k1, sclera k2, and uvea k3. In order for the anesthesia to be performed, sensory nerve should be also cooled. Thus, the removable cooling medium 20 may be provided with the convex tip 225 to allow the cooling power to be delivered to the dermis k2 where the nerve is located, so as to effectively anesthetize the target area.

A degree of convexity of the tip 225 may be larger than an epidermis thickness d1 of the target area M and may be smaller than a dermis thickness d2 of the target area M. In other words, a maximum protrusion height t1 of the tip 225 extending from the end E1 where the convexity of tip 225 starts toward the outside may be greater than the epidermis thickness d1 of the target area M, and may be less than the dermis thickness d2 thereof. With such a configuration, the detachable cooling medium 20 may concentrate force or pressure transmitted to the target region M on a central portion thereof, i.e. the tip 225 when coming in contact with the target region M and thus may effectively cool the nerves in the dermis k2 located near the central portion. Therefore, the cooling medium 20 may improve anesthesia performance near the central portion. It should be noted that the thicknesses of the epidermis and the dermis may be varied depending on the portion to be treated, but the configuration of the tip 225 as described above may cover such differences in the thicknesses to yield the effect as intended. In another example, the convex portion of the tip 225 is plural, thereby leading to multiple areas of the focused anesthetized portion of the target area M.

In another example, the tip 225 may be planar, or may be formed with a concave surface curved toward the insertion portion 210 to correspond to a curvature of the eyeball.

Meanwhile, the removable cooling medium 20 may be made of material having the high thermal conductivity to effectively transfer the cooling energy from the medical cooling device 10 to the target area M. For example, the removable cooling medium 20 may be made of gold (Au), silver (Ag), copper (Cu), aluminum (Al), and the like. Although the insertion portion 210 and the non-insertion portion 220 are shown as being formed integrally with each other, the insertion region 210 and the non-insertion region 220 may be manufactured as separate members and then be coupled with each other. In addition, the insertion portion 210 and the non-insertion portion 220 may be made of the same material, but may be made of different materials. Further, the tip 225 may be coated with material comprising a hydrophobic material to reduce formation of ice during cooling.

Here, the insertion portion 210 and the non-insertion portion 220 of the removable cooling medium 20 may serve as a heat flux distributor.

Referring back to FIGS. 5A and 5B, the insertion portion 210 may transfer the cooling energy transferred from the outer surface S2 to the tip 225. Further, the insertion portion 210 may extend in the axial direction AX1 to have a predetermined sectional area of the insertion portion 210 with regard to a sectional area of the tip 225. The sectional area of the insertion portion 210 may be taken along the axial direction AX1 and thus may corresponding to the outer surface S2 receiving the cooling energy. Further, the sectional area of the tip 225 may be taken along a direction normal to the axial direction and thus may corresponding to the surface S1 transferring the cooling energy to the target area if the tip 225 is formed flat. More specifically, in this case, the sectional area of the tip 225 may further correspond to the portion of the target area that is actually cooled. The sectional area of the insertion portion 210 with regard to the sectional area of the tip 225 may vary depending on material characteristics of the insertion area 210 and the non-insertion area 220. In an alternative aspect, the outer surface S2 of the insertion portion 225 may be greater than the surface S1 of the tip 225 and may be formed to have a predetermined areal ratio with regard to the surface S1. Likewise, the areal ratio may be dependent on the material of the removable cooling medium 20.

The areal ratio may be expressed as a ratio of a cooling accepting area to the target area, that is, a tissue cooling area. Such an areal ratio may be derived by a function using parameters such as an area in contact with the target area, a temperature of nerve, a depth of nerve, a thermal conductivity of material, and the like. This may be expressed in a following equation.

Areal ratio=cooling accepting area/tissue cooling area=$f$(nerve temp, nerve depth, material thermal conductivity)

The areal ratio of the area for collecting the cooling energy to the area for anesthetizing the target area may depend on a condition including at least any one of the area, the nerve depth, the nerve temperature, and the thermal conductivity of the detachable cooling medium, and may have a range of about 1.5 to 100. In other words, the area S2 of the insertion portion 210 may range from 1.5 times to 100 times the area of the area S1 of the tip 225.

Specifically, with respect to the anesthesia temperature T (° C.) for the nerve located at a certain depth d (mm) from a surface of the target area having a diameter $D_1$ (mm), the cooling temperature $T_s$, (C) for the surface of target area may be given by a following equation 1, and heat amount P (W) absorbed from the target area may be expressed by a following equation 2:

$$T_s = 36.1 - \frac{4c_1(e^{-0.25D_1^2 c_4} - 1)}{D_1^2 c_4} \quad \text{[Equation 1]}$$

wherein, $c_1$, $c_2$, $c_4$ is functions related to the diameter $D_1$, the depth d, and the temperature T, respectively, and may be further expressed as follows.

$$c_1 = 1.3752T - 17.2838d - 48.6\frac{1}{D_1} - 27.1$$

$$c_2 = \log\left(\frac{c_1}{T - 36.1}\right)^{1/d}$$

$$c_4 = 0.01\log(10c_1)$$

$$P = 0.0003927D_1^2 c_1 c_2 \quad \text{[Equation 2]}$$

$$P = \frac{0.11d - \pi Td/1000}{1 - 0.1d}$$

In order to satisfy the temperature $T_s$ and the heat amount P and realize the medical cooling device 10 having the body 100 of which a diameter is 50 mm, a length and an area of the heat dissipating unit 114 disposed in the body 100 may be determined and a length of the accommodating unit 111 may be determined.

With respect to the heat amount P transferred from the cooling medium 20 and the thermal conductivity K, a ratio (S2/S1=r) of a summation of the outer surfaces S2 of the insertion portion 210 to the contact area of the cooling medium 20 with the target area, that is, the area S1 of the tip 225 may be given by a following equation 3:

$$r = \frac{1834(36 - 2T_t)d \left(49.51\left(\sqrt{1 - \frac{0.00164D_1^2(36 - T_t)d}{1 - 0.1d}} - 0.98\right)^2 + \frac{0.0032D_1^2 d(36 - T_t)}{1 - 0.1d}\right)^2}{D_1 k(1 - 0.1d) \left(\frac{1.67d(T_t - 37.89) + 31.62}{1 - 0.1d} + \frac{0.102D_1^2 d(36 - T_t)}{1 - 0.1d} - 20.22\right)^2} \quad \text{[Equation 3]}$$

wherein $D_1$ indicates the diameter of the target area (mm), T indicates the anesthesia temperature for the nerve (° C.), and d indicates the depth of the nerve from the surface of the target area (mm).

The diameter $D_1$ is applied when the target area is circular, and with regard to other shapes of the target area, any corresponding equation may be applied to the equation 3 instead of $\pi D_1^2/4$ representing the circular area. Further, any sectional area of the cooling medium 20 may be inherently greater than the surface S1 of the tip 225, due the tapered configuration thereof.

Meanwhile, the heat dissipating unit 114 and the cooling generating unit 113 may be connected to each other via the heat transferring unit 116 comprising the heat pipe, the vapor chamber, or any pipe configured to allow the fluid to flow therein. If such a heat transferring unit 116 is applied, the ratio S2/S1 of the summation of the outer surface S2 to the surface S1 of the tip 225 may be limited by cooling amount per unit area of the cooling generating unit 113 $J_1$ (W/m$^2$) and thermal admittance per unit area of the unit 113 $A_1$(W/m$^2$-K). In view of such limitation, the ratio S2/S1 may be given in a following equation 4.

$$\frac{S2}{S1} \geq \frac{4P}{\pi D_1^2(J_1 - A_1\Delta T_1)} \qquad \text{[Equation 4]}$$

Here, $\Delta T_1$ is a temperature difference generated along a direction of a thickness of the thermoelectric element of the cooling generating unit 113, and may range from 30 K to 60K. P is given as the above equation 2. For example, when P=0.5 W, $J_1$=125000 W/m$^2$, $A_1$=2400 W/m$^2$-K, $\Delta T_1$=45 K, and $D_1$=5 mm, the ratio S2/S1 may be 1.5 approximately and thus the summation of the outer surface S2 may be 1.5 time the surface S1, at least.

Figure 5D:
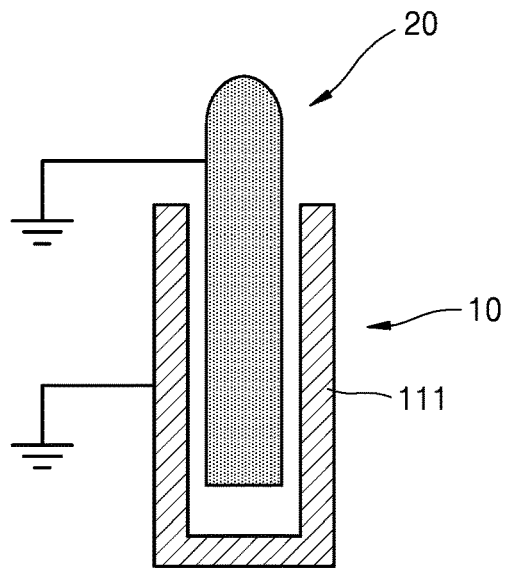

FIG. 5D is a conceptual and schematic view for explaining a method for grounding the removable cooling medium 20.

Since the removable cooling medium 20 is made of the material having the high thermal conductivity, electric conduction may occur well through the cooling medium 20. However, since the removable cooling medium 20 directly touches or contacts the target area of the human body, the medical cooling device 10, specifically the cooling medium 20 should have electrical stability.

Referring to FIG. 5D, the removable cooling medium 20 may be connected to a ground potential instead of a floating voltage. Further, the removable cooling medium 20 may be electrically coupled with the accommodating unit 111 and may have the same electric potential as the accommodating portion 111. That is, the removable cooling medium 20 may be not only thermally coupled with the accommodating portion 111 while being accommodated in the accommodating unit 111, but also be electrically coupled with the accommodating unit 111, and may have the same ground potential, because the accommodating unit 111 is connected to the ground potential. In such a configuration, the accommodating unit 111 may be connected to a component that may store electric charges, i.e, an electric capacitor or an electric storage. For example, the accommodating unit 111 may be connected to a battery so as to eliminate instability of the potential in the cooling medium 20 and the accommodating unit 111 caused by the external environment such as static charge or electricity by friction.

Physically, the heat transfer in metal may be carried out through movement of electrons in the metal. As described above, however, the removable cooling medium 20 may maintain a constant potential or voltage with regard to the accommodating unit 111. Therefore, the cooling medium 20 may absorb the heat of the target region while not creating the momentary movement of the electron to the target area from cooling medium 20, which cause a leakage of electricity to the target area. With such a configuration, the cooling medium 20 may minimize the risk of sparking or electric leakage to the target area and thus improve the electrical stability by maintaining the ground potential in the cooling medium 20.

More specifically, the cooling medium 20 may have thermal coupling as well as electric potential coupling with the accommodating unit 111 through a physical and direct contact with the accommodating unit 111. The electric potential coupling may be realized by a configuration that the cooling medium 20 has an electric potential corresponding to an electric potential of the accommodating unit 111. Such coupled potentials between the cooling medium 20 and the accommodating unit 111 may be stabilized by the electrical coupling of the cooling medium 20 and/or the accommodating unit 111 with a component configured to function as the electric storage. More specifically, the electric charge of the cooling medium 20/the accommodating unit 111 may be drained to the electric storage, and thus the potential may be regulated by the electric potential coupling as described above. The electric storage component may be the power source unit 191 such as the battery that is electrically connected to the cooling medium 20 and the accommodating unit 111, via an electric connector, for example, a wire Further, the electric-potential coupling between the cooling medium 20/the accommodating unit 111 and the power source unit 191 may be realized through the cooling generating unit 113, i.e., the thermoelectric element, instead of the wire. When the power supplying unit 191 serves as the electric storage and the electric-potential coupling between the power supplying unit 191 and the cooling medium 20/the accommodating unit 111 is made without any additional electric storage, such coupled potentials between the cooling medium 20 and the accommodating unit 111 may be stabilized within a range of operating electric-potential of the cooling generating unit 113. For more efficient stabilization of potential, the cooling medium 20 and/or the accommodating unit 111 may be coupled to a separate electric storage dedicated thereto, and this may also establish a further potential coupling between the cooling medium 20 and the accommodating unit 111. Further, the potential by the electric potential coupling may be controlled by a potential of an alternating current. Thus, the medical cooling device 10 may include the controlling unit 170 for controlling the potential of the alternating current.

The electric potential coupling of the cooling medium 10, the accommodating unit 111 and the component functioning as the electric storage may be established prior to the treatment by the cooling device 10, and thus may stabilize the potential in advance well before the contact of the cooling medium 20 with the target area. In some examples, The electric potential coupling of the cooling medium 10, the accommodating unit 111 and the component functioning as the electric storage may be achieved prior to the treatment and then may be maintained during the treatment. Due to such an electric-potential coupling, the cooling medium 20 may have the electrical stability, and thus may prevent the electric leakage to the target area and the electric shock caused thereby.

According to a preferred example, the cooling medium 20 may be physically in contact with the thermoelectric element of the cooling generating unit 113 via the accommodating unit 111, and then thermoelectric element may physically contract the heat dissipating unit 114. Further, the cooling medium 20 may be connected to the tip 225 in a physical manner. The cooling medium 20 may also be coated with or made of metal that has flatness better than 100 micrometer and excellent heat transferability. Therefore, due to such a physical coupling, a contacting portion of the medium 20 with the target area, i.e., the tip 225 may be adapted to thermally and electric-potentially coupled to the cooling medium 20, the accommodating unit 111, the thermoelectric element, and the heat dissipating unit 114.

Figure 5E:
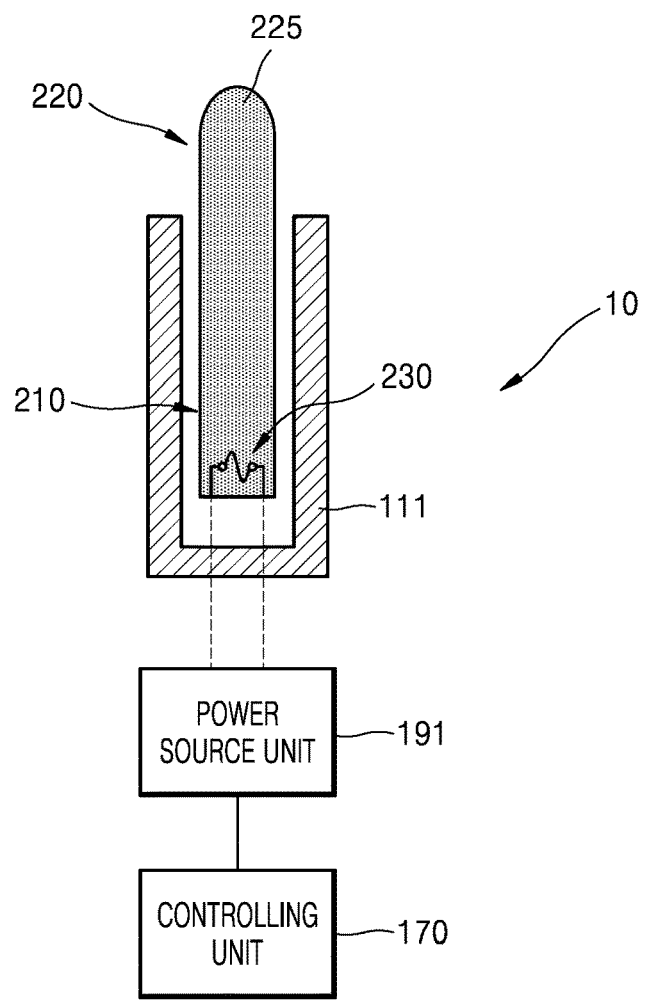

FIG. 5E is a conceptual and schematic view for explaining a reuse prevention unit 230 of the removable cooling medium.

Referring to FIG. 5E, the removable cooling medium 20 may further include a reuse preventing portion 230 that is electrically connected to the medical cooling device 10 and may provide information related to reuse to the medical cooling device 10.

As the removable cooling medium 20 is in direct contact with the target area, infection by bacteria or other reasons may occur if the cooling medium 20 contacts the target area and then is reused to another patient. The removable cooling medium 20 according to an example of the present disclosure may be provided with the reuse prevention part 230 so as to be disposable, and thus may secure sterility and hygiene.

For example, the reuse prevention unit 230 may include a fuse that is electrically connected to the medical cooling device 10. More specifically, the reuse preventing unit 230 is connected to the power source unit 191 of the medical cooling device 10 to form a closed circuit. The controlling unit 170 may control the power source unit 191 to apply more than a preset current to the reuse prevention unit 230 when the cooling of the removable cooling medium 20 is completed. As a result, the fuse of the reuse prevention portion 230 is blown out to open the circuit, and in that case, the controlling unit 170 may recognize the opened circuit and may control the power source unit 191 not to provide the current to the cooling device 10. Therefore, with such a prevention unit 230, the cooling medium 20 may not be reused.

Meanwhile, the reuse prevention unit 230 (i.e., the fuse) may be configured to be electrically isolated from the cooling medium 20, while still capable of cutting off the current when the fuse is broken. With such a configuration, the excessive current for blowing the fuse may not leak to the target area via the cooling medium 20. In addition, the controlling unit 170 may cause the fuse to be blown out after a preset time period after an alarm informing the completion of the cooling is first provided. Accordingly, the user may have a sufficient time period and may be induced to remove the cooling medium 20 from the target before the excessive current is applied to blow the fuse. For these reasons, the electric shock may be prevented while the prevention unit 230 is destroyed. Alternatively, while the cooling generating unit 113 reaches a target cooling temperature, more specifically, before an alarm that informs the device 10 is ready to cool the target is provided i.e., prior to contacting the medium 20 to the target area, the controlling unit 170 may blow the fuse of the prevention unit 230 and thus may minimize the electric shock of the target area.

The controlling unit 170 may provide an electrical signal to the reuse prevention unit 230 of the removable cooling medium 20 which is inserted into the medical cooling device 10. If the electric signal is returned to the controlling unit 170, this indicates the fuse is not blow out, and the cooling medium 20 is in a first use. Therefore, the controlling unit 170 may control the cooling device to operate. Alternatively, when the cooling medium 20 in which the fuse is broken is inserted, the controlling unit 170 may determine that the cooling medium 20 is being reused because any electric signal from the controlling unit 170 is not returned thereto due to the opened circuit by the blown fuse. Thus, the controlling unit 170 may control the medical cooling device 10 not to operate.

In another example, the removable cooling medium 20 includes a chip such as a radio frequency identification (RFID) chip or an integrated circuit (IC) chip. The medical cooling device 10 may read information on the chip and thus may determine whether the cooling medium 20 is reused or not.

As still another example, the removable cooling medium 20 may be allowed to be used for a preset number of times. That is, after the predetermined number of times, for example, ten times, the cooling medium 20 may be replaced.

In this case, a fluid medicine amount to the use of the cooling medium 20 for such a preset number of times may be stored in a reservoir in the medium 20 that will be described below. Alternatively, once used, the cooling medium 20 may be detached from the medical cooling device, filled with the medicine, and then inserted again into the medical cooling device 10.

V. Cartridge Type Removable Cooling Medium

Hereinafter, a medical cooling system or device having a medicine injection function according to another example of the present disclosure will be described in detail with reference to FIGS. 6A to 6G. The medical cooling system or device according to another example may primarily cool the target area and may further provide the medicine to the target area. Hereinafter, for convenience of description, the same reference numerals will be assigned to the same components as those of the examples as described above, and any repeated description for such same components will be omitted.

FIGS. 6A to 6G are views for explaining a medical cooling device and a removable cooling medium having the medicine injection function.

Figure 6A:
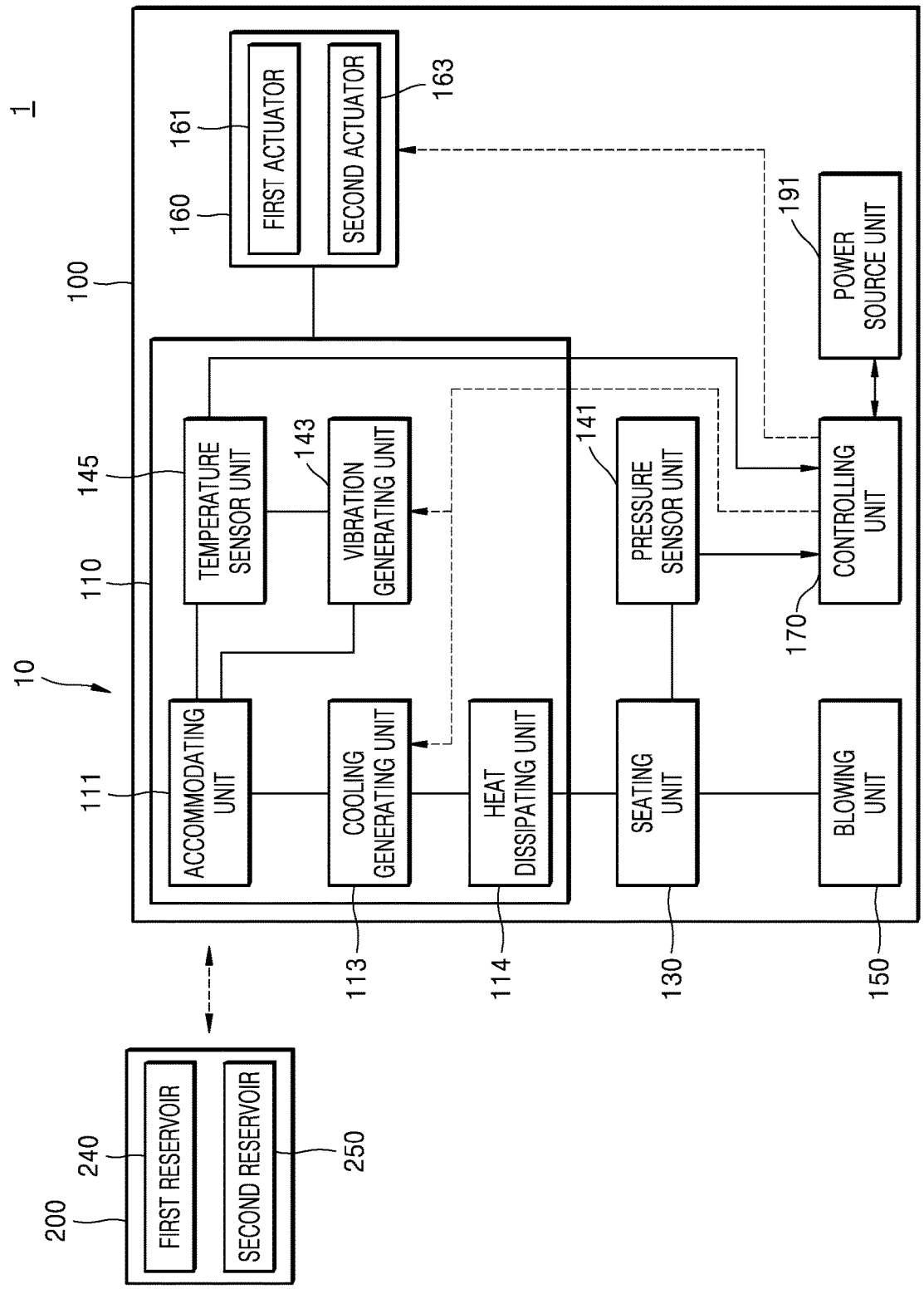
FIGS. 6A to 6G are views illustrating examples of a medical cooling device and a removable cooling medium having a medicine injection function.
Figure 6B:
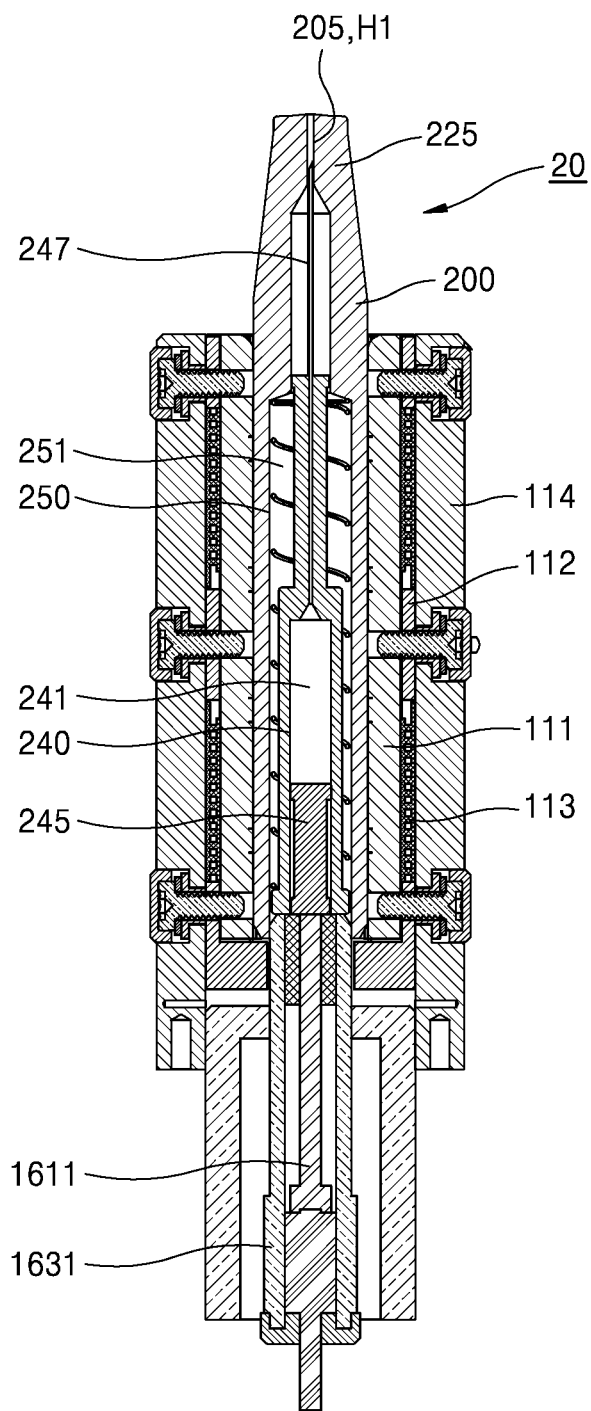

FIG. 6A is a block diagram of the medical cooling system according to another example of the present disclosure, and FIG. 6B is a sectional view for showing an example of the removable cooling medium of the medical cooling system. Further, FIG. 6C to FIG. 6F are conceptual and schematic views sequentially illustrating a medicine injection process of the removable cooling medium of FIG. 6B.

Referring to FIGS. 6A and 6B, a medical cooling system 1 according to another example of the present disclosure may include a medical cooling device 10 and a removable cooling medium 20 accommodated in the medical cooling device 10.

The medical cooling device 10 may include a body 100, a cooling medium accommodating unit 111, a cooling generating unit 113, a heat dissipating unit 114, a temperature sensor unit 145, a blowing unit 150, a power source unit 191 and a controlling unit 170. These components are already discussed above with reference to FIGS. 2A-2K, which will be also further referred to along with FIGS. 6A and 6B. The medical cooling device 10 in this example may further include an injecting unit 160.

The body 100 may form an exterior of the medical cooling device 10, and the components may be housed therein.

The accommodating unit 111 may accommodate the cooling medium 20 and may be thermally coupled with the cooling medium 20 to transfer the cooling energy or power from the cooling generating unit 113 to the cooling medium 20. The accommodating unit 111 may be made of metallic material having a high thermal conductivity to efficiently transfer the cooling energy. The accommodating unit 111 may function as a cooling distributor for dispersing or distributing over a large surface or area of the cooling medium 20 that corresponds to the insertion portion 210, the cooling energy collected from a relatively small surface or area of the cooling generating unit 113.

The cooling generating unit 113 may be disposed on a surface 111B (i.e. the second surface), which is opposite to the contact surface 111A (i.e. the first surface) of the divided member 1111, and may supply the cooling energy or the cooling power to the accommodating unit 111. The cooling generating unit 113 may comprise any mechanism capable of supplying the cooling energy to the accommodating unit 111 and may include one or more cooling elements capable of generating the cooling energy.

The heat dissipating unit 114 may be configured to discharge the heat emitted from the cooling generating unit 113 to the outside. The heat dissipating unit 114 may be also referred to as the heat sink, the heat emitting unit, the heat radiating unit, and so on. The heat dissipating unit 114 may be made of thermally conductive material to efficiently discharge the heat generated while the cooling generating part 113 produces the cooling energy.

The blowing unit 150 may suck the outside air into the first end portion a of the body 100 to cool the heat dissipating unit 114 and may discharge the air to the second end portion b located in a rear of the first end portion a. The blowing unit 150 may include the fan, but is not limited thereto. Any device such as a compressed air tank, a blower, or the like capable of producing the unidirectional air flow may be applied.

When the heat transferring medium 116 is applied to thermally connect the cooling generating unit 113 and the heat dissipating unit 114, the air flow from the blowing unit 150 may be generated in a direction not parallel to the longitudinal direction extending from the first end a to the second end b of the body 100 to pass through the heat dissipating unit 114.

The temperature sensor unit 145 may be configured to sense the temperature of the cooling medium 20 or the accommodating unit 111. If the temperature sensor unit 145 comprises a contact sensor, such a unit 145 may be configured to be disposed at the cooling unit 110 to directly contact the accommodating unit 111 or the cooling medium 20. For example, the plurality of units 145 may be placed on the medium 20 and unit 111, respectively, Alternatively, the unit 145 may be disposed on a portion of the unit 111 that contracts the medium 20, such as the contact surface 111A such that sensing the temperatures of both medium 20 and the unit 111 is enabled by the single unit 145. Otherwise, the temperature sensor unit 145 may be configured to indirectly contact the medium 20 or the unit such that the temperature of the medium 20 or the unit 111 may be sensed by contact and sensing the component in direct contact with the medium 20 or the unit 111. When the cooling medium 20 is configured to be replaceable, the temperature sensor unit 145 for measuring the temperature of the cooling medium 20 may be sensed by a non-contact temperature sensor, for example, an infrared ray sensor. Further, additional sensor units may be provided to the cooling unit 110 to sense temperatures of other components (e.g., the units 113 and 114) and an overall inner temperature of the device 10.

The injecting unit 160 may configured to apply pressure to the cooling medium 20 to discharge a fluid medicine in a reservoir provided in the cooling medium 20. In the present disclosure, the fluid medicine may include a liquid medicine and a gas medicine. The injecting unit 160 may include an actuator. In one example, the injecting unit 160 may include a first actuator 161 and a second actuator 163. Further, the injecting unit 160 may include a first injecting unit 1611 configured to perform a linear movement in an actuating direction of the first actuator 161 and a second injecting unit 1631 configured to perform a linear movement in an actuating direction of the second actuator 163. Meanwhile, at least one of a driving shaft (or axis) of the first actuator 161 and a driving shaft (or axis) of the second actuator 163 may be coupled with a moving shaft (or axis) by which the first injecting unit 1611 or the second injecting unit 1631 moves, using a link. The link may serve to convert rotational motion of the first actuator 161 or the second actuator 163 into a linear motion, and more than one link may be provided. With such a link, the driving shaft (or axis) of the first actuator 161 or the second actuator 163 may not be parallel to the moving shaft (or axis) of the first injecting unit 1611 or the second injecting unit 1631, and the movements of the first injecting unit 1611 and the second injecting unit 1631 may be correlated and coupled. Alternatively, the driving shaft (or axis) of the first actuator 161 or the second actuator 163 may comprise the link as described above. As well shown in FIG. 6B, the cooling medium 20 may have an opening through which the injecting unit 160 may reach inside the medium 20, specifically may be connected to components inside the medium 20 to apply the pressure the fluid medicine within the medium 20. Further, if necessary, the accommodating unit 111 and/or the coupling unit 112 each may also have an opening communicating with the opening of the cooling medium 20 to allow the injecting unit 160 to reach inside of the medium 20. In light of a configuration as described above, the injecting unit 160 as a whole may be considered to be a thruster pressing the cooling medium 20 and inner components thereof, and the first and second injecting members 1611 and 1631 may be considered to be a plunger, a piston, a movable rod and the like.

The controlling unit 170 may control the operation of the components provided in the medical cooling device 10. The controlling unit 170 may control the operation of the cooling generating unit 113 based on the temperature sensed by the temperature sensor unit 145 or may control the time period for performing the anesthesia based on the pressure sensed by the pressure sensor unit 141. In addition, the controlling unit 170 may discharge the medicine from the cooling medium 20 to the outside by controlling the injecting unit 160 according to a preset control procedure.

A detailed configuration of the injecting unit 160 and a method for injecting the medicine into the target area by controlling the injecting unit 160 will be described later.

Meanwhile, the removable cooling medium 20 may include a main body 200 and a first reservoir 240.

The main body 200 may be detachably installed to the medical cooling device 10. The main body 200 may refer to a body of the cooling medium 20 including the insertion portion 210 and the non-insertion portion 220 as described above. The main body 200 may cool the target area with being in contact therewith and may discharge or inject the medicine stored therein into the target area. Therefore, the cooling medium 20 in this example may have the same components for cooling the target area as the cooling medium 20 as above, and thus any repeated description thereto will be omitted.

The main body 200 may have the tip 225 as shown in FIG. 5A or FIG. 5B at its one end adjacent to the target area. A discharging portion 205 may be disposed at the tip 225. A needle hole may be formed in the tip 225 with passing through the main body 200 to allow an injecting needle 247 to pass therethrough. The discharging portion 205 of a predetermined diameter may be disposed at a position corresponding to the needle hole. The discharging portion 205 may have a tube shape and may serve to hold the needle 247.

The first reservoir 240 may store the first fluid medicine 241 to be injected into the target area, and may be provided movably within the main body 200. Although not shown in detail, a hollow portion may be formed in the body 200 such that the first reservoir 240 may be movable in such a hollow portion.

Specifically, the first reservoir 240 may include the injecting needle 247 for injecting the first fluid medicine 241 at one end thereof. The needle 247 may be configured to be coupled to one end of the first reservoir 240 and to have an inner space thereof communicating with the first reservoir 240. The needle 247 may be arranged to be parallel to the discharging portion 205 and may move together with the first reservoir 240 when the first reservoir 240 moves along an axial direction of the body 200. With such a configuration, the injecting needle 247 may actually function as a mobile injecting needle.

A diameter of the injecting needle 247 may be smaller than the diameter of the discharging portion 205, to minimize heat transfer between the injecting needle 247 and the discharging portion 205. An end of the injecting needle 247 may pass through the discharging portion 205 and may be exposed to the outside when the first reservoir moves toward the tip 225. While the injecting needle 247 moves along the needle hole (i.e. the discharging portion 205), the needle 247 may not be in contact with the tip 225.

Meanwhile, the first reservoir 240 may include an injector 245 disposed on a central axis of the reservoir 240. The injector 245 may be moved by an actuator that is operably connected to, i.e., interlocked with the injector 245 when the removable cooling medium 20 is mounted on the medical cooling device 10. The first reservoir 240 may push out the first fluid medicine 241 by moving the injector 245 disposed therein using the actuator of the medical cooling device 10.

In another example, the removable cooling medium 20 may further include a second reservoir 250 for storing a second fluid medicine 251. The second reservoir 250 may be arranged in line with the first reservoir 240 along the axial direction of the main body 200. The second reservoir 250 may be disposed closer to the tip 225 than the first reservoir 240. With the configurations of the first and second reservoirs 240 and 250 as described above, the removable cooling medium 20 may inject a plurality of fluid medicines into the target area. More specifically, the second reservoir 250 may push out the second fluid medicine 251 stored therein by moving the first reservoir 240. As shown, the first reservoir 240 may comprise a separate member or container movably inserted into the cooling medium 20. In contrast, the second reservoir 250 may be formed inside the cooling medium 20 by a wall thereof, not using any separate or additional member. More specifically, the second reservoir 250 may be relatively defined by the wall of the cooling medium 20 and the first reservoir 240. That is, the second reservoir 250 may comprise a hollow portion of the coiling medium 20 that is configured to movably receive the first reservoir 240 therein.

Here, the first fluid medicine 241 and the second fluid medicine 251 may be different from each other. For example, the first fluid medicine 241 may comprise a therapeutic agent, and the second fluid medicine 251 may comprise a disinfecting agent. The therapeutic agents may be, for example, an agent such as ranibizumab, bevacizumab, and aflibercept. The disinfecting agent may be a mixture including at least one of isopropyl alcohol, povidone-iodine, and benzalkonium chloride. More specifically, isopropyl alcohol may be 70% isopropyl alcohol, and povidone-iodine may be a 5% solution of povidone iodine. In addition, benzalkonium chloride may be 0.4% benzalkonium chloride.

The removable cooling medium 20 may include a sealing layer provided between the discharging portion 205 and the first reservoir 240 or between the discharging portion 205 and the second reservoir 250. The sealing layer may serve to prevent the second fluid medicine 251 stored in the second reservoir 250 or the first fluid medicine 241 stored in the first reservoir 240 from leaking out through the discharging portion 205 before the injection. For example, the sealing layer may be disposed at an inlet of the discharging portion 205 communicating with the first or second reservoir 240 or 250, particularly with an out of the first or second reservoir 240 or 250.

Hereinafter, the injection process by the removable cooling medium 20 will be described with reference to FIGS. 6C to 6F.

Figure 6C:
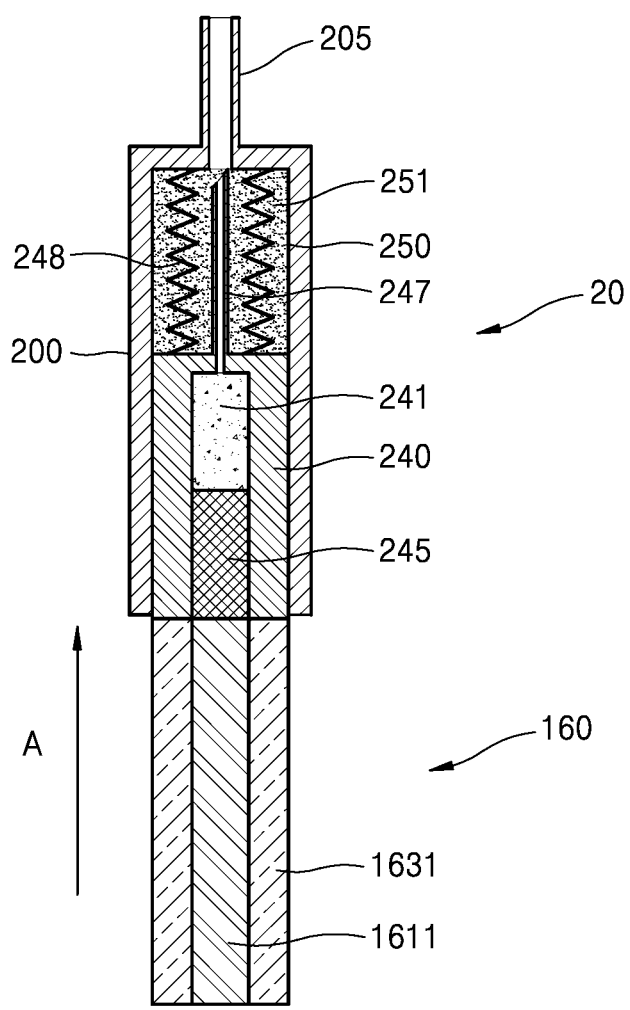

The removable cooling medium 20 may be in a state as shown in FIG. 6C when first inserted into the medical cooling device 10. When the second injecting units 1631 of the injecting unit 160 linearly move in a direction indicated by an arrow A as shown in FIG. 6C, the first reservoir 240 and the injecting needle 247 may move together in the same direction with being pushed by the second injecting units 1631. The first injecting unit 1611 may be coupled to the injector 245 and thus may move together along with movement of the first reservoir 240. Alternatively, the first injecting unit 1611 may move independently by driving the first actuator 161 to keep pace with movement of second injecting unit 1631. Further, while the needle 247 is inserted into the discharging portion 205, the sealing layer disposed between the second reservoir 250 and the discharging portion 205 may be destroyed by the needle 247. Therefore, the second fluid medicine 251 in the second reservoir 250 may be injected into the target area through the discharging portion 205 with being pushed by the first reservoir 240.

Figure 6D:
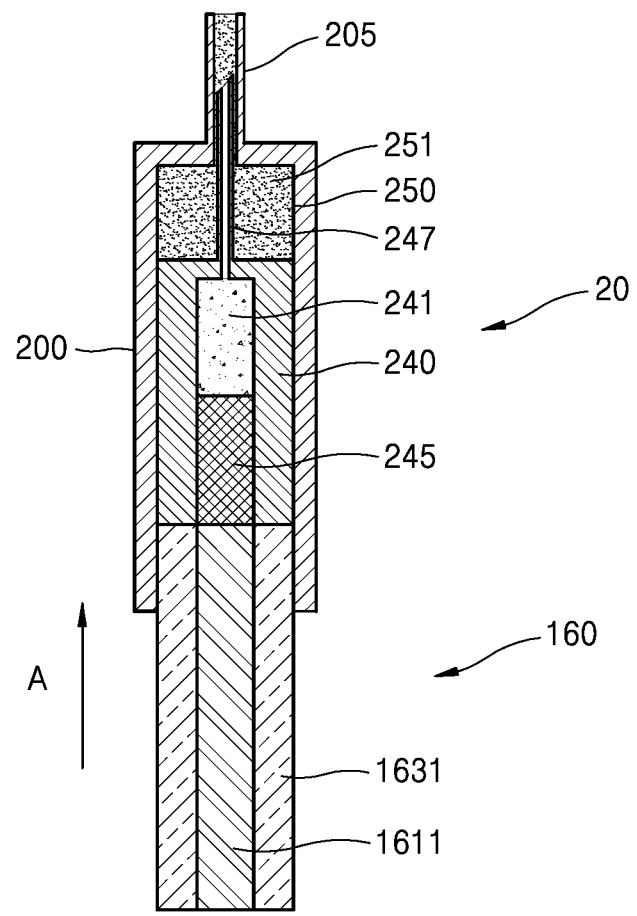

As the second fluid medicine 251 contains a disinfecting agent, the target area may be disinfected before the injection of the first fluid medicine 241. After the first reservoir 240 moves by a predetermined distance and the needle 247 destroys the sealing layer, i.e., while the second fluid medicine 251 is being discharged, the second injecting unit 1631 configured to move the first reservoir 240 may stop and standby for a predetermined time period, example, 20 seconds, such that the needle 247 protruding out of the medium 20 is not inserted into the target area, as shown in FIG. 6D. Therefore, the target area may be sufficiently disinfected before inserting the needle 247 into the target area. Then, the second injecting unit 1631 may continue to further move to push the first reservoir 240 and the needle 247, and then the needle 247 may be inserted into the target area.

Figure 6E:
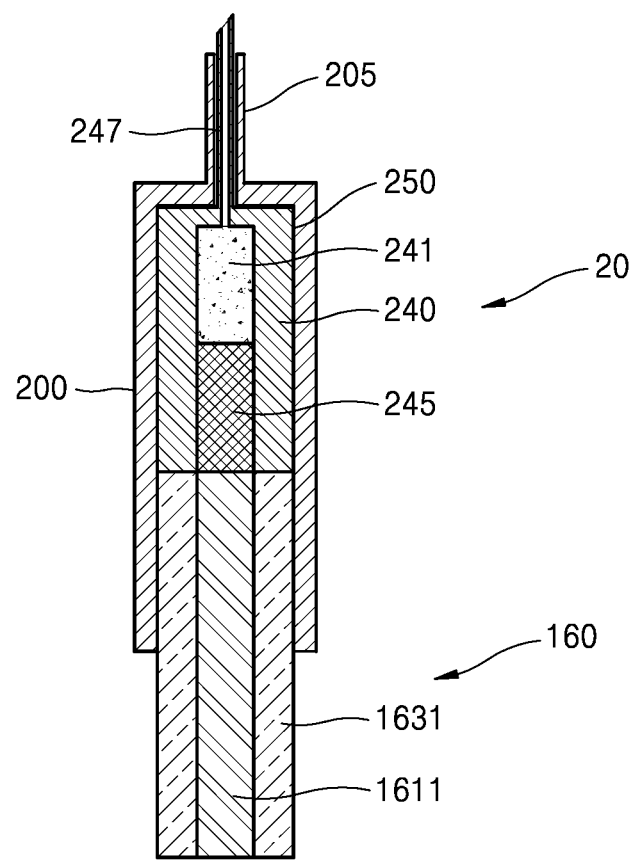

More specifically, when the second actuator 163 is further driven and the second injecting unit 1631 further moves linearly in the direction of the arrow A as shown in FIG. 6D, the first reservoir 240 and the injection needle 247 may further move together in the same direction with being pushed by the second injecting unit 1631 as shown in FIG. 6E. The first injecting unit 1611 may be coupled to the injector 245 and thus may move together along with movement of the first reservoir 240. Alternatively, the first injecting unit 1611 may move independently by driving the first actuator 161 to keep pace with movement of second injecting unit 1631. Thus, a portion of the needle 247 may protrude out of the cooling medium 20 to be inserted into the target area.

Figure 6F:
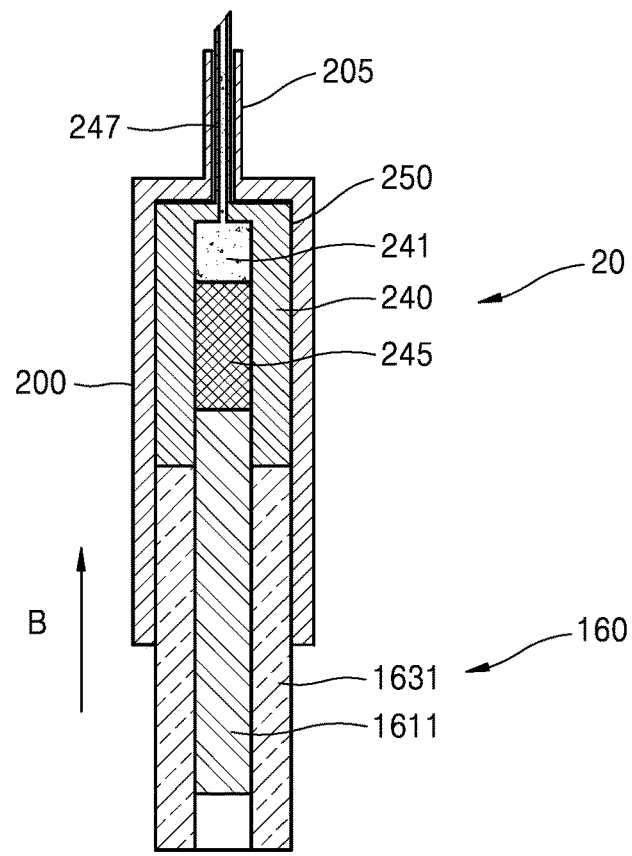

Then, when the first actuator 161 is driven and the first injecting unit 1611 linearly moves in a direction of an arrow B as shown in FIG. 6F, the first injecting unit 1611 may pressurize the first reservoir 240, specifically, may push the injector 245 disposed in the first reservoir 240. Accordingly, the first fluid medicine 241 in the first reservoir 240 may be injected into the target area through the injection needle 247. In this instance, only the first injecting unit 1611 may move, while the second injecting unit 1631 may stop to prevent the second fluid medicine 251 from being discharged during the injection of the first fluid medicine 241. Alternatively, the first and second injecting units 1611 and 1631 may move together in this stage or step to provide the first and second fluid medicines 241 and 251 simultaneously.

After the injection of the first fluid medicine 241 is completed, the first and second injecting units 1611 and 1631 may linearly return in an opposite direction and the needle 247 and the first reservoir 240 may be located in an original portion as shown in FIG. 6C. Further, as shown in FIG. 6C, a restoring mechanism 248 such as the spring may be additionally provided in order to facilitate the return of the needle 247 and the first reservoir 240. More specifically, the restoring mechanism 248 may be provided between the first reservoir 240 and a portion of the body 200, for example, the tip 225. The restoring mechanism 248 may be compressed by the first reservoir 240 during the injection of the second fluid medicine 251 to store elastic energy. Then, when the first and second injecting units 1611 and 1631 move back after the injection of the fluid medicines 241 and 251 is completed, the restoring mechanism 248 may be restored and push back the first reservoir 240 along with the needle 247 and the injector 245 by yielding the stored elastic energy to facilitate the returning of these components 240, 245, and 247 even including the injecting units 1611 and 1631 to the original position.

Figure 6G:
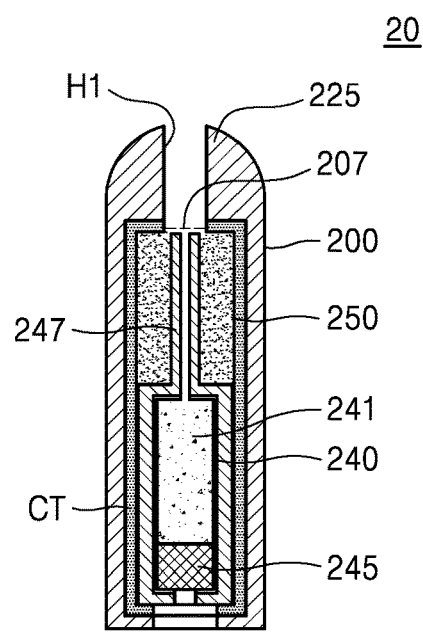

FIG. 6G is a sectional view showing another example of the removable cooling medium of the medical cooling system.

Referring to FIG. 6G, the removable cooling medium 20 of another example may not include the discharging portion 205 as shown in FIGS. 6C-6F. Instead, only a needle hole H1 through which the injecting needle 247 pass may be formed at the tip 225 of the cooling medium 20.

The first reservoir 240 may store the first fluid medicine 241 to be injected into the target area, and may be disposed movably within the main body 200. The main body 200 may include a guide portion for receiving the first reservoir 240 therein and guiding the first reservoir 240 to move along the axial direction of the main body 200. The guide portion may be simply the hollow portion within the cooling medium 20 and thus may comprise the wall of the medium 20 with introducing no additional member as described above referring to FIGS. 6A-6F. Alternatively, as shown in FIG. 6G, the guide portion may comprise any separate member installed within the cooling medium 20. This separate member may also form the second reservoir 250 in which the second fluid medicine 251 is stored. More specifically, in this instance, the second reservoir 250 as the guide portion may comprise a container defining a predetermined space and installed within the cooling medium 20. Such a second reservoir 250 may accommodate the first reservoir 240 in the space therein. The first reservoir 240 may closely contact an inner surface of the second reservoir 250 to be stably guided while moving.

The removable cooling medium 20 may be formed of the material having the high thermal conductivity to effectively cool the target area and may be provided with a device for preventing freezing of the medicine contained therein.

In one example, the first reservoir 240 may be made of the material having the thermal conductivity lower than that of the body 200 to prevent the freezing of the medicine stored therein. The first reservoir 240 may be made of the material having the thermal conductivity of 20 W/m-K or less.

In another example, the material having the thermal conductivity lower than that of the body 200 may be coated on a surface CT of the body 200 that encloses the guide portion (i.e., the second reservoir 250) and the first reservoir 240. This surface CT may be also a surface contacting or defining the guide portion (i.e., the second reservoir 250). Alternatively, such a coating may be provided on an inner surface of the guide portion (or the second reservoir 250) that faces or encloses the first reservoir 240, specifically contacts the first reservoir 240. In this implementation, when the guide portion is formed by the wall of the medium 20, the coating may be provided on an inner surface of the medium 20 contacting the first reservoir 240. As the guide portion (i.e., the second reservoir 250) forms a passage through which the first reservoir 240 moves, the coating as described above may reduce the cooling energy transferred to the first reservoir 240 to prevent the freezing of the first fluid medicine 241. This coating may also hinder the freezing of the second fluid medicine 251. In the above configuration, the coating may be made of the material having the thermal conductively of 20 W/m-K or less.

Further, a contacting surface of the guide portion (i.e., the second reservoir 250) with the first reservoir 240 may be minimized to reduce the cooling energy transferred from the main body 200 to the first reservoir and fluid medicine 240 and 241. For example, the guide portion (i.e., the second reservoir 250) may have the surface contacting the first reservoir 240 that is maintained 20 mm$^2$ or less. For example, the small contacting surface area of the first reservoir 240 with the guide portion (i.e., the second reservoir 250) may be realized by the patterned surface CT such as groove pattern, or by extending the first reservoir 240 to outside the guide portion (i.e., the second reservoir 250) and having a large portion of the first reservoir 240 outside the guide portion (i.e., the second reservoir 250).

When the removable cooling medium 20 includes the second reservoir 250, the second reservoir 250 may have the same configuration as the guide portion as describe above. In other words, when the guide portion is configured to have a body made separated from the body 200 with defining the predetermined space and is installed within the body 200, such a guide portion may also function as the second reservoir 250 storing the second fluid medicine 251, as already discussed above. With such a configuration, the first reservoir 240 may be disposed inside such a second reservoir 250 (i.e., the guide portion) and may move along the axial direction of the main body part 200 to push out the second fluid medicine 251 to the outside.

The second fluid medicine 251 may be discharged to the outside through the needle hole H1. The removable cooling medium 20 may include a sealing layer 207 provided between the needle hole H1 and the first reservoir 240 or between the needle hole H1 and the second reservoir 250. The sealing layer 207 may serve to prevent the second fluid medicine 251 stored in the second reservoir 250 or the first fluid medicine 241 stored in the first reservoir 240 from leaking out through the needle hole H1 before the injection. More specifically, as shown in FIG. 6G, the sealing layer 207 may be disposed at one end of the second reservoir 250 that is adjacent to the tip 225. The sealing layer 207 may be disposed an outlet of the second reservoir 250 or an inlet of the needle hole H1 to be penetrated by the needle 247 configured to selectively move toward the outside of the cooling medium 20. The configuration of the sealing layer 207 as described above may be applied to the cooling medium 20 as shown in FIGS. 6A-6F to substantially yield the same effect and advantage.

VI. Injecting Unit and Actuator

Hereinafter, the injecting unit of the medical cooling device will be described in detail with reference to FIGS. 7A to 7E.

Figure 7A:
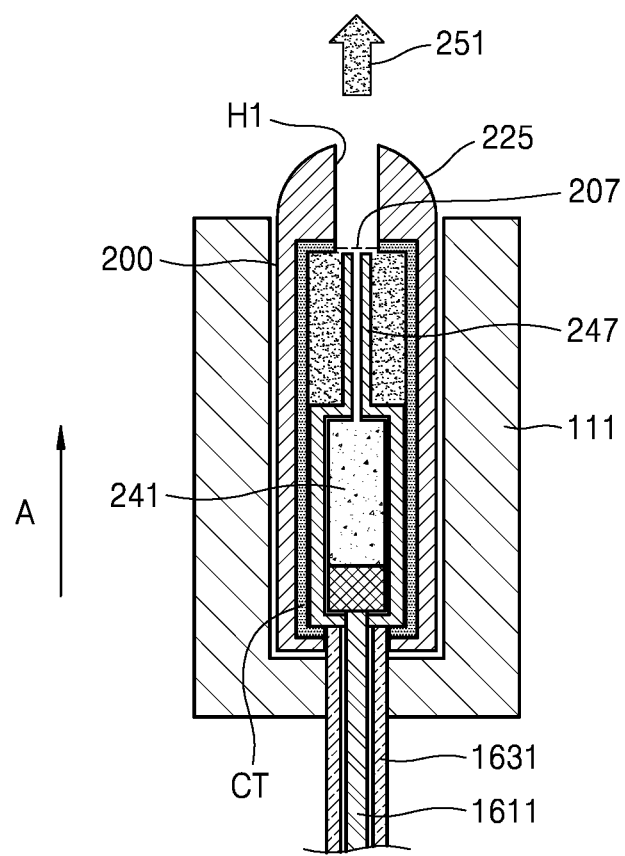
FIGS. 7A to 7E are views illustrating examples of an injecting unit and an actuator of the medical cooling device.
Figure 7B:
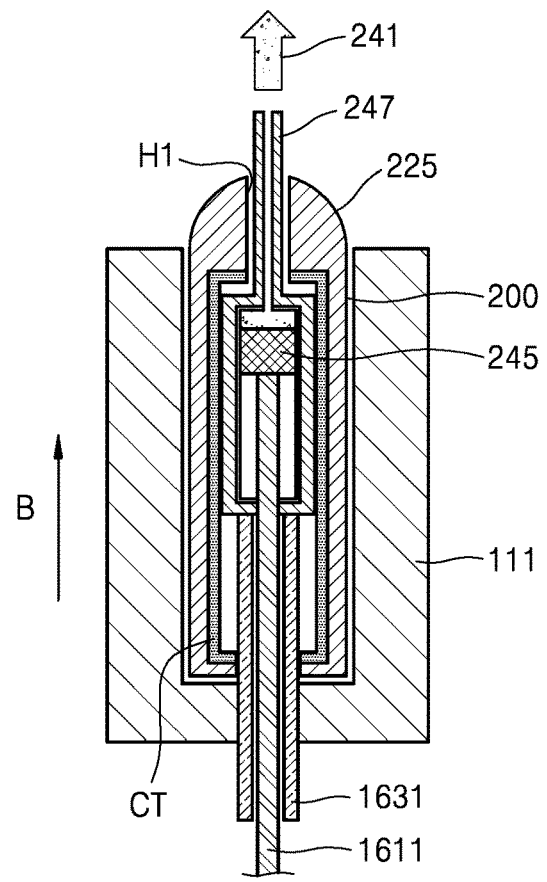
Figure 7C:
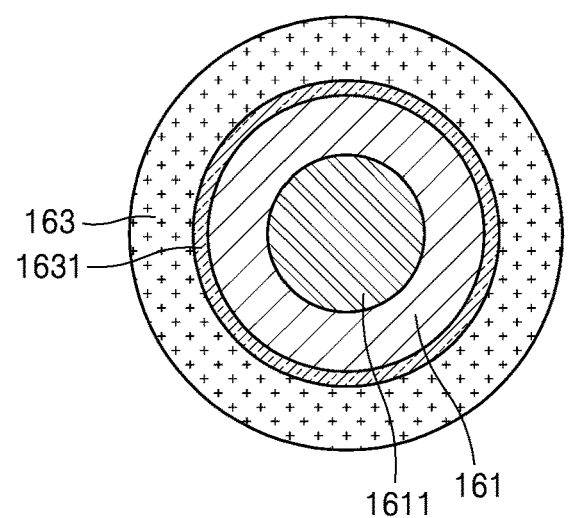
Figure 7D:
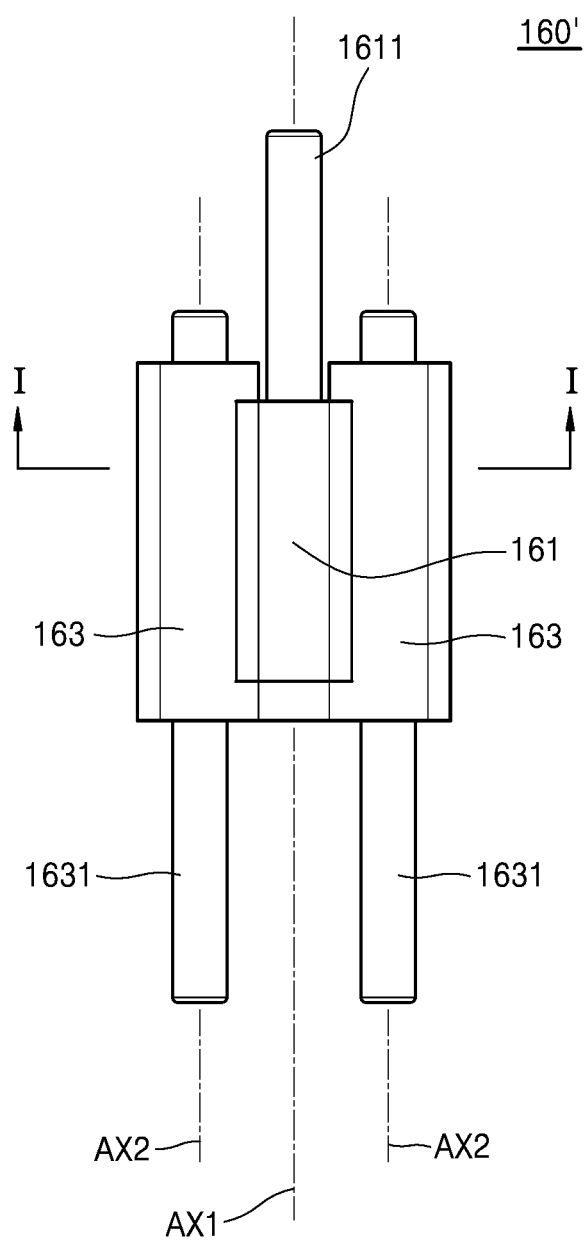
Figure 7E:
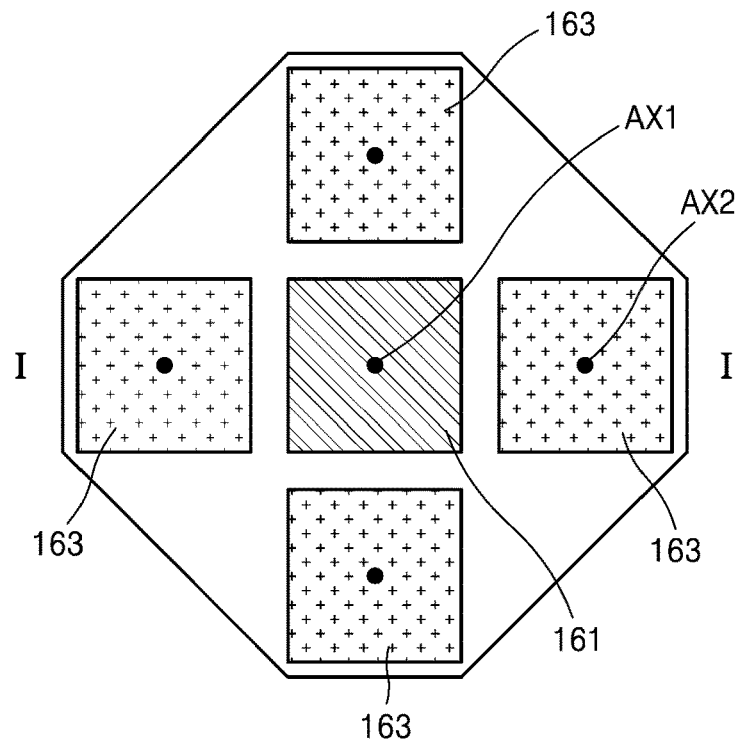

FIGS. 7A and 7B are views for describing features related to the injecting unit and the actuator of the medical cooling device. FIG. 7C is a sectional view schematically showing one example of the injecting unit of FIG. 7A. Further, FIG. 7D is a view showing another example of the injecting unit of FIG. 7A, and FIG. 7E is a sectional view schematically showing the injecting unit of FIG. 7D taken along a line I-I. Hereinafter, the medicine injection process of the cooling medium 20 according to actuator operation will be described with reference to FIGS. 7A and 7B.

First, the removable cooling medium 20 may be inserted into the accommodating unit 111 of the medical cooling device 10, as shown in FIG. 7A. In a configuration as shown in FIG. 7A, when the second actuator 163 is driven and the second injecting unit 1631 linearly moves in a direction of an arrow A, the second injecting unit 1631 and the first injecting unit 1611 may move together and may push the first reservoir 240 toward the outside of the medium 20, specifically toward the tip 225. The first reservoir 240, while moving, may push the second fluid medicine 251 out of the cooling medium 20. At the same time, the injecting needle 247 disposed at one end of the first reservoir 240 may move together in the same direction, and may be inserted into the needle hole H1 to tear the sealing layer 207, while moving. Accordingly, the second fluid medicine 251 contained in the second reservoir 250 may be provided to the target area through the needle hole H1, as shown in FIG. 7B.

Further, when the first actuator 161 is driven and the first injecting unit 1611 linearly moves in a direction of an arrow B, the first injection unit 1611 may press the injector 245 disposed inside the first reservoir 240. In this instance, only the second injecting unit 1611 may move, while the second injecting unit 2631 may stop. Accordingly, as shown in FIG. 7B, the first fluid medicine 241 contained in the first reservoir 240 may be injected into the target area through the injecting needle 247.

Referring to FIGS. 7A to 7C, the injecting unit 160 may function as a driving unit capable of providing a plurality of medicines to the affected area, i.e., the target area, using the components in the cooling medium 20. That is, the injecting unit 160 may serve as a multi-medicines dispenser. Such a multi-medicines dispenser may sequentially discharge the second fluid medicine 251 of the second reservoir 250 and the first fluid medicine 241 of the first reservoir 240.

The injecting unit 160 may discharge the first fluid medicine 241 of the first reservoir 240 provided in the removable cooling medium 20 by applying pressure to the medium 20. The injecting unit 160 may include the actuator that generates the force of the pressure to be applied to the removable cooling medium 20 in response to a control signal applied before or after cooling the target area using the removable cooling medium 20. More specifically, the actuator may include a second actuator 163 and a first actuator 161 that may sequentially apply the pressure to the removable cooling medium 20 according to the applied control signal.

As shown in FIG. 7C, the injecting unit 160 may include the first injecting unit 1611 that may be disposed on an extension line of the center axis of the accommodating unit 111 and may be configured to move inside the first reservoir 240 with being connected to the first actuator 161. In Addition, the injecting unit 160 may further include the second injecting unit 1631 that may be coaxial with the first injecting unit 1611 and may receive the first injecting unit 1611 therein. The second injecting unit 1631 may be connected to the second actuator 163 and may move into the cooling medium 20, i.e., the second reservoir 250 to push and thus move the first reservoir 240.

In one example, the first actuator 161 and the second actuator 163 may be coaxial linear actuators, and each of the first and second actuators 161 and 163 may control linear movement thereof on the coaxial axis independently. For example, the first actuator 161 and the second actuator 163 may be piezoelectric actuators. That is, the first actuator 161 and the second actuator 163 are arranged so as to be able to perform the linear motion along the same axis.

The first actuator 161 and the second actuator 163 may be controlled by the controlling unit 170. By driving the first actuator 161 and the second actuator 163, the motions or movements of the first and second injecting units 1611 and 1631 may be controlled, respectively. That is, the first and second injecting units 1611 and 1631 may comprise driving shafts of the first and second actuators 161 and 163, respectively, that linearly move along the same axis. Further, since the first injecting unit 1611 is disposed within the second injecting unit 1631, when the second injection portion 1631 is moved toward the tip 225 by the second actuator 163, the first injecting unit 1611 may be moved together with the second injecting unit 1631, such that the first reservoir 240 and the injector 245 therein may move together. For example, the first actuator 161 may be controlled to actuate the first injecting unit 1611 independent of actuation of the second injecting unit 1631 to move together with the second injecting unit 1631. Alternatively, the first injecting unit 1611 may be configured to interlock with the second injecting unit 1631 when the second injecting unit 1631 is actuated to move, and thus may move together with the second injecting unit 1631. While the first reservoir 240 and the injector 245 moves together, the speeds thereof, i.e., the speeds of the first and second injecting units 1611 and 1631 may be controlled such the first fluid medicine 241 may not be injected by the injector 245 while the second fluid medicine 251 is injected by the moving first reservoir 240. For that reason, while the second fluid medicine 251 is being provided or injected by moving the first reservoir 240 using the second injecting unit 1631, the first injecting unit 1611 may be controlled not to move faster than the second injecting unit 1631. In some examples, the first and second injecting unit 1611 and 1631 may move in the same speed while the first reservoir 240 is moving, i.e., the second fluid medicine 251 is being injected or provided.

As an another example, a driving axis AX1 of the first actuator 161 and a driving axis AX2 of the second actuator 163 may not be arranged coaxially but parallel to each other, referring to FIGS. 7D and 7E, Specifically, the first injecting unit 1611 may be disposed on the extension of the center axis of the accommodating unit 111. The first injecting unit 1611 may be movable into the first reservoir 240 and may be connected the first actuator 161.

In contrast, the second actuators 163 may include a plurality of actuators provided symmetrically with respect to the first actuator 161. In other words, the plurality of second actuators 163 may be disposed outside the first actuator 161 so as to surround the first actuators 161. The plurality of second actuators 163 may establish structural symmetry for balance of forces. For example, when the medical cooling device 10 includes two second actuators 163, these second actuators 163 may be symmetrically arranged with 180 degrees therebetween around the first actuator 161. When the medical cooling device 10 includes four second actuators 163, such second actuators 163 may be symmetrically arranged with 90 degrees therebetween around the first actuator 161.

The controlling unit 170 may control the plurality of second actuators 163 to be actuated or driven simultaneously when the injection process is performed. With this configuration, the medical cooling device 10 may apply the uniform pressure to the removable cooling medium 20.

Meanwhile, the controlling uni 170 may maintain the temperature of the removable cooling medium 20 at or above the freezing point while the first and second actuators 161 and 163 are driven, i.e. while the medicine is injected, and thus the needle 247 and the needle hole H1 may be prevented from freezing when the medicines flows therethrough.

VII. Cooling Temperature Control: Differential Control & Control Above Freezing Point Hereinafter, according to examples of the present disclosure, a method for controlling a temperature of the fluid medicine via temperature control of the cooling medium and/or other components, will be described. According to the method, the temperature of the fluid medicine may be controlled above a freezing point thereof during an entire process of storing, delivering and dispensing the fluid medicine by differential temperature control under a cooling or freezing environment. More specifically, referring to FIGS. 8A and 8B, features relating to differential temperature control and temperature control above the freezing point in the medical cooling device according to the present disclosure will be described. Referring to FIGS. 9A and 9B, a configuration in which an inner needle is provided inside the medical cooling device and a configuration in which an external syringe is used are separately described.

Figure 8A:
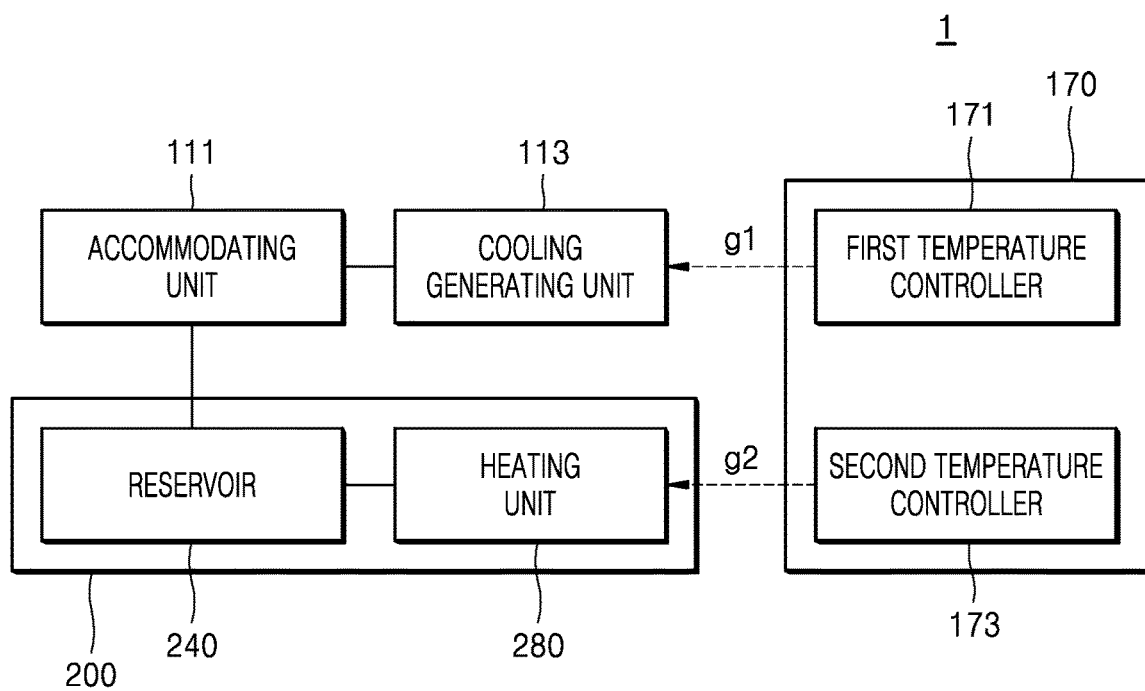
FIGS. 8A and 8B are views illustrating examples of a differential temperature control and a temperature control above a freezing point in the medical cooling device.
Figure 8B:
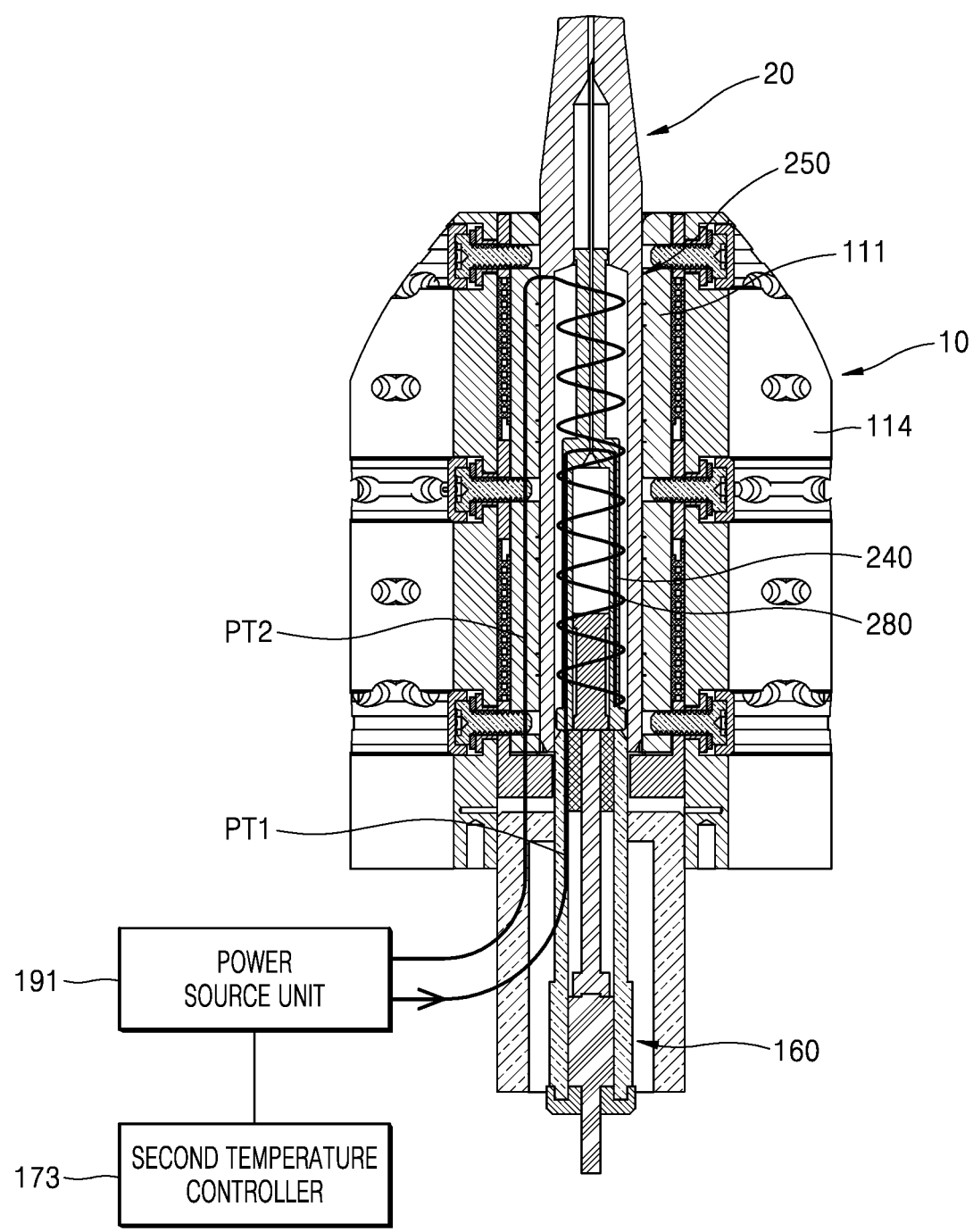
Figure 9A:
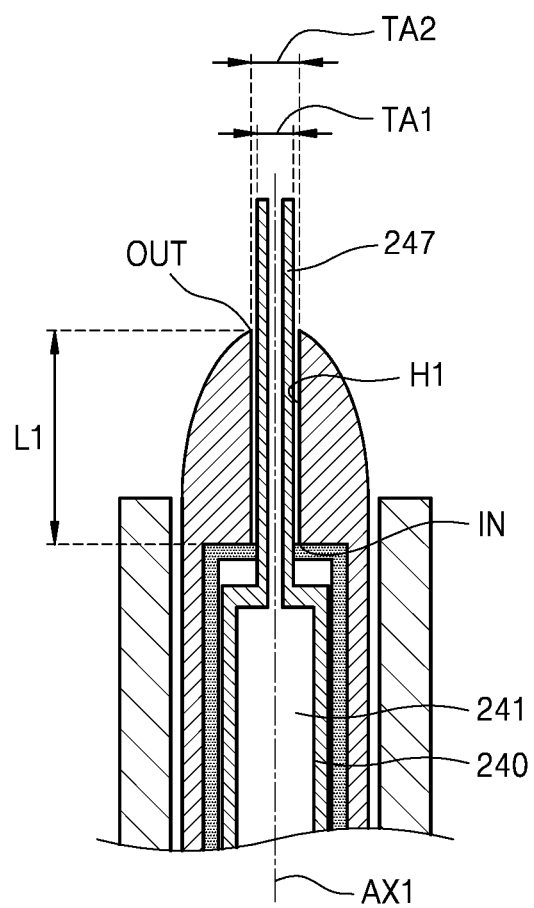
FIGS. 9A and 9B are views illustrating examples of difference configurations of a needle or a syringe in the medical cooling device.
Figure 9B:
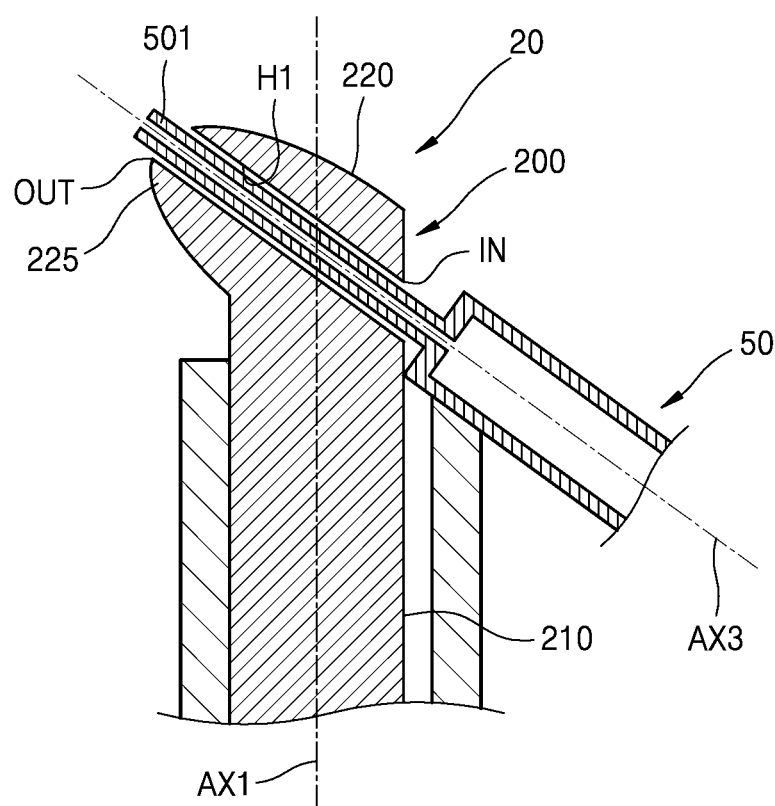

FIGS. 8A and 8B are views for explaining features relating to the differential temperature control and the temperature control above the freezing point in the medical cooling device.

Hereinafter, a method of controlling the temperature of the cooling medium 20 by the controlling unit 170 will be described in detail. FIG. 8A is a block diagram schematically showing a configuration of the controlling unit and the related components. FIG. 8B is a schematic view for explaining a method for differentially controlling the temperature of the cooling medium.

The removable cooling medium 20 may primarily serve to cool the target area, and may secondarily serve to inject the fluid medicine into the target area. Thus, the fluid medicine may present in the cooling medium 20. However, while the cooling medium 20 performs the primary function for the cooling the target, the fluid medicine contained therein may be frozen and solidified and thus may not only be unable to flow to be injected but also lose its therapeutic efficacy. When the cooling energy at a temperature lower than the freezing point is transferred to the stored fluid medicine, the cooling medium 20 may not perform the secondary function for providing the medicine properly and properties of the fluid medicine may be changed due to the phase change, i.e., the freezing. Therefore, it may be critical for the cooling device 10 to maintain the fluid medicine not be frozen in order to performed the functions as intended.

For such reasons, the controlling unit 170 may include a first temperature controller 171 and a second temperature controller 173.

Referring to FIGS. 8A and 8B, the first temperature controller 171 may control the removable cooling medium 20 to be a predetermined first temperature such that the target area contacting the medium 20 is cooled. The first temperature controller 171 may control the operation of the cooling generation unit 113 to transfer the cooling energy to the removable cooling medium 20 accommodated in the accommodating unit 111. More specifically, the first temperature controller 171 may control the operation of the cooling generating unit 113 based on a temperature signal provided by the temperature sensor unit 145, which indicate the temperature sensed by the unit 145. That is, the first temperature controller 171 may provide a control signal g1 to control the unit 113. The first temperature may be set to be the freezing point of the fluid medicine or less, and the first temperature controller 171 may be a cooling controller that performs the cooling of the target area.

Meanwhile, the second temperature controller 173 may control a first region of the cooling medium 20 that may adjacent to the stored fluid medicine or may located corresponds to a position of the stored fluid medicine to be a predetermined second temperature. Thus, the temperature of the fluid medicine in the cooling medium 20 may be kept in the second temperature different from the first temperature.

As shown in FIG. 8B, the cooling medium 20 may be configured to apply the heat to the first reservoir 240 or the second reservoir 250. More specifically, the cooling medium 20 may further include a heating unit 280 which is controlled by the controlling unit 170 to heat the first and second reservoirs 240 and 250. The heating unit 280 may prevent the freezing, i.e., solidification of the fluid medicine in the cooling medium 20.

The heating unit 280 may comprise any mechanism capable of providing the heat to the first and second fluid medicines 241 and 251. For example, the heating unit 280 may a heating wire, a hot wire or a sheath heater surrounding and contracting the first and second reservoirs 240 and 250, to heat these reservoirs 240 and 250 and the medicines 241 and 251 contained therein. The second temperature controller 173 may control the operation of the heating unit 280 to transfer the heating energy to the removable cooling medium 20. More specifically, the second temperature controller 173 may control the operation of the heating unit 280 based on the temperature of fluid medicine. The temperature of the fluid medicine may be directly sense by the temperature sensor unit 145 or other dedicated sensor. Alternately, the temperature of the fluid medicine may be indirectly determined by sensing the temperature of the cooling medium 20. That is, the second temperature controller 173 may provide a control signal g2 to control the heating unit 280. The second temperature may be set above the freezing point of the fluid medicine, and the second temperature controller 173 may be a heating controller for heating the fluid medicine.

The second temperature controller 173 may control the second temperature by using Joule heating. The cooling unit 110 may include a connector configured to electrically or physically connect the heating unit 280 to the other components of the cooling device. The outside conductive surface of the cooling medium 20 may function as the electrical connector, specifically, the portion that contacts with the accommodation unit 111. Further, the connector may be configured to be electrically connected to any power source, for example, the power source unit 191 to provide the power to the heating unit 280. When the removable cooling medium 20 is installed into the cooling device 10, the connector may be configured to be connected to the heating unit 280 installed in the cooling medium 20. More specifically, the connector may include a first connector PT1 disposed at the injecting unit 160 and a second connector PT2 disposed at the accommodating unit 111. When the removable cooling medium 20 is inserted into the medical cooling device 10, the heating unit 280 may be electrically connected to the power source unit 191 via the first and second connectors PT1 and PT2. When the second connector PT2 is disposed at and thus electrically connected to the accommodating unit 111, the electric potential of the accommodating unit 111 may be maintained to be constant. For example, when the second connector PT2 is disposed at the accommodating unit 111, the electric potential of the accommodating unit 111 may be maintained at a potential corresponding to the ground by the power source unit 119. Thus, the electric potential of the medium 20 in contact with the unit 111 may also be maintained at the same ground potential to hinder the leakage of the current to the target area. For these reasons, the connector may be required to be disposed at the accommodating unit 111, at least. In another example, both the first connector PT1 and the second connector PT2 may be disposed at the injecting unit 160.

The second temperature controller 173 may detect the temperatures of the first and second reservoirs 240 and 250 based on resistance value of the heating unit 280 that is electrically connected to the controller 173 via the first and second connectors PT1 and PT2. The second temperature control unit 173 may feedback-control the heating unit 280 based on the measured temperature to maintain the temperature inside the removable cooling medium 20 within a predetermined temperature range. A temperature sensor unit dedicated to the first and second reservoirs 240 and 250 may be provided to the cooling device 20 to the measure the temperatures of these reservoirs 240 and 250.

Meanwhile, the first temperature controller 171 and the second temperature controller 173 may control one of the temperatures before the fluid medicine in the cooling medium 20 is injected, the temperature while the fluid medicine is injected, and the temperature after the fluid medicine is injected and completed. That is, the controlling unit 170 including the first and second temperature controller 171 and 173 may control the temperature of the removable cooling medium 20 in each stage or step of performing the intended function using the cooling medium 20.

For this purpose, the first temperature controller 171 and the second temperature controller 173 may independently control the first temperature and the second temperature. However, the scope of the present disclosure is not limited thereto. For example, the first and second temperature controller 171 and 173 may control the first and second temperatures in association with each other, if required.

Hereinafter, a method for controlling the temperature of the removable cooling medium 20 by stages or steps will be described.

First, the controlling unit 170 may maintain the temperature of the cooling medium 20 above or close the freezing point to remove the possibility of unwanted adhesion between the target area and the cooling medium 20 during the period of the cooling medium 20 initially contacting the target area.

After the secure contact between the cooling medium 20 and the target area, the controlling unit 170 may disinfect the target area by discharging or injecting the second fluid medicine 251, which has not yet frozen as the temperature of the cooling medium is kept above the freezing point, to the target area before cooling the target area using the cooling medium 20. Before discharging the second fluid medicine 251, the controlling unit 170 may also slightly anesthetize only the surface of the target area by preliminarily cooling at a temperature that does not freeze the second fluid medicine 251 using the medium 20, and then disinfect the target area using the second fluid medicine 251. By performing surface anesthesia prior to disinfection by the second fluid medicine 251, the discomfort possibly caused at the target area by the disinfecting agent, i.e., the second fluid medicine 251 thereon is minimized. The second chemical solution 251 may include the disinfecting agent, for example, povidone iodine. As discussed above, the controlling unit 170 may be configured to control the cooling device 10 to perform a pre-cooling function, and a temperature for such pre-cooling may be a temperature that does not cause freezing, for example but not limited to, 0° C. or higher.

Then, the controlling unit 170 may control the temperature of the removable cooling medium 20 to be a sub-zero temperature to reduce the activities of microbes or anesthetize a deep layer or portion of the target area which the injecting needle 247 reaches. More specifically, in this stage or step, the main body 200 of the removable cooling medium 20 may be controlled to have the sub-freezing temperature, and the differential temperature control may be performed simultaneously such that the fluid medicine disposed therein is not frozen. As already discussed above, the controlling unit 170 may control the operation of the cooling generating unit 113 to cool the cooling medium 20.

A temperature range for such cooling after the disinfection may be configured for the purpose of killing bacteria or reducing activity thereof, performing vasoconstriction function, reducing bleeding risk, or minimizing cell damage, in addition to the anesthesia by cooling. As an example of the temperature range for this purpose, the cooling temperature may range from −200° C. to −2° C. Alternatively, the cooling temperature may range from −100° C. to 0° C.

Thereafter, the controlling unit 170 may control the temperature of the cooling medium 20 to a temperature of anesthetizing the target area for needle punctuation. As an example of the temperature range for this anesthetizing purpose, the cooling temperature may range from −40° C. to 10° C. Alternatively, the cooling temperature may range from −0° C. to 10° C. For the case of using a temperature lower than the freezing point of the fluid medicine, the differential temperature control may be performed simultaneously such that the fluid medicine disposed therein is not frozen.

Thereafter, the controlling unit 170 may control the temperature of the cooling medium 20 to a temperature above the freezing point of the first fluid medicine 241, the first reservoir proceeds forward into the cooling medium 20, and the first fluid medicine 241 is injected into the target area. Maintaining the temperature of the cooling medium above the freezing point of the fluid medicine 241 keeps the first fluid medicine 241 from freezing without the help of the differential cooling performed by the first and second temperature controllers 171 and 173.

Thereafter, the controlling unit 170 may control the temperature of the cooling medium 20 such that, after cooling, the cooling medium 20 maintains a temperature higher than the freezing temperature of liquid presented on the target area. More specifically, when the target area is cooled using the cooling medium 20, the target area and the detachable cooling medium 20 may stick or adhere to each other by the ice formation therebetween by cooling. In order to prevent such phenomenon, the controlling unit 170 may control the temperature of the cooling medium 20 to be higher than the freezing temperature of liquid presented on the target area for a predetermined time before the medical device 10 notifies a user to safely separate cooling medium 20 from the target area. With such a stage or step, the cooling medium 20 may be easily separated from the target area without adhering thereto. The controlling unit 170 may control the operation of the cooling generating unit 113 or the heating unit 280 to set the temperature of the cooling medium 20 above the cooling temperature after completing the entire procedures to remove any liquid condensation during the cooling period.

FIG. 9A is a sectional view for schematically showing the cooling medium provided with the inner injecting needle, and FIG. 9B is a sectional view schematically showing the cooling medium provided with the external syringe. Hereinafter, with reference to these drawings, the description will be given to a process in which the fluid medicine is stably injected not being frozen within a path extending from the needle to the target area by controlling the temperature above the freezing point thereof.

Referring to FIG. 9A, the removable cooling medium 20 may include the main body 200 and the reservoir 240. The main body 200 may be detachably installed into the medical cooling device 10 and may be formed with the needle hole H1 through which the injecting needle 247 for injecting the fluid medicine 241 passes. A diameter TA2 of the needle hole H1 may be greater than a diameter TA1 of the needle 247 such that the contact of the needle 247 with the main body 200 may be significantly reduced while the needle 247 passes through the hole H1. Since the main body 200 is maintained at the low temperature to cool the target, the injecting needle 247 may transfer the cooling power to the fluid medicine flowing therein by contacting the main body 200. However, such a configuration as described above may prevent the fluid medicine passing through the needle 247 from freezing.

Further, a member having a diameter similar to the diameter TA1 of the injecting needle 247 may be inserted at an end of the needle hole H1 and thus may guide the needle 247 not to contact the cooling member 20, while passing through the needle hole H1.

Moreover, a surface or a portion of the body 200 surrounding the needle hole H1 may be made of the material having the lower thermal conductivity than that of the other portions of the body 200, or may be coated with such material. For example, such a surface or portion of the body 200 may be made of or coated with the material having the thermal conductivity of 20 W/m-K or less. Thus, the cooling energy of the main body 200 may be prevented from being transferred to the fluid medicine in the needle 247.

As shown in FIG. 9A, when the fluid medicine is injected using the injecting needle 247 disposed in the cooling medium 20, an outlet OUT of the needle hole H1 may be formed at a region of the cooling medium 20 in contact with the target area. Further, an inlet IN of the needle hole H1 into which the injecting needle 247 is first inserted may be formed inside the body 200.

A length L1 of the needle hole H1 along the axial direction of the removable cooling medium 20 may be formed to be less than a predetermined length such that heat transfer by the air or other fluid medicine may be reduced when the fluid medicine flows through the injecting needle 247. For example, the length L1 of the needle hole H1 may be less than 50 mm. Alternatively, the length L1 of the needle hole H1 may be less than 20 mm.

Referring to FIG. 9B, the removable cooling medium 20 may inject the fluid medicine using an external syringe 50 instead of the injection needle 247 accommodated therein. The external syringe 50 may be configured to have a dedicated reservoir or chamber for storing the fluid medicine. Such an external syringe 50 may be filled with the fluid medicine outside the cooling medium 20 and then may be inserted into the cooling medium 20 with storing the fluid medicine therein. Further, the external syringe 50 may comprise a syringe that is already available in a medical field, i.e., available in the market. For these reasons, with the external syringe 50, the cooling medium 20 may provide the fluid medicine in a more convenient manner while simultaneously cooling the target area.

As discussed above, the removable cooling medium 20 may include the insertion portion 210 inserted into the medical cooling device 10 and the non-insertion portion 220 not inserted into the device 10. As shown in FIG. 9B, a direction AX3 in which the non-insertion portion 220 extends from the insertion portion 210 may intersect the axial direction AX1 of the insertion portion 210. That is, the non-insertion portion 220 of the main body 200 may be formed to have a certain angle with respect to the insertion portion 210.

The non-insertion portion 220 may be formed with a needle hole H1 passing through the non-inserting portion 220 along the extension direction AX3 from the tip 225. The needle hole H1 may have an outlet OUT through which an injecting needle 501 of the external syringe 50 may be exposed to the outside of the medium 20, and such an outlet OUT may be formed in a region or portion of the non-insertion portion 220 which is in contact with the target area. That is, the outlet OUT of the needle hole H1 may be formed at the tip 225.

Further, the needle hole H1 may have an inlet IN into which the needle 501 of the external syringe 50 is inserted, and such an inlet IN may be formed opposite to the outlet OUT and may be exposed to the outside of the medium 20. As the needle hole H1 is formed to pass through an outer surface of the main body 200 and the tip 225 via the inlet IN and the outlet OUT as discussed above, the syringe 50 may be inserted into the cooling medium 50 from the outside thereof.

In order to prevent the fluid medicine passing through the needle 501 of the external syringe 50 from freezing due to the low temperature of the removable cooling medium 20, the configuration shown in FIG. 9A may be also applied to an assembly of the medium 20 and the external syringe 50 shown in FIG. 9B. More specifically, as shown in FIG. 9A, the diameter TA2 of the needle hole H1 may be greater than the diameter TA1 of the needle 501, and the surface or a portion of the body 200 surrounding the needle hole H1 may be made of the material having the lower thermal conductivity than that of the other portions of the body 200, or may be coated with such material. The length L1 of the needle hole H1 may be less than 50 mm. Such features may be applied to the medium 20 and the syringe 50 without the substantial modification while producing the same technical advantages. As discussed above, these configurations may reduce the heat transfer to the needle 501 via the needle hole H1. Therefore, when the fluid medicine passes through the injecting needle 501, the cooling energy of the body 200 may not be transferred to needle 501 to prevent the fluid medicine from freezing.

VIII. Cooling Time Period Control

With cooling parameters determined according to the present disclosure, a cooling time period may be controlled to achieve a target cooling temperature within the appropriate time period, depending on the target or intended use.

Hereinafter, with reference to FIGS. 10A and 10B, a description will be given with regard to features related to a medical cooling device implemented with the cooling parameter for the cooling medium. Further, the cooling parameter of the cartridge-type cooling medium, i.e., removable cooling medium will be described with reference to FIG. 11. Hereinafter, the cooling parameters for implementing the cooling device having a specific cooling performance and stability according to an example of the present disclosure will be described.

Figure 10A:
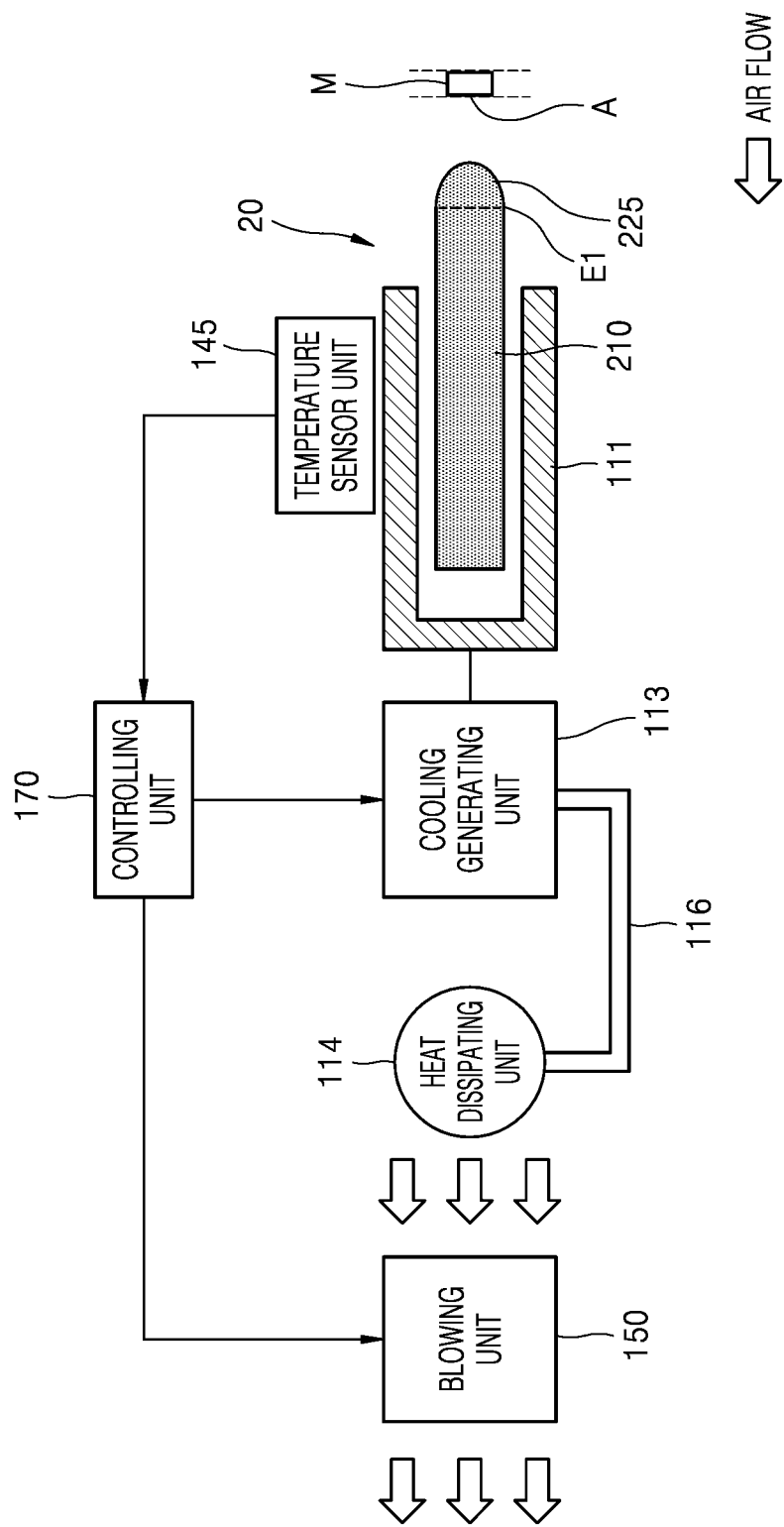
FIGS. 10A and 10B are views illustrating examples of a cooling parameter for the cooling medium.
Figure 10B:
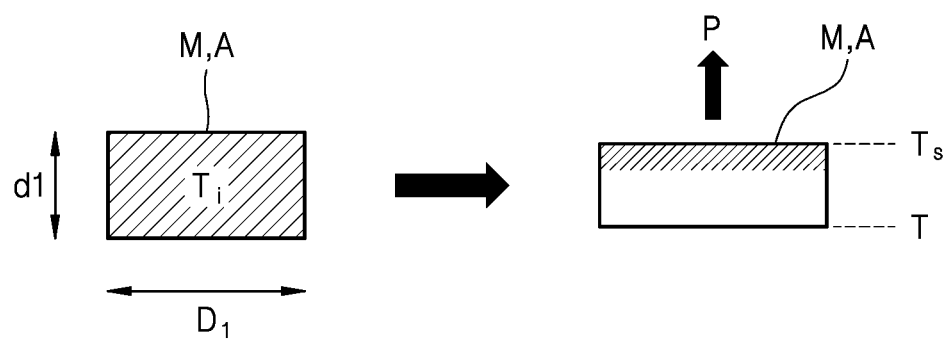

FIGS. 10A and 10B are views showing features associated with the cooling device implemented by the cooling parameter which is defined to have the specific cooling performance and stability.

FIG. 10A is a schematic view showing the cooling device according to the example of the present disclosure, and FIG. 10B is a view for explaining a temperature change in the target area. Referring to FIGS. 10A and 10B, the medical cooling device according to the example of the present disclosure may include a cooling medium 20 and a cooling medium accommodating unit 111. The cooling device may have the same configuration as the medical cooling system 1 or the medical cooling device 10 shown and described with reference to FIGS. 1A to 5G. Hereinafter, the cooling medium 20 and the accommodating unit 111, which is a minimum configuration for realizing the specific cooling performance or stability, will be mainly described, and any repeated or redundant description for other components will be omitted for convenience of explanation.

The cooling medium 20 may have the tip portion 225 that may contact the target area M. The target area M may be referred to as a target region or a target portion having a predetermined volume to be treated and such an expanded definition may be applied whenever the target area is used throughout the present disclosure. The target area M may be formed with a certain contact area A when the cooling medium 20, particularly the tip 225 of the cooling medium 20 is in contact with the target area M. The cooling medium 20 may transfer the cooling energy to the nerves existing within a certain depth d1 of the target area M through the contact area A.

The accommodating unit 111 may be provided in the medical cooling device and may accommodate the cooling medium 20. The accommodating unit 111 may transfer the cooling energy from the cooling generating unit 113, which generates the cooling energy, to the cooling medium 20.

The cooling device having the above-described configuration may be implemented using the cooling parameters defined to have the specific cooling performance or stability. Specifically, the cooling parameter may be set to satisfy the stability allowing a preset temperature deviation and the cooling performance causing temperature change within a preset time period while the cooling medium 20 is in contact with the target area M to cool the same. That is, the cooling parameter may be defined to control at least one of stability of temperature change, a re-entry time period to target temperature, and an arrival time period to target temperature when the cooling medium 20 contacts the target area M and performs cooling to a preset target cooling temperature. In this regard, the cooling parameter may be defined to include at least one of a first cooling parameter G11, a second cooling parameter G12 and a third cooling parameter G13, which are different from one another.

The first cooling parameter G11, the second cooling parameter G12, and the third cooling parameter G13 may be determined based on a target cooling temperature T at the target area M, a heat capacitance C of at least one of the cooling medium 20 and the accommodating unit 111, the contact area A, and cooling power P transferred to the cooling medium 20 from the accommodating unit 111. The heat capacitance C may be, but not necessarily, a total heat capacitance determined by a heat capacitance of the cooling medium 20 and a heat capacitance of the receiving unit 111. Instead, the heat capacitance C may be any one of the heat capacitance s of the cooling medium 20 and accommodating unit 111. A unit of the target cooling temperature T is K, a unit of the heat capacitance C is J/K, a unit of the contact area A is m$^2$, and a unit of the cooling power P is W.

The first cooling parameter G11 may satisfy a following equation such that the temperature deviation of the cooling medium 20 or the accommodating unit 111 may be maintained±5° C. while the cooling medium 20 contacts the target area M and the cooling thereof progresses.

$$G11 = 42\frac{(25-T)A}{c} \le 1$$

When the cooling parameter includes the first cooling parameter G11, the contact area A and the heat capacitance C may be determined according to the target cooling temperature T to satisfy the above equation where the first cooling parameter G11 is 1 or less. The cooling device may be implemented to have the heat capacitance C of the cooling medium 20 or the accommodating unit 111 and the contact area A in the target area M, which are determined by the above equation, and thus may have the stability maintaining the temperature deviation that is +5° C. of the target cooling temperature.

The second cooling parameter G12 may satisfy a following equation such that the temperature deviation of the cooling medium 20 or the accommodating unit 111 may be maintained±5° C. and the time period to return to a first temperature after the temperature of cooling medium 20 is changed to a second temperature different from the first temperature is within 10 seconds, while the cooling medium 20 contacts the target area M and the cooling thereof progresses.

$$G12 = \frac{c+420A}{P} \le 1$$

When the cooling parameter includes the second cooling parameter G12, the contact area A, the heat capacitance C, and the cooling power P may be determined to satisfy the above equation where the second cooling parameter G12 is 1 or less. The cooling device may be implemented to have the heat capacitance C of the cooling medium 20 or the accommodating unit 111, the contact area A in the target area M, and the cooling power P which are determined by the above equation. Thus, the cooling device may have the stability wherein the temperature deviation is maintained±5° C. of the target cooling temperature and the cooling performance wherein the time period to return to an original temperature from a changed temperature is within 10 seconds. Such cooling performance may be required to reliably cool the target area M by the cooling device.

The third cooling parameter G13 may satisfy a following equation such that a time period for reaching to the target cooling temperature T from an initial temperature $T_i$ of the cooling medium 20 or the accommodating unit 111 prior to the cooling is within 60 seconds.

$$G13 = \frac{c(T_i - T)}{60P} \leq 1$$

The initial temperature $T_i$ may be an average value of an initial temperature of the cooling medium 20 and an initial temperature of the accommodating unit 111 measured by the temperature sensor unit 145 provided in the cooling device. In addition, the target cooling temperature T may be a preset temperature for the purpose of precooling, cryodisinfection, cryovasoconstriction, cryoanesthesia, cryocell-destruction, and the like. That is, the third cooling parameter G13 may represent the performance of the medical cooling device that implements the desired target cooling temperature T within 60 seconds.

When the cooling parameter includes the third cooling parameter G13, the heat capacitance C and the cooling power P may be determined to satisfy the above equation where the third cooling parameter G13 is 1 or less. The cooling device may be implemented to have the heat capacitance C of the cooling medium 20 or the accommodating unit 111 and the cooling power P, which are determined by the above equation. Thus, the cooling device may have the cooling performance causing the time period for reaching to the target cooling temperature T from the initial temperature $T_i$ to be within 60 seconds.

Meanwhile, referring to FIG. 10B, when the depth $d_1$ (mm) to the nerves and a cooled area diameter $D_1$ (mm) are determined from the contact area A with the cooling medium 20, a surface temperature $T_s$ at the target area M and the cooling power P for maintaining the temperature $T_s$ may be determined as a function of the target cooling temperature T as follows.

$$T_s = f_1(T)[°\text{C.}]$$

$$P = f_2(T)[W]$$

These equations may be formulas relating to a steady state which does not include information on a transient state, and an interpretation of the transient state may be required to calculate the cooling time period. Hereinafter, a transient state model until the steady state is reached after the cooling medium 20 comes into contact with the target area M will be described.

First, the target area M may have an initial temperature $T_i$. Here, an average temperature $T_f$ at the target region M with respect to a given volume thereof after the cooling may be assumed as an average of the surface temperature $T_s$ and the target cooling temperature T.

$$T_f = \frac{T_s + T}{2}$$

Here, the volume of the target area M may be calculated by the depth $d_1$ and the diameter $D_1$ as follows.

$$V = \frac{\pi D_1^2}{4} d_1$$

Thus, a time period t for reaching the steady-state average temperature $T_f$ from the initial temperature $T_i$ may be calculated by equations as below.

$$\bar{q} = c_p m \Delta T_1 = Pt$$

$$m = \rho V$$

$$\Delta T_1 = T_f - T_i$$

$$\therefore t = \frac{c_p \rho V (T_f - T_i)}{P}$$

In the above equations, $c_p$ is a heat capacitance capacity (J/kg K) of the target area M and $\rho$ is a density (g/cm³) of the target area M.

In view of the above equations, the cooling time period t may be derived as a function of the target cooling temperature T for the nerves.

Figure 11:
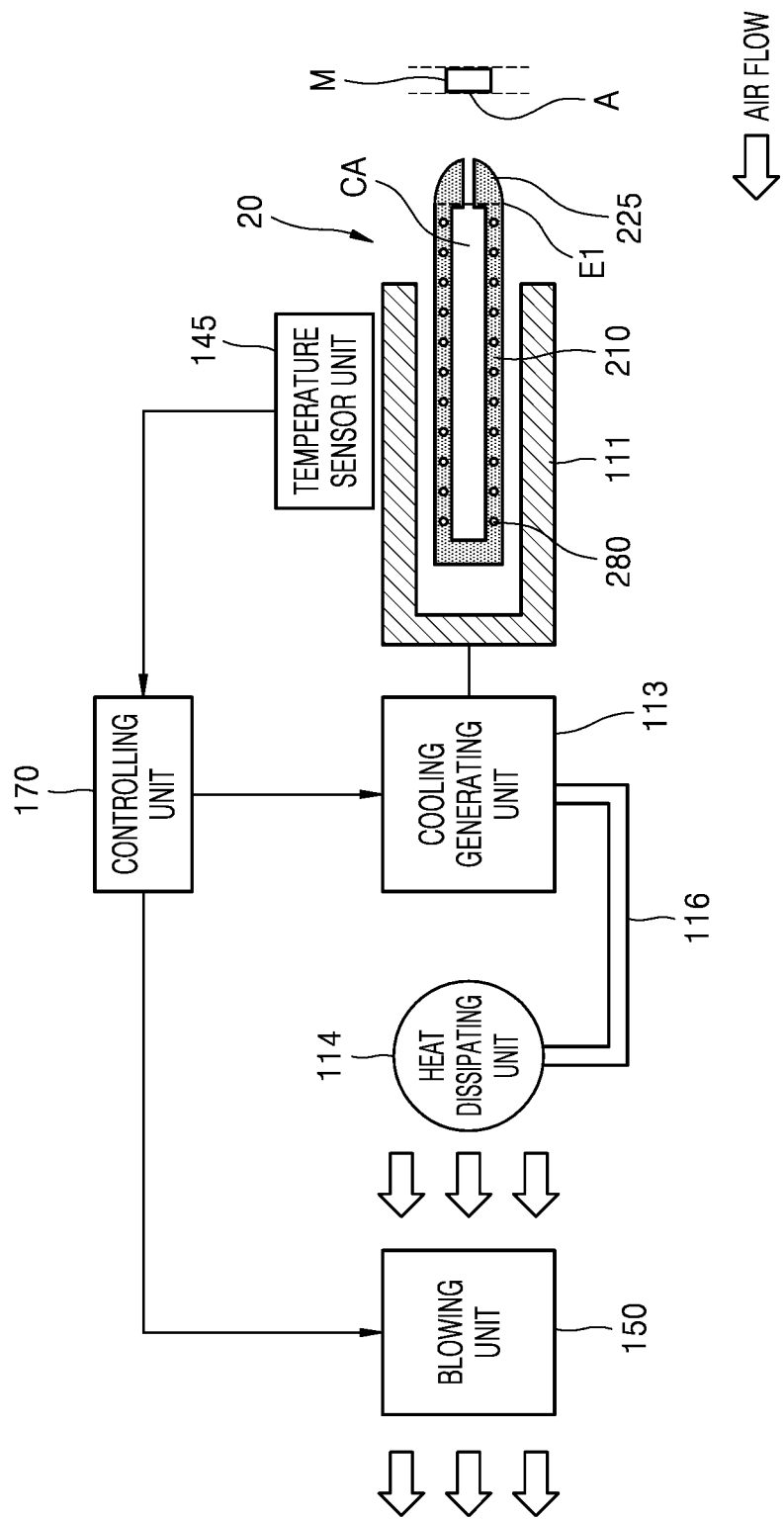
FIG. 11 is a view illustrating an example of a cooling parameter for a different cooling medium.

FIG. 11 is a view showing features associated with the cooling device having the cartridge type cooling medium, which is implemented by the cooling parameter which is defined to have the specific cooling performance and stability.

Referring to FIG. 11, a schematic view showing the cooling device according to the example of the present disclosure is shown and such a medical cooling device may include a cooling medium 20 and a cooling medium accommodating unit 111. The cooling device may have the same configuration as the medical cooling system 1 or the medical cooling device 10 shown and described with reference to FIGS. 6A to 7E, at least. Hereinafter, the cooling medium 20 and the accommodating unit 111, which is a minimum configuration for realizing the specific cooling performance or stability, will be mainly described, and any repeated or redundant description for other components will be omitted for convenience of explanation.

The cooling medium 20 may have the tip 225 that may contact the target area M. Further, the cooling medium 20 may have a reservoir CA configured to store the fluid medicine and the heating unit 280 configured to prevent the fluid medicine from freezing and disposed adjacent to the reservoir CA. The target area M may be referred to as a target region or a target portion having a predetermined volume to be treated and such an expanded definition may be applied whenever the target area is used throughout the present disclosure. The target area M may be formed with a certain contact area A when the cooling medium 20, particularly the tip 225 of the cooling medium 20 is in contact with the target area M. The cooling medium 20 may transfer the cooling energy to the nerves existing within a certain depth d1 of the target area M through the contact area A.

The accommodating unit 111 may be provided in the medical cooling device and may accommodate the cooling medium 20. The accommodating unit 111 may transfer the cooling energy from the cooling generating unit 113, which generates the cooling energy, to the cooling medium 20.

The cooling device having the above-described configuration may be implemented using the cooling parameters defined to have the specific cooling performance or stability. Specifically, the cooling parameter may be set to satisfy the stability allowing a preset temperature deviation and the cooling performance causing temperature change within a preset time period, while the cooling medium 20 is in contact with the target area M to cool the same.

In this regard, the cooling parameter may be defined to include at least one of a first cooling parameter G21, a second cooling parameter G22 and a third cooling parameter G23, which are different from one another. The first, second, and third cooling parameters G21, G22, and G23 may be defined separate and different from the first, second, and third cooling parameters G11, G12, and G13 described with reference to FIGS. 10A and 10B, although these parameters shares similar to one another in aspect of terms.

The first cooling parameter G21, the second cooling parameter G22, and the third cooling parameter G23 may be determined based on a target cooling temperature T at the target area M, a heat capacitance C of at least one of the cooling medium 20 and the accommodating unit 111, the contact area A, cooling power P transferred to the cooling medium 20 from the accommodating unit 111, and electric power h provided to the heating unit 280. The heat capacitance C may be, but not necessarily, a total heat capacitance determined by a heat capacitance of the cooling medium 20 and a heat capacitance of the receiving unit 111. Instead, the heat capacitance C may be any one of the heat capacitances of the cooling medium 20 and accommodating unit 111. A unit of the target cooling temperature T is K, a unit of the heat capacitance C is J/K, a unit of the contact area A is m$^2$, and a unit of the cooling power P of the electric power h is W.

The first cooling parameter G21 may satisfy a following equation such that the temperature deviation of the cooling medium 20 or the accommodating unit 111 may be maintained±5° C. while the cooling medium 20 contacts the target area M and the cooling thereof progresses.

$$G21 = 42\frac{(25-T)A}{c} \leq 1$$

When the cooling parameter includes the first cooling parameter G21, the contact area A and the heat capacitance C may be determined according to the target cooling temperature T to satisfy the above equation where the first cooling parameter G21 is 1 or less. The cooling device may be implemented to have the heat capacitance C of the cooling medium 20 or the accommodating unit 111 and the contact area A in the target area M, which are determined by the above equation, and thus may have the stability maintaining the temperature deviation that is ±5° C. of the target cooling temperature T.

The second cooling parameter G22 may satisfy a following equation such that the temperature deviation of the cooling medium 20 or the accommodating unit 111 may be maintained±5° C. and a time period to return to a first temperature after the temperature of cooling medium 20 is changed to a second temperature different from the first temperature is within 10 seconds, while the cooling medium 20 contacts the target area M and the cooling thereof progresses.

$$G22 = \frac{c+420A}{P-h} \leq 1$$

When the cooling parameter includes the second cooling parameter G22, the contact area A, the heat capacitance C, the cooling power P, and the electric power h may be determined to satisfy the above equation where the second cooling parameter G22 is 1 or less. The cooling device may be implemented to have the heat capacitance C of the cooling medium 20 or the accommodating unit 111, the contact area A in the target area M, and the cooling power P which are determined by the above equation. Thus, the cooling device may have the stability wherein the temperature deviation is maintained±5° C. of the target cooling temperature and the cooling performance wherein the time period to return to an original temperature from a changed temperature is within 10 seconds.

The third cooling parameter G23 may satisfy a following equation such that a time period for reaching the target cooling temperature T from an initial temperature $T_i$ of the cooling medium 20 or the accommodating unit 111 prior to the cooling is within 60 seconds.

$$G23 = \frac{c(T_i - T)}{60(P-h)} \leq 1$$

Here, the initial temperature $T_i$ may be an average value of an initial temperature of the cooling medium 20 and an initial temperature of the accommodating unit 111 measured by the temperature sensor unit 145 provided in the cooling device.

When the cooling parameter includes the third cooling parameter G23, the heat capacitance C, the electric power h, and the cooling power P may be determined to satisfy the above equation where the third cooling parameter G23 is 1 or less. The cooling device may be implemented to have the heat capacitance C of the cooling medium 20 or the accommodating unit 111, the electric power h provided to the heating unit 280, and the cooling power P, which are determined by the above equation. Thus, the cooling device may have the cooling performance causing the time period for reaching the target cooling temperature T from the initial temperature $T_i$ to be within 60 seconds.

IX. Multi-step Temperature Control, Temperature Control by Applications, and Medicine Delivery System Hereinafter, a method for differently cooling the target area based on purposes of use or types of target are by using the medical cooling system or device according to an example of the present disclosure will be described. Firstly, with reference to FIGS. 12A and 12B, a cooling protocol is described based on multi-step temperature control. Referring to FIG. 13, various extended cryotreatments or cryotherapy for the target area will be described in detail, using the cooling protocol of the FIGS. 12A and 12B. Referring to FIG. 14, a medicine delivery system in cooling environment according to an example of the present disclosure will be described.

Figure 12A:
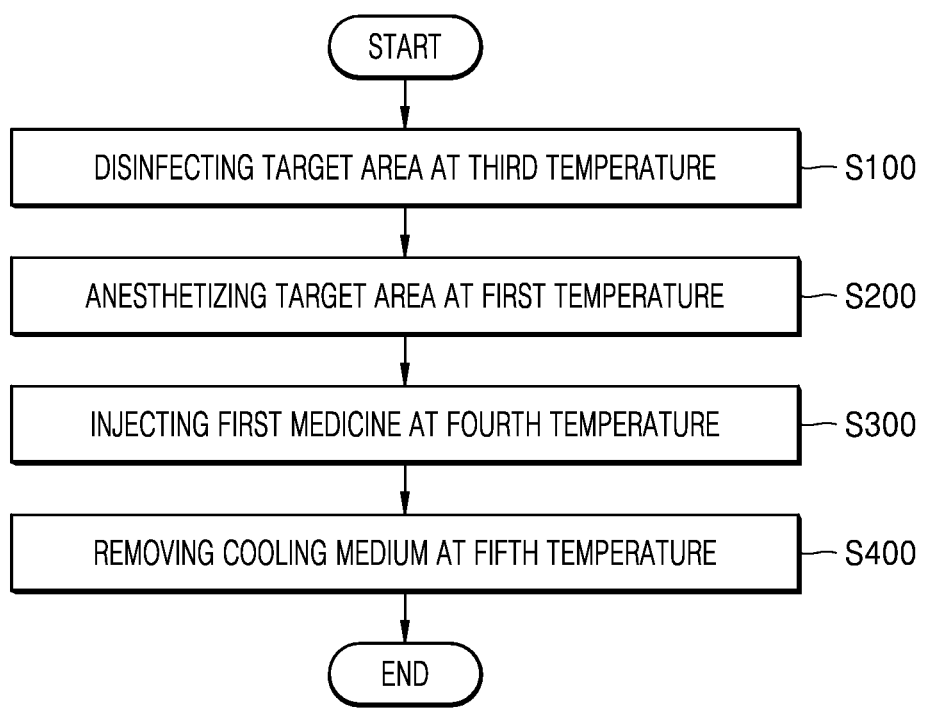
FIGS. 12A and 12B are views illustrating examples of a multi-step temperature control using the medical cooling device.
Figure 12B:
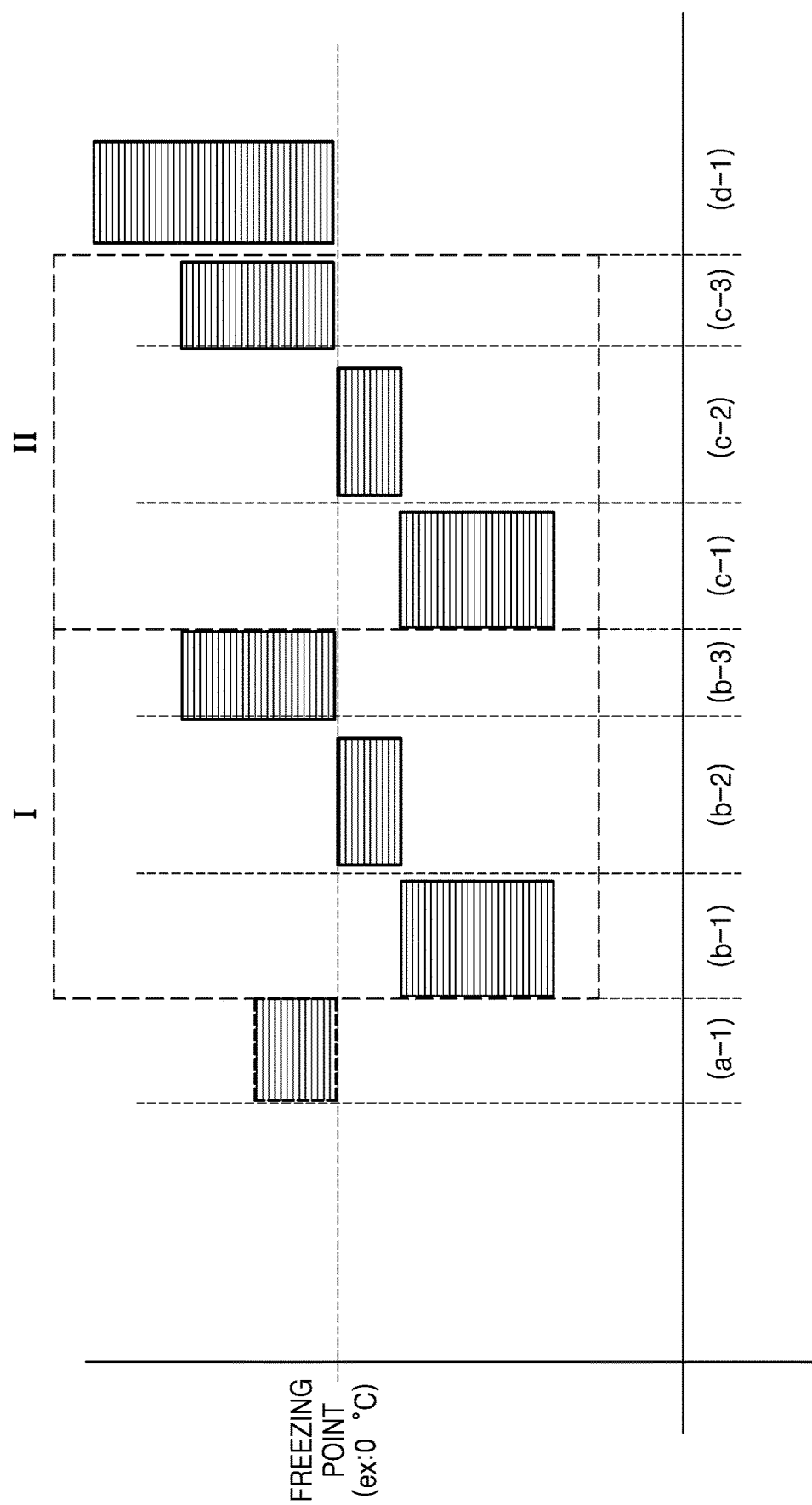
Figure 13:
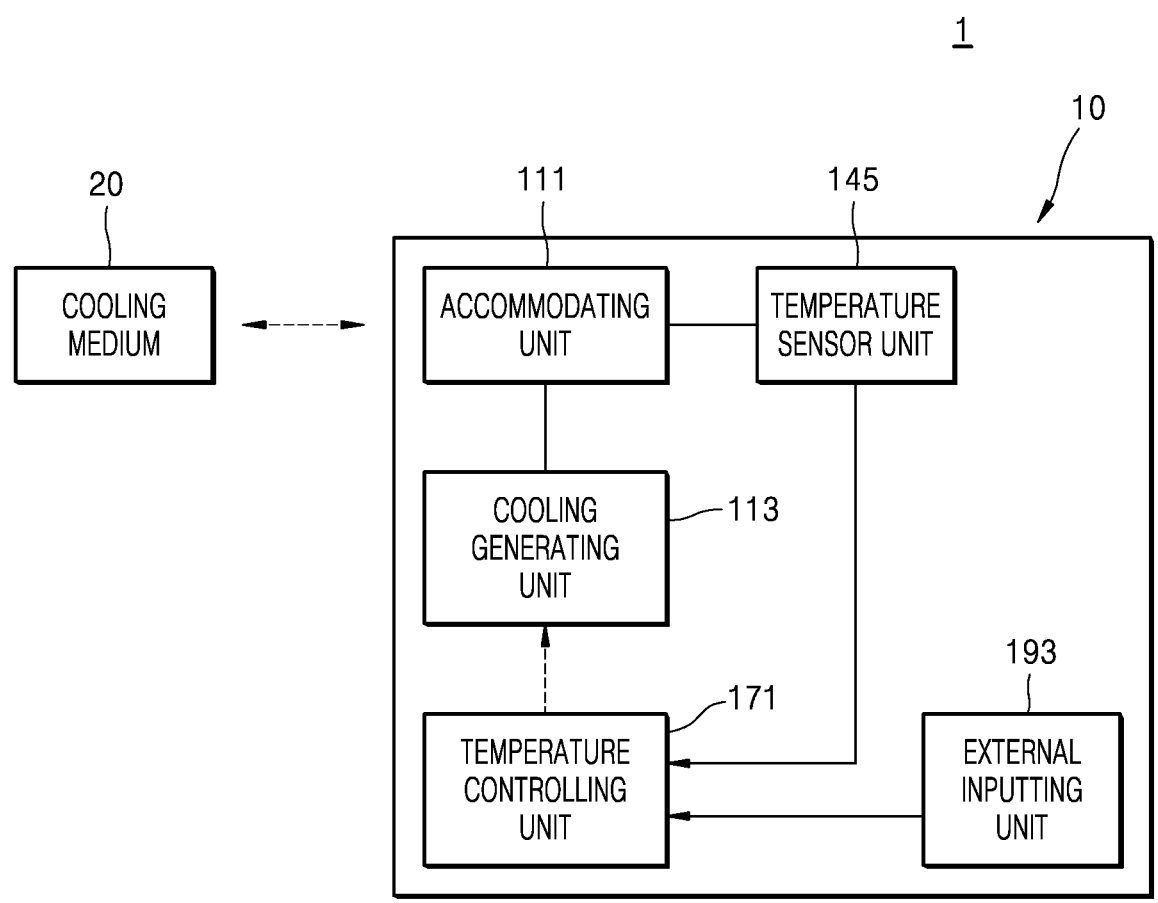
FIG. 13 is a view illustrating an example of an extended cryotreatment or cryotheraphy using the medical cooling device.

FIGS. 12A and 12B are views for explaining features related to the multi-step temperature control using the medical cooling system or device.

FIG. 12A is a flowchart sequentially showing a method for cooling the target area using the medical cooling system or device according to the example of the present disclosure. FIG. 12B is a schematic view or a graph showing another example of the cooling method of FIG. 12A.

Referring to FIG. 12A, the cooling method according to the example of the present disclosure may perform cooling for purposes other than anesthesia such as disinfection, vasoconstriction, hemostasis and so on by precisely controlling the temperature at the target area using the medical cooling device 10. The cooling method according to the example of the present disclosure may be characterized by precisely controlling the temperature at the target area by multi-step, using the cooling medium 20 accommodated in the medical cooling device 10.

In one example, the medical cooling system 1 or device 20 may firstly disinfect or sterilize the target area at a predetermined third temperature, for example, by using the cooling medium 20 having the third temperature (S100). During a step of disinfecting the target area S100, the medical cooling device 10 may disinfect or sterilize the target area at a predetermined second temperature, for example, by providing the disinfecting agent having the second temperature. The second temperature may be higher than the freezing point of the disinfecting agent. Further, the second temperature may be obtained by the cooling medium 20 or/and other component like the heating unit 280 as described above. Such a second temperature may correspond to the second temperature as described in section VII of the present disclosure with reference to FIGS. 8A and 8B.

Further, the medical cooling device 10 may accommodate the cooling medium 20 and may control the temperature of the cooling medium 20 to be the third temperature by transferring the cooling energy to the accommodated cooling medium 20.

The third temperature may be a temperature or a range of temperature that may eliminate or deactivate bacteria present in the target area, i.e., a skin surface of a treated region. There may be various bacteria in the target area that may cause disease. For example, on the eyeballs of the target area, bacteria such as *Staphylococcus aureus*, Coagulase-negative staphylococci, *Streptococcus, Propionibacterium acnes, Bacillus cereus, Enterococcus faecalis, Klebsiella pneumoniae, Enterococcus, Pseudomonas aeruginosa*, Enterobacteriaceae, *Candida albicans, Aspergillus*, and *Fusarium* may exist.

The cooling method according to one example may cool the target area by the third temperature of −2° C. or below, for example, in a range of −90° C. to −2° C. Therefore, the cooling method may disinfect the target area prior to anesthetizing the target area or injecting the fluid medicine into the target area by eradicating or deactivating the bacteria. However, the scope of the present disclosure is not limited thereto, and the third temperature or the range thereof may be determined in view of a temperature range that enables the disinfection at the target area.

After the disinfecting step S100, the medical cooling system 1 or device 10 may cool the target area to be anesthetized by a predetermined first temperature using the cooling medium 20 (S200). The third temperature in the disinfecting step S100 may have a range lower than the lowest temperature that may set as the first temperature. More particularly, the third temperature in the disinfecting step S100 is intended to eliminate the bacteria or reduce activity thereof, and thus should may be lower than the first temperature at which the actual anesthesia is performed. For example, the first temperature may be higher than −2° C. and may be 10° C. or below, which is entirely higher than the range of the third temperature. Such a first temperature in the cooling step S100 may correspond to the first temperature as described in section VII of the present disclosure with reference to FIGS. 8A and 8B.

If the cooling medium 20 has a reservoir for storing a first fluid medicine, the first liquid medicine may be additionally injected into the target area at a predetermined fourth temperature (S300) after performing the cooling step S200. Alternatively, an injecting step S300 may be performed while the cooling step S200 is being performed. As described above, the cooling medium 20 may include the heating unit 280 to prevent the first fluid medicine from freezing while cooling the target area, and thus the fourth temperature of the first fluid medicine may be controlled to be different from the first temperature of the cooling medium 20 even when the cooling medium 20 is cooled. More specifically, the fourth temperature may be controlled to be higher than the freezing point of the first fluid medicine, at least. Further, the fourth temperature may be obtained using the heating unit 280 or/and other component like the cooling medium 20. Such a fourth temperature in the injecting step S300 may correspond to the second temperature as described in section VII of the present disclosure with reference to FIGS. 8A and 8B.

However, as the temperature of the first fluid medicine may be lowered by contacting the cooling medium 20 while the first fluid medicine stored in the cooling medium 20 is delivered or injected to the target area, the cooling medium 20 itself may be controlled to maintain a temperature higher than the temperature in the cooling step S200. Thus, the fourth temperature may have a range higher than the lowest temperature that may be set as the first temperature range. For example, the fourth temperature may be higher than 0° C. and may be 25° C. or below.

When the cooling step S200 or the injecting step S300 is completed, the medical cooling device 10 may be separated from the target area. However, the cooling medium 20 may adhere to the surface of the target area due to the temperature differences by cooling at the time of contacting the target area. If the cooling medium 20 is removed while adhering to the target area, the surface of the target area may be damaged. In order to prevent such damage, before the cooling medium 20 is separated from the target area, the temperature of the cooling medium 20 may be increased to a fifth temperature (S400). In a separating step S400, the fifth temperature may be higher than the lowest temperature that may be set as the first temperature. For example, the fifth temperature may be in a range of −2° C. to 30° C.

Through the above described steps, the cooling method according to one example of the present disclosure may perform the anesthesia for one time or the injection of medicine for one time. If the multiple anesthesia or the multiple injections are required, the disinfecting step S100, the cooling step S200, and the injecting step S300 may be repeated as required and then the cooling medium 20 may be separated from the target area according to the separating step S400. Alternatively, the temperatures as described above may be redefined sequentially in order of the steps S100-S400 for better understanding. In this case, the third temperature in the disinfecting step S100 may be redefined as a first temperature. In the same manner, the first temperature in the cooling step S200, the fourth temperature in the injecting step S300, and the fifth temperature in the separating step S400 may be redefined as a second temperature, a third temperature, and a fourth temperature, respectively. Further, the second temperature for injecting the disinfecting agent in the disinfecting step S100 may be newly defined as a fifth temperature. Such redefinition simply intends to change names of the steps S100-S400, and thus does not alter the substantial control therein.

Referring to FIG. 12B, according to another example, the cooling method using the medical cooling system 1 or device 10 may include a first injecting step II of a first fluid medicine and a second injecting step I of a second fluid medicine. The cooling medium 20 may store the first fluid medicine and the second fluid medicine therein and the medical cooling device 10 may sequentially deliver the second and first fluid medicines of the cooling medium 20 to the target area. Further, the first fluid medicine may comprise a therapeutic or treating agent, and the second fluid medicine may comprise a disinfecting agent.

In the cooling method the second injecting step I for disinfecting the target area with the second fluid medicine, i.e., the disinfecting agent may be performed prior to the first injecting step II for injecting the first fluid medicine. The second injecting step I of the second fluid may be carried out by performing a disinfecting step b-1, a cooling step b-2 and an injecting step b-3 for the second fluid medicine, using the multi-step temperature control as described above in detail. In FIG. 12B, the disinfecting step b-1, the cooling step b-2 and the injecting step b-3 are separated based on the freezing point. In the second injecting step I, the freezing point may be a freezing point of the second fluid medicine. That is, during the injection of the second fluid medicine as the disinfecting agent, the cooling medium 20 may have a temperature range higher than the freezing point of the second fluid medicine to prevent the freezing of the second fluid medicine when the second fluid medicine is delivered or injected to the target area (b-3).

If the cooling medium 20 having a temperature below the freezing point, for example, a sub-zero temperature is directly applied to the target area, the target are may be damaged due to the temperature difference. Therefore, a precooling step a-1 may be performed before the second injecting step I to cool the cooling medium 20 to be a temperature higher than the freezing point. For example, the precooling temperature may have a range of 0° C. to 10° C.

Referring to FIG. 12B again, after the second injecting step I is performed, the first injecting step II for injecting the first fluid medicine to the target area may be performed. Similar to the second injecting step I, the first injecting step II may be carried out by performing a disinfecting step c-1, a cooling step c-2 and an injecting step c-3 for the first fluid medicine, using the multi-step temperature control as described above in detail. In FIG. 12B, the disinfecting step c-1, the cooling step c-2 and the injecting step c-3 are separated based on the freezing point. In the first injecting step II, the freezing point may be a freezing point of the first fluid medicine. Although the freezing point of the first fluid medicine is the same as the freezing point of the second fluid medicine in FIG. 12B, the freezing points of the first and second fluid medicines may be different from each other. Likewise, during the injection of the first fluid medicine, the cooling medium 20 may have a temperature range higher than the freezing point of the first fluid medicine to prevent the freezing of the first fluid medicine while the first fluid medicine is delivered or injected to the target area (c-3).

After the first injecting step II, the cooling medium 20 may be controlled to have a temperature higher than a freezing point, for example, a temperature above 0° C. or the fifth temperature described referring to the FIG. 12A, may maintain such a temperature for a predetermined time period, and then may be separated from the target area (d-1).

In the above cooling method as shown in FIG. 12B, the first injecting step II and the second injecting step I are defined and described to conform with the configuration and the operation of the first and second reservoir 240 and 250 as shown in FIGS. 6A-6G in which the second fluid medicine of the second reservoir 250 is injected (i.e., second injecting step I) prior to injecting the first fluid medicine of the first reservoir 240 (i.e., first injecting step II). However, for better understanding, the first injecting step (II) and the second injecting step (I) as above may be redefined sequentially in order of implementation. In this case, the first injecting step (II) may be changed to be a second injecting step (II) for injecting the treating agent and the second injecting step (I) may be changed to be a first injecting step (I) for injection the disinfecting agent. The detailed description as already provided above may be applied to these newly defined steps without modification.

Meanwhile, the cooling method using the medical cooling system 1 or device 10 may be characterized by operating in different temperature ranges that are set by the multiple steps. The medical cooling device 10 may create and maintain such temperature ranges by controlling the output of the cooling generating unit 113 that produces the cooling energy. The medical cooling device 10 may perform the cooling below a specific temperature rapidly by applying a maximum allowable current or a maximum allowable voltage to the cooling generating unit 113. However, a proper current or voltage control algorithm may be required to configure and maintain the different temperature ranges as mentioned above.

Specifically, the current value applied to the cooling generating unit 113 for maintaining the steady state temperature at the target area may be determined by a given target cooling temperature Ts, a heat dissipating area Area 1 of the heat dissipating unit 114, and a convection heat $Q_{conv}$ by the blowing unit 150. The convection heat $Q_{conv}$ may be determined by following equations:

$$Q_{conv}=P+Q_{cond}+Q_{Joule}[W]$$

$$P=f_1(T_s)$$

$$Q_{cond}=f_2(I)$$

$$Q_{Joule}=f_3(I)$$

wherein P is cooling power for maintaining the steady state temperature at the target area, $Q_{cond}$ is heat generated due to the temperature difference inside the thermoelectric element when the cooling generating unit 113 comprises the thermoelectric element, and $Q_{Joule}$ is Joule heat generated by the applied current. As described above, the convection heat $Q_{conv}$ may be given as a function of the current, from which the current value for maintaining the steady state temperature may be derived as follows.

$$I=f_4^{-1}(Q_{conv})$$

In the cooling method using the medical cooling system or device, the steps of the disinfection, the anesthesia, the injection, and the separation may be performed using the cooling properly adjusted for such steps by controlling the temperature. This cooling method may eliminate the bacteria in the target area and prevent the bacteria from spreading to the cooling device. The cooling method may further constrict the blood vessels in the target area and tighten the cells, and thus may minimize injury when the needle penetrates the target area. In addition, the cooling method may separate the cooling medium after raising the temperature of the target area or the cooling medium higher than a preset temperature, after performing the anesthesia or the injection of medicine, and thus may minimize damage to the target area.

FIG. 13 is a view for explaining features related to the extended cryotreatment or cryotheraphy for the target area using the medical cooling device.

FIG. 13 is a block diagram schematically showing the medical cooling device according to an example of the present disclosure. Referring to FIG. 13, a medical cooling device 10 includes a cooling medium accommodating unit 111, a temperature sensor unit 145, a cooling generating unit 113 and a temperature controlling unit 171. The medical cooling device 10 may further include an external inputting unit 193.

Here, a removable cooling medium 20 may receive the cooling energy while being inserted into the medical cooling device 10, and may contact the target area to perform the cooling function. The accommodating unit 111 may be detachably accommodates the removable cooling medium 20, and may transfer the cooling energy to the removable cooling medium 20. The cooling medium 20, the accommodating unit 111 and the sensor unit 145, and the cooling generating unit 113 in this example may be the same as corresponding elements as described above, and thus any repeated description thereto will be omitted.

The temperature controlling unit 171 may control the cooling medium 20 to be in a predetermined first temperature range such that the target area in contact with the cooling medium 20 is cooled. In one example, the first temperature range may have a range of −200° C. to 0° C. Further, the temperature controlling unit 171 may control the cooling medium 20 to be in a second temperature range selected within the first temperature range in response to an external input.

Specifically, the medical cooling device 10 may receive the cooling medium 20 to cool the target area, as described above, and may be further applied to cryohemostasis, cryosurgery and disinfection by bacteria inactivation. The temperature controlling unit 171 may select one of the second temperature ranges corresponding to various applications or purpose as described above within the first temperature range which is the entire temperature range that can be implemented by the medical cooling apparatus 10. Further, the temperature controlling unit 171 may control the temperature of the removable cooling medium 20 according to the selected second temperature range.

In this regard, the medical cooling device 10 may further include the external inputting unit 193 for generating an input signal according to the external input.

The temperature controlling unit 171 may select the second temperature range of −50° C. to 0° C. when the external input is a first input instructing cryohemostasis at the target area.

Generally, the cryohemostasis is achieved by exposing emitted blood at a temperature below freezing point or by contracting blood vessels. When the cooling is performed in a range of −50° C. to −180° C. using liquid nitrogen, N$_2$O, or CO$_2$, the cells may be destroyed more than intended, and thus the hemostasis should be performed at −50° C. or higher. In addition, the cooling may be used to induce contraction of blood vessels, i.e., vasoconstriction. Such a vasoconstriction temperature may be 0° C. or less. Therefore, when the cooling device 20 is used for the cryohemostasis, the second temperature range may selected to be the range of −50° C. to 0° C., and blood vessels may be contracted without cell destruction to stop bleeding.

The removable cooling medium 20 used for the cryohemostasis may be configured to be inserted into a narrow region without obstructing a field of view for hemostasis during surgery.

Meanwhile, when the external input is a second input for instructing the cryosurgery in the target area, the temperature controlling unit 171 may select the second temperature range of −180° C. to −20° C.

In the present disclosure, the cryosurgery may mean destroying a cell to remove the target area such as a wart and a spot from the body. For complete removal of warts, spots, and the like, cell roots should be cooled and destroyed. Generally, the cryosurgery temperature may range from −50° C. to −40° C. depending on the cooling time period. However, such a temperature may be the cooling temperature required for cryosurgery at the surface of the skin, and an actual temperature thereof may vary depending on a cell depth. For example, assuming that the cell depth is 5 mm from the surface of the skin, the cooling temperature at the surface of the skin should be approximately −120° C. to destroy the cell roots.

Although it is most ideal to remove only the target area requiring the cryosurgery, the cells around the target area may be destroyed by the transfer of the cooling energy. The cooling medium 20 according to an example of the present disclosure may be configured to minimize the cell destruction around the target area. For example, the cooling medium 20 may be configured to adjust a size of an area thereof that contacts the target area, depending on a size of the target area. Further, the cooling medium 20 or the cooling device 10 may have a heater for heating a portion around the target.

As another example, compressed carbon dioxide may be used to implement the cryosurgery, apart from cooling the target area using the cooling medium 20. Specifically, compressed carbon dioxide may be used to make the cooling temperature at the skin surface to be about −50° C. The target area may be rapidly cooled using the Joule-Thomson effect, in which a temperature is sharply reduced when compressed carbon dioxide is injected at low pressure. When carbon dioxide is cooled below −78° C. at atmospheric pressure, dry ice particles may be generated to further absorb sublimation heat.

In order to prevent the cell destruction around the target area, a heat source may be provided around a nozzle where carbon dioxide is injected. This heat source may comprise an electric heater or a thermoelectric element. Here, as the thermoelectric element may be used as a heat pump that unidirectionally transfers the heat by Joule heating unlike the electric heater that bidirectionally transfers the heat by Joule heating, the thermoelectric element may control a temperature of gas injected from the nozzle with less energy. Therefore, the temperature of injected carbon dioxide may be precisely adjusted according to the depth and size of the target area or cell, and thus the cryosurgery may be enabled without destroying the surrounding cells.

Further, the heat source including the thermoelectric element or the electric heater may be configured to enclose the target area subject to the cryosurgery, i.e., to be thermally coupled to a cooling boundary or interface surrounding the target area and thus partitioning the target area from the other cell. A temperature of the cooling boundary may be maintained at or above the cryosurgery temperature by the controlling unit 171. Therefore, this may limit the cryosurgery to a central area within the cooling boundary, i.e., a central area of the target area. Especially, when the cryosurgery for a deep region from the surface of the target area is required, the cooling at the proper cryosurgery temperature may easily spread in a depth direction. Specifically, the cooling boundary may be maintained at a cryoanesthesia temperature, through which peripheral cells near the central where the cryosurgery occurs may be maintained in an anesthetic state.

Meanwhile, when the external input is a third input for instructing the bacteria inactivation in the target area, the temperature control unit 171 may set the second temperature range of −90° C. to −2° C. This temperature range may enable eliminating or deactivate the bacteria that may be present in the target area, i.e., the skin surface of the target area. There may be various bacteria in the target area that can cause disease. For example, on the eyeballs as the target area, bacteria such as *Staphylococcus aureus*, Coagulase-negative staphylococci, *Streptococcus, Propionibacterium acnes, Bacillus cereus, Enterococcus faecalis, Klebsiella pneumoniae, Enterococcus, Pseudomonas aeruginosa*, Enterobacteriaceae, *Candida albicans, Aspergillus*, and *Fusarium* may exist.

The controlling unit 171 may cool the target area by applying the second temperature range of −90° C. to −2° C. and thus may eradicate the above bacteria or deactivate the bacteria to disinfect the target area before anesthetizing or injecting the medicine into the target area.

As described above, the medical cooling device according to the examples of the present disclosure may be used for various therapeutic applications such as the cryohemostasis, the cryosurgery, the disinfection, and so on, in addition to the cryoanesthesia by controlling the cooling temperature appropriate for such applications. Further, the medical cooling device according to the examples of the present disclosure may be used by medical staffs of hospitals such as ophthalmology, dentistry, dermatology, and surgery, but may also be used for various purposes at home through adaptive temperature control.

Figure 14A:
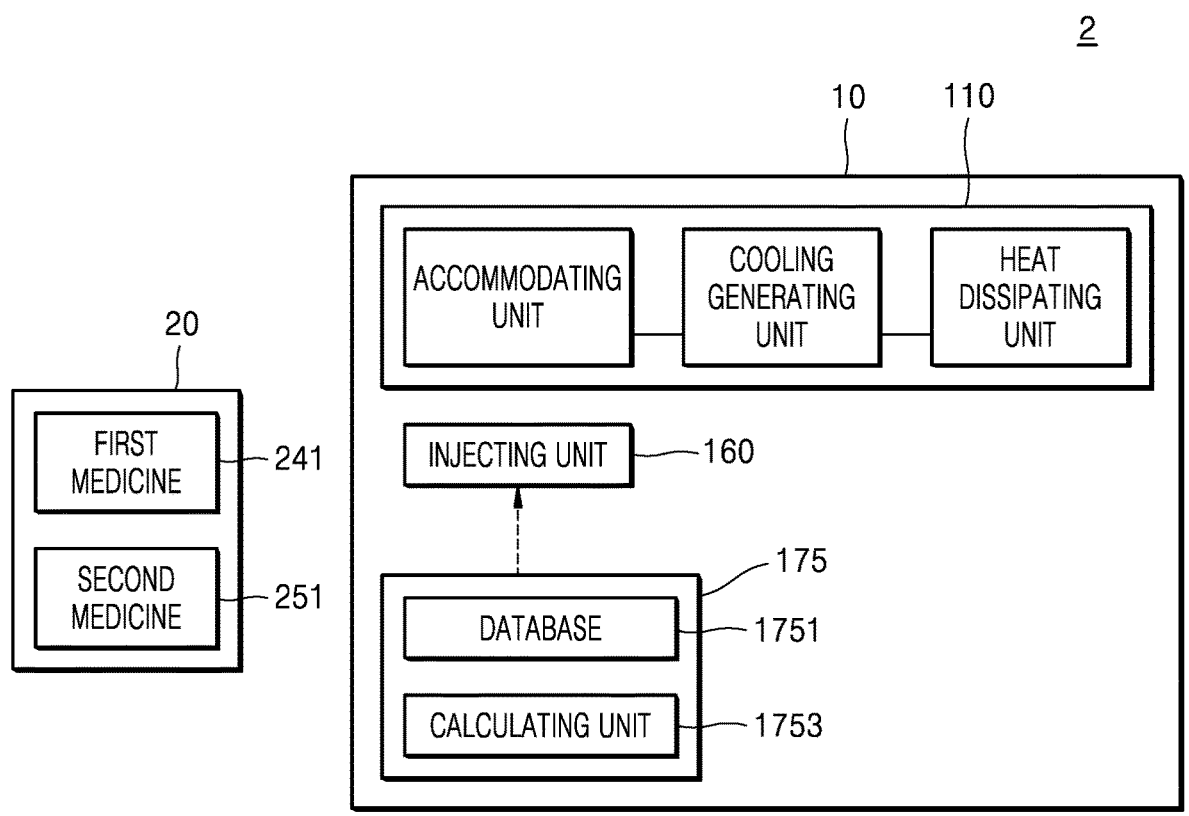
FIGS. 14A and 14B are views illustrating examples of a drug or medicine delivery system.
Figure 14B:
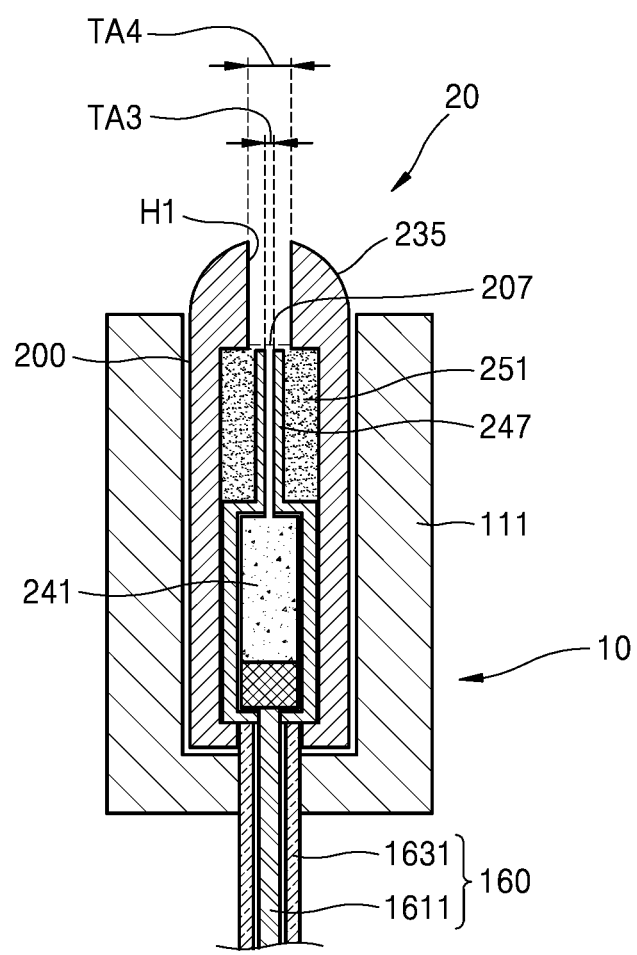

FIGS. 14A and 14B are views explaining features related to a drug or medicine delivery system. FIG. 14A is a block diagram schematically showing the medicine delivery system according to an example of the present disclosure, and FIG. 14B is a schematic view showing the medicine delivery system of FIG. 14A.

Referring to FIGS. 14A and 14B, a medicine delivery system 2 according to an example of the present disclosure may include a storage medium 20 for storing a fluid medicine and a cooling device 10.

The storage medium 20 may contain a first fluid medicine 241 of a first dosage and may further include a second fluid medicine 251. Here, the first fluid medicine 241 may comprise a therapeutic agent for treating a target area, for example, the eye, and such a therapeutic or treating agent may include an ophthalmic medicine or an ophthalmic composition. The second fluid medicine 251 may comprise a disinfectant or a disinfecting agent. The first fluid medicine 241 will be specifically described below.

In the present disclosure, the term "ophthalmic drug or medicine" or "ophthalmic composition" may refer to an anesthetic injected prior to the treatment of ocular disease or a medicine used to treat, ameliorate, or prevent the ocular disease.

In the present disclosure, the term "ocular disease" may refer to a disease that affects or relates to a part or an area of the eye or the entire eye. In a broad sense, the eye may include an eyeball, tissues and body fluids that make up the eyeball, muscles around the eye (such as rectus and oblique), and the optic nerve in or near the eyeball.

The term "anterior segment disease" may refer to a disease that affects or related to an anterior segment (i.e., a front portion of the eye) such as muscles around the eyes, eyelids, eye tissues or body fluids that are located in front of a ciliary body or a posterior wall of a lens capsule. That is, the anterior segment disease primarily affects or related to a conjunctiva, a cornea, an anterior chamber, an iris, a posterior chamber (behind the iris, but in front of the posterior wall of the lens capsule), a lens, the lens capsule, and vessel and nerves passing through the anterior segment.

Therefore, the anterior segment diseases may include, for example, aphakia; pseudophakos; astigmatism; blepharospasm; cataract; conjunctival disease; conjunctivitis; corneal disease; keratohelcosis; scheroma; eyelid disease; tear organs disease; lacrimal duct obstruction; myopia; presbyopia; pupil disease; refractive disorders, and strabismus. As the clinical goal of glaucoma treatment is to reduce a pressure of aqueous fluid in the anterior chamber of the eye (i.e., to reduce the intraocular pressure), glaucoma may be also considered the anterior segment disease.

The term "posterior segment disease" may refer to a disease that affects or related to a posterior segment (i.e., a rear portion of the eye) such as choroid or sclera (located in a rear of a plane through the posterior wall of the lens capsule), vitreous, vitreous chamber, retina, retinal pigment epithelium, Bruch's membrane, optic nerve (i.e., optic disk), and vessel and nerves passing through the posterior segment.

Therefore, the posterior segment diseases may include, for example, neuroretinopathy; Behcet's disease; choroidal neovascularization; diabetic uveitis; histoplasmosis; infections such as fungal or virus-induced infections; macular degeneration such as acute macular degeneration; non-exudative senile macular degeneration and exudative senile macular degeneration; edema such as macular edema, cystic macular edema, and diabetic macular edema; multifocal choroiditis; eye trauma affecting posterior segment or position; eye tumor; retinal disorders such as central retinal vein occlusion, diabetic retinopathy (including proliferative diabetic retinopathy), proliferative vitreoretinopathy (PVR), retinal artery occlusion, retinal detachment, and uvea retinopathy; sympathetic ophthalmia; Vogt-Koyanagi-Harada (VKH) syndrome; uveal diffusion; eye disease caused or influenced by laser treatment; eye disease caused or influenced by photo dynamic therapy or photocoagulation; radiation retinopathy; epiretinal membrane disorder; branch retinal vein occlusion; ischemia optic nerve disorder; non-retinopathy diabetic retina malfunction; retinitis pigmentosa; and glaucoma.

The drug or medicine may include, for example, anti-angiogenic agents, antibiotics, anti-viral agents, or anti-inflammatory agents, and more particularly, may include triamcinolone, ganciclovir, forscarnet, cidofovir, fomvirse, methorexate, vancomycin, ceftazidime, amikacin, amphotericin, voriconazole, or dexamethasone.

The anti-angiogenic agent may a substance (e.g., VEGF antagonist or VEGF receptor antagonist) that inhibits vascular endothelial growth factor (VEGF) (e.g., human VEGF). Such anti-angiogenic agents may be used for diseases involving angiogenic eye disorders.

The term "angiogenic eye disorder" as used in the present disclosure may refer to any disease of the eye caused by growth or proliferation of blood vessels, by blood vessel leakage, or related thereto. Non-limiting examples of angiogenic eye disorders that may be treated using the method of the present disclosure may include choroidal neovascularization, age-related macular degeneration (AMD), diabetic retinopathy, diabetic macular edema (DME), central retinal vein occlusion (CRVO), corneal neovascularization, and retinal neovascularization.

The term "human VEGF" used in the present disclosure may refer to 165-amino acid human vascular endothelial cell growth factor and related 121-, 189-, and 206-amino acid vascular endothelial cell growth factors as well as the allelic variants of these growth factors in nature and changed forms thereof, as described in a document [Leung et al., Science 246: 1306 (1989) and Houck et al., Mol. Endocrin. 5: 1806 (1991)].

The term "VEGF receptor" or "VEGFR" used in the present disclosure may refer to a cell receptor for VEGF, usually a cell-surface receptor found in vascular endothelial cells and variants thereof that have the ability to bind hVEGF. An example of the VEGF receptor is a transmembrane receptor in tyrosine kinases, which are fms type tyrosine kinases (fit) [DeVries et al., Science 255: 989 (1992) and Shibuya et al., Oncogene 5; 519 (1990)]. The fit receptor includes an extracellular domain, a transmembrane domain, and an intracellular domain with tyrosine kinase activity. The extracellular domain is involved in the binding of VEGF, while the intracellular domain is involved in signal transduction. Another example of the VEGF receptor is a flk-1 receptor (also known as KDR) [Matthews et al., Proc. Nat. Acad. Sci. 88: 9026 (1991); Terman et al., Oncogene 6: 1677 (1991); and Terman et al., Biochem. Biophys. Res. Commun. 187: 1579 (1992)). The binding of VEGF to the fit receptor forms two or more high molecular weight complexes with an apparent molecular weight of 205,000 to 300,000 Da. A complex of 300,000 Da is considered to be a dimer containing two receptor molecules bound to a single molecule of VEGF.

The term "VEGF antagonist" used in the present disclosure may refer to any molecule that blocks, decreases or interferes with the normal biological activity of VEGF. The VEGF antagonists include molecules that interfere with the interaction between VEGF and natural VEGF receptors, for example, molecules that prevent or otherwise interfere with the interaction between VEGF and VEGF receptors by binding to VEGF or VEGF receptors. Specific exemplary VEGF antagonists include anti-VEGF antibodies, anti-VEGF receptor antibodies, and VEGF receptor-based chimeric molecules (also referred to as "VEGF-Traps"), aptamers capable of blocking VEGF or VEGFR, neutralizing anti-VEGFR antibodies, an inhibitor of VEGFR tyrosine kinase. VEGF receptor-based chimeric molecules include chimeric polypeptides comprising two or more immunoglobulin (Ig)-like domains of the VEGF receptor such as VEGFR1 (also referred to as Flt1) and/or VEGFR2 (also referred to as Flk1 or KDR), and may also contain a polymerization domain (e.g., Fc domain that facilitates the polymerization (for example, a dimerization) of two or more chimeric polypeptides). More particularly, the VEGF antagonist may contain acetylated Flt-1 (1-3)-Fc, Flt-1(1-3R→N)-Fc, Flt-1 (1-3ΔB)-Fc, Flt-1 (2-3ΔB)-Fc, Flt-1 (2-3)-Fc, Flt-1 D2-VEGFR3D3-FcΔC1(a), Flt-1 D2-Flk-1D3-FcΔC1 (a), or VEGFR1R2-FcΔC1 (a).

The terms "antibody (Abs)" and "immunoglobulin (Igs)" are glycoproteins having the same structural characteristics. Antibodies exhibit binding specificity for particular antigens, while immunoglobulins include both other antibody-like molecules lacking antigen specificity and antibodies. Polypeptides of immunoglobulin are produced, for example, at low levels by the lymphatic system, and at increased levels by myeloma.

The term "antibody" is used in the present disclosure in its broadest sense and specifically covers monoclonal antibodies (including full length monoclonal antibodies), polyclonal antibodies, multispecific antibodies (e.g., bispecific antibodies) and antibody fragments that exhibit the desired biological activity.

The term "antibody fragment" includes a portion of the full length antibody, generally its antigen binding or variable region. Examples of antibody fragments include Fab, Fab', F(ab')2 and Fv fragments; diabody; linear antibodies; single chain antibody molecules; and multispecific antibodies formed from antibody fragments.

The term "monoclonal antibody" used in the present disclosure, refers to an antibody obtained from a population of substantially homogeneous antibodies, and individual antibodies that make up the population are identical except for possible natural mutations that may be present in minor amounts. Monoclonal antibodies directed with regard to a single antigen site are very specific. Also, unlike conventional (polyclonal) antibody preparations, which typically contain different antibodies directed against different antigenic determinants (epitopes), each monoclonal antibody is directed against a single antigenic determinant group on the antigen. The modifier "monoclonal" indicates that the characteristics of the antibody are obtained from a substantially homogeneous population of antibodies and is not to be construed as requiring production of the antibody by any particular method. For example, the monoclonal antibody used in accordance with the present disclosure may be prepared by the hybridoma method first described in a document [Kohler et al., Nature 256: 495 (1975)], or by recombinant DNA methods (e.g., U.S. Pat. No. 4,816,567). The term "monoclonal antibody" may also be isolated from the phage antibody library using techniques described, for example, in documents [Clackson et al., Nature 352: 624-628 (1991) and Marks et al., J. Mol. Biol. 222: 581-597 (1991)].

Specifically, the monoclonal antibody includes "chimeric" antibodies (immunoglobulins) in which a part of the heavy chain and/or light chain is derived from a particular species or is identical to or similar to the corresponding sequence of an antibody belonging to a particular antibody class or subclass, but the remainder of the chain(s) is derived from another species or is identical or similar to the corresponding sequences of an antibody belonging to another antibody class or subclass, as well as fragments of such chimeric antibodies exhibiting the desired biological activity [U.S. Pat. No. 4,816,567 and Morrison et al., Proc. Natl. Acad. Sci. USA 81: 6851-6855 (1984)].

A "humanized" form of a non-human (e.g., rodent) antibody is a chimeric antibody comprising minimal sequence derived from non-human immunoglobulin. For the most part, humanized antibodies are human immunoglobulin (recipient antibody) that hypervariable region residues of the recipient have been replaced with hypervariable region residues from non-human species (donor antibodies) such as mouse, rat, rabbit or non-human primates with the desired specificity, affinity and ability. In some cases, framework region (FR) residues of human immunoglobulin are replaced with corresponding non-human residues. Moreover, the humanized antibody may comprise a residue not found in the donor antibody or the recipient antibody. These modifications may be made to further improve antibody performance. In general, the humanized antibody will substantially comprise all of one, typically two or more variable domains that all or substantially all of the hypervariable regions correspond to those of a non-human immunoglobulin and all or substantially all of the FR regions are those of human immunoglobulin sequences. In addition, the humanized antibody will arbitrarily comprise an immunoglobulin constant region (Fc), typically at least a portion of the constant region of a human immunoglobulin.

"Single chain Fv" or "sFv" antibody fragment comprises VH and VL domains of an antibody present in a single polypeptide chain. Generally, Fv polypeptide further comprises a polypeptide linker between the VH and VL domains such that sFv forms a preferred structure for antigen binding.

The term "diabody" refers to a small antibody fragment having two antigen binding sites, including a heavy chain variable domain (VH) linked to a light chain variable domain (VL) in the same polypeptide chain (VH-VL). Using a linker too short to allow confluence between two domains on the same chain, the domain is forcedly confluent with the complementary domain of another chain to create two antigen binding sites. Diabodies are specifically described, for example, in European Patent EP 404,097, International Patent Publication No. 93/11161, and a publication [Hollinger et al., Proc. Natl. Acad. Sci. USA, 90: 6444-6448 (1993)]. In one example of the present disclosure, the VEGF antagonist may comprise ranibizumab, afliberceptin, or bevacizumab.

The medicine or drug is prepared and stored in the form of a lyophilized preparation or aqueous solution by mixing the medicine having the desired purity with any pharmaceutically acceptable carrier, excipient or stabilizer [Remington's Pharmaceutical Sciences 16th Edition, Osol, A. Ed. (1980)]. Suitable carriers, excipients or stabilizers are non-toxic to the recipient at the employed dosages and concentrations and include buffers such as phosphates, citrates and other organic acids; antioxidants including ascorbic acid and methionine; preservatives (e.g., octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol); low molecular weight (less than about 10 residues) polypeptide; proteins, such as serum albumin, gelatin or immunoglobulins; hydrophilic polymers such as polyvinylpyrrolidone; amino acids such as glycine, glutamine, asparagine, histidine, arginine or lysine; monosaccharides, disaccharides and other carbohydrates including glucose, mannose or dextrin; chelating agents such as EDTA; sugars such as sucrose, mannitol, trehalose or sorbitol; salt formation counter ions, such as sodium; metal complexes (e.g., Zn-protein complexes); and/or non-ionic surfactants such as TWEEN™, PLURONICS™ or polyethylene glycol (PEG).

In one example of the present disclosure, the VEGF antagonist may be provided in a stable, pharmaceutically acceptable formulation, and the formulation may include a liquid formulation suitable for ophthalmic use (e.g., IVT). The liquid formulation comprises a pharmaceutically effective amount of the VEGF antagonist. The formulations may also include one or more pharmaceutically acceptable carriers, buffers, isotonic agents, stabilizers, and/or excipients. Examples of pharmaceutically acceptable liquid formulations include, but are not limited to, VEGF antagonists, buffering agents, organic co-solvents such as polysorbates, isotopes such as NaCl and optionally stabilizers such as sucrose or trehalose in a pharmaceutically effective amount.

Stability may be determined in many ways at a specific point of time, including determination of pH, visual inspection of color and appearance, methods known in the art, for example, determination of total protein content by UV spectroscopy. Purity may be determined, for example, by SDS-PAGE, size exclusion HPLC, determination of bioassay of activity, isoelectric focusing and isoaspartate quantification.

According to one example of the bioassay, the bioassay is useful for determining VEGF antagonist activity, and BAF/3 VEGFR1/EPOR cell line is used to determine VEGF165 bound by the VEGF antagonist of the present disclosure. Liquid formulations may be stored in an oxygen-inducing environment. The oxygen-inducing environment may be generated by storing the formulation under an inert gas, such as, for example, nitrogen or argon. The liquid formulation may preferably be stored at about 5° C.

The formulation as described above may be a lyophilizable formulation. The lyophilizable formulations may be reconstituted or restored into solutions, suspensions, emulsions or any other suitable form for administration or use. The lyophilizable formulations are typically prepared first as a liquid, followed by freezing and lyophilization. A total liquid volume prior to lyophilization may be less, equal to or greater than a final reconstituted volume of the lyophilized formulation. A lyophilization process is known to those skilled in the art and typically involves sublimation of water from a frozen formulation under controlled conditions.

The lyophilized formulation may be stored at a wide range of temperature. The lyophilized formulation may be stored in cold temperature at 25° C. or less, for example, at 2-8° C. or may be stored at room temperature (e.g., approximately 25° C.). Preferably, the lyophilized formulation is stored at about 25° C. or less, more preferably at about 4-20° C. or less; at 4° C. or less; at about −20° C.; at about −40° C.; at about −70° C. or about −80° C. or less. The stability of lyophilized formulation can be determined by numerous methods in the art, for example, by visual appearance of a solidified cake and/or by moisture content.

The lyophilized formulation is typically reconstituted or restored by addition of an aqueous solution to dissolve the lyophilized formulation. A wide variety of aqueous solutions may be used to reconstitute the lyophilized formulation. Preferably, the lyophilized formulation is reconstituted using water. The lyophilized formulation is preferably reconstituted with a solution consisting essentially of water (e.g., USP WFI or injectable water) or a bacteriostatic water (e.g., USP WFI with 0.9% (w/v) benzyl alcohol). However, solutions containing buffers and/or excipients and/or one or more pharmaceutically acceptable carriers may also be used.

Freeze-dried or lyophilized formulations are typically prepared from liquids, i.e., solutions, suspensions, emulsions, and the like. Thus, the liquid subjected to freeze-drying or lyophilizing preferably contains all of the ingredients desired in a final reconstituted liquid formulation. As a result, when reconstituted, the freeze-dried or lyophilized formulations will provide the liquid formulations desired for reconstitution.

In one example, the storage medium 20 may store the ophthalmic composition or ophthalmic medicine therein. The storage medium 20 may include a needle for injection through which the fluid medicine passes and is discharged to the outside. When the storage medium 20 contains only the first fluid medicine 241, a needle hole H1 formed at the storage medium 20 may serve as the injection needle as described above for injecting the first fluid medicine 241, and any separate needle may not be provided to the storage medium 20. Thus, a diameter TA4 of the needle hole H1 may be considered in order to calculate an injection speed of the first fluid medicine 241.

In another example, as shown in FIG. 14B, the storage medium 20 may configured to separately store both of the first and second fluid medicines 241 and 251. More specifically, the storage medium 20 may be configured to have reservoirs storing the first and second medicines 241 and 251, respectively. Further, while the second fluid medicine 251 may be injected through the needle hole H1, the first fluid medicine 241 may be injected using a needle 247 configured to communicate with the reservoir storing the first fluid 241. A configuration as shown in FIG. 14B is substantially the same as the configuration as shown in FIGS. 6A-6G, and thus the description for any corresponding elements and components provided referring to FIGS. 6A-6G will be incorporated by reference for the configuration in FIG. 14B and any further description will be omitted. Accordingly, when the storage medium 20 contains both the first and second fluid medicines 241 and 251, a diameter TA3 of the needle 247 may be considered in order to calculate the injection speed of the first fluid medicine 241. For the same reason, the diameter TA4 of the needle hole H1 may be considered to calculate the injection speed of the second fluid medicine 251. Hereinafter, the examples of the present disclosure will be described mainly based on the configuration of FIG. 14B.

Referring back to FIG. 14A, the cooling device 10 may include an injection unit 160 configured to be connected to the storage medium 20 to deliver to the target area the first fluid medicine 241 of the first dosage within a first time period. The cooling device 10 may transfer the cooling energy to the storage medium 20 to cool the target area using the storage medium 20.

Here, the storage medium 20 may include an insertion portion inserted into the cooling apparatus 10 and a non-insertion portion. The non-insertion portion of the medium 20 may transfer to the target area the cooling energy transferred from the insertion portion.

The drug or medicine delivery system 2 may anesthetize the target area by cooling the same, prior to injecting the medicine into the target area. The medicine should be injected into the target area before the nerve in the target area is awakened. Thus, the medicine delivery system 2 may be characterized by injecting the first fluid medicine 241 into the target area within the first time period that may be limited in view of many factors, after the target area is anesthetized.

The first time period may be determined by a degree of cooling in the target area. The degree of cooling may be determined by at least one of a cooling performing time period, an anesthesia maintenance time period, a cooling temperature, and a distance from a surface to the nerve at the target area. In one example, the first time period may be less than one minute, but the scope of the present disclosure is not limited thereto. In another example, when the anesthesia maintenance time is taken into account, it takes about 10 to 15 seconds for the temperature of the target area to be increased after the anesthesia is achieved and the cooling is stopped, and another about 10 to 15 seconds for the nerve to wake up due to the increase in temperature. Therefore, the first time period may be further limited within 30 seconds, after the anesthesia is achieved and the cooling is stopped.

Meanwhile, the medicine delivery system 2 may further include an injection rate or speed controlling unit 175 configured to control an injection rate by the injecting unit 160 to deliver the first medicine fluid 241 within the first time period to the target area. The injection rate controlling unit 175 may calculate the injection rate of the fluid medicine from the storage medium 20 by using at least one of the degree of cooling in the target area, the first dosage, the first time period, the diameter TA3 of the needle 247, a type of the first fluid medicine 241.

The injection rate controlling unit 175 may include a database 1751 and a calculating unit (or calculator) 1753. The database 1751 may store data required for calculation of the injection rate at the calculating unit 1753, such as physical properties corresponding to the types of fluid medicines, for example, viscosity. The calculating unit 1753 may calculate the injection rate using the stored data at the database 1751. The injection rate controlling unit 175 may control the injecting unit 160 to operate at the injection rate calculated by the calculating unit 1753, such that the first fluid medicine 241 is delivered to the target area within the first time period.

In yet another example, the storage medium 20 may further include an information storage unit configured to store information regarding the type of the first fluid medicine 241 contained therein and the first dosage and to transmit such stored information to the cooling device 10, particularly to the controlling unit 175. Such an information storage unit may be provided on a surface of the storage medium 20 in a form of a pattern. This pattern may comprise a bar code, a QR code, a character code, and/or a graphic code. The cooling device 10 may further include a sensing unit (or a sensor) such as a bar code reader capable of receiving the information from the information storage unit.

Alternatively, the information storage unit may comprise a circuit chip (or a processor), a memory, or an assembly of these circuit chip and memory for storing and transmitting the above information. When the storage medium 20 is inserted into the cooling device 10, the information storage unit thereof is may be electrically connected to the cooling device 10 to enable transmitting the stored information to the device 10. Therefore, the injection rate controlling unit 175 may receive the information regarding the type of the first fluid medicine 241 stored in the storage medium 20, the first dosage, and the like, and may store the received information at the database 1751 to allow the calculating unit 1753 to calculate the injection rate.

As described above, the medicine delivery system according to the example of the present disclosure may inject the therapeutic agent into the target area within the optimal time period in association with the anesthesia by cooling, and thus may produce maximized effect from the injected agent.

Although a number of examples have been described, it should be understood that other modifications and implementations can be devised by those skilled in the art that will fall within the spirit and scope of the principles of this disclosure. More particularly, various variations and modifications in the structure or the configuration are possible within the scope of the disclosure, the drawings and the appended claims. In addition to variations and modifications in the configuration, alternative uses will also be apparent to those skilled in the art.

What is claimed is:

1. A method of cooling a target area of a subject patient and subsequently providing a fluid medicine to the target area for medical treatment, the method comprising:
    providing a handheld medical device, the handheld medical device comprising a tip configured to directly or indirectly cool the target area and a reservoir containing the fluid medicine, the tip having a through-hole configured to inject the fluid medicine to the target area therethrough;
    moving the tip toward to the target area such that the tip contacts or is disposed adjacent to the target area;
    first adjusting, at a controller of the handheld medical device, a temperature of the tip to a first temperature for cooling the target area while the tip contacts or is disposed adjacent to the target area, the first temperature being lower than a freezing temperature at which at least a portion of the fluid medicine freezes;
    subsequently to the first adjusting, second adjusting, at the controller, the temperature of the tip to a second temperature which is higher than the first temperature and the freezing temperature;
    subsequently to the second adjusting, injecting the fluid medicine contained in the reservoir through the through hole of the tip to the target area while the tip having the second temperature contacts or is disposed adjacent to the target area such that the fluid medicine does not become frozen while passing through the through hole of the tip;

wherein the handheld medical device further comprises a needle in fluid communication with the reservoir, and wherein, when injecting the fluid medicine, the needle moves toward the target area through the through hole such that the needle is inserted into the target area and the fluid medicine is injected into the target area;

wherein the handheld medical device further comprises a thermal conductor including the tip and a thermoelectric element configured to cool the thermal conductor, and wherein the reservoir is disposed outside the thermal conductor while the needle is disposed in the through hole.

2. The method of claim 1, wherein the first temperature is equal to or lower than −2° C.

3. The method of claim 2, wherein the first temperature ranges from −90° C. to −2° C. for performing disinfection of the target area.

4. The method of claim 1, wherein the second temperature ranges from 0° C. to 25° C.

5. The method of claim 1, further comprising third adjusting the temperature of the tip to a third temperature to anesthetize the target area, wherein the third temperature is greater than −2° C. and equal to or less than 10° C.

6. The method of claim 5, wherein the third adjusting is performed between the first adjusting and the second adjusting.

7. The method of claim 1, further comprising disinfecting the target area with the first temperature.

8. The method of claim 1, wherein the method further comprises, after injecting the fluid medicine, controlling the thermoelectric element for adjusting the temperature of the tip to a fourth temperature at which the tip does not adhere to the target area.

9. The method of claim 8, wherein the fourth temperature is greater than −2° C. and equal to or less than 30° C.

10. The method of claim 1, wherein the tip comprises a contact surface configured to contact the target area, and wherein the through hole has an opening in the contacting surface.

11. The method of claim 1, wherein the handheld medical device further comprises a secondary reservoir containing a secondary fluid medicine, and wherein the method further comprises, prior to the first adjusting, injecting the secondary fluid medicine to the target area through the through hole of the tip.

12. The method of claim 11, wherein the fluid medicine is a therapeutic agent and the secondary fluid medicine is a disinfecting agent.

13. The method of claim 11, further comprising, prior to injecting the secondary fluid medicine, adjusting the temperature of the tip to a fifth temperature, the fifth temperature being higher than a freezing temperature at which at least a portion of the secondary fluid medicine freezes.

14. The method of claim 11, further comprising, prior to injecting the secondary fluid medicine, adjusting the temperature of the tip to a sixth temperature for cooling the target area, the sixth temperature being lower than a freezing temperature at which at least a portion of the secondary fluid medicine freezes.

* * * * *